United States Patent
Green et al.

(10) Patent No.: US 12,151,000 B2
(45) Date of Patent: *Nov. 26, 2024

(54) TOLEROGENIC ARTIFICIAL ANTIGEN-PRESENTING CELLS

(71) Applicant: THE JOHNS HOPKINS UNIVERSITY, Baltimore, MD (US)

(72) Inventors: Jordan J. Green, Baltimore, MD (US); Stephany Yi Tzeng, Baltimore, MD (US); Kelly Rhodes, Baltimore, MD (US); Giorgio Raimondi, Baltimore, MD (US); Marcos Iglesias Lozano, Baltimore, MD (US); Jamie Spangler, Baltimore, MD (US); Jakub Tomala, Baltimore, MD (US); Derek VanDyke, Baltimore, MD (US); Randall A. Meyer, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 92 days.

This patent is subject to a terminal disclaimer.

(21) Appl. No.: 17/602,856

(22) PCT Filed: Apr. 13, 2020

(86) PCT No.: PCT/US2020/027989
§ 371 (c)(1),
(2) Date: Oct. 11, 2021

(87) PCT Pub. No.: WO2020/226854
PCT Pub. Date: Nov. 12, 2020

(65) Prior Publication Data
US 2022/0160891 A1 May 26, 2022

Related U.S. Application Data

(60) Provisional application No. 62/916,404, filed on Oct. 17, 2019, provisional application No. 62/832,957, filed on Apr. 12, 2019.

(51) Int. Cl.
| | |
|---|---|
| *A61K 47/69* | (2017.01) |
| *A61K 9/50* | (2006.01) |
| *A61K 31/436* | (2006.01) |
| *A61K 47/62* | (2017.01) |
| *A61K 47/68* | (2017.01) |
| *A61P 37/00* | (2006.01) |

(52) U.S. Cl.
CPC ........ *A61K 47/6937* (2017.08); *A61K 9/5031* (2013.01); *A61K 31/436* (2013.01); *A61K 47/62* (2017.08); *A61K 47/6813* (2017.08); *A61K 47/6845* (2017.08); *A61K 47/6849* (2017.08); *A61P 37/00* (2018.01)

(58) Field of Classification Search
CPC ............... A61K 47/6937; A61K 47/62; A61K 47/6845; A61K 47/6849; A61K 47/6813; A61K 9/5031; A61K 31/436; A61P 37/00
See application file for complete search history.

(56) References Cited

U.S. PATENT DOCUMENTS

| | | | | |
|---|---|---|---|---|
| 2010/0047262 | A1* | 2/2010 | Rasmussen | A61P 25/28 424/185.1 |
| 2010/0233079 | A1* | 9/2010 | Jakob | A61P 29/00 424/1.49 |
| 2012/0114759 | A1* | 5/2012 | Green | A61K 9/06 977/773 |
| 2014/0370099 | A1* | 12/2014 | Green | A61K 39/0001 424/234.1 |
| 2016/0045551 | A1* | 2/2016 | Brentjens | C07K 16/2803 |
| 2017/0114130 | A1* | 4/2017 | Rondon | A61P 37/06 |
| 2018/0346969 | A1 | 12/2018 | Chang et al. | |

FOREIGN PATENT DOCUMENTS

WO    WO 2013/086500    6/2013

OTHER PUBLICATIONS

A. Salerno, et al. The effect of cyclosporin A, FK506 and rapamycin on the murine contact sensitivity reaction. Clin. Exp. Immunol. 1998; 112: 112-119. (Year: 1998).*
International Search Report and Written Opinion for PCT/US20/27989. Mailed Nov. 18, 2020. 6 pages.
Battaglia et al., Immune intervention with T regulatory cells: Past lessons and future perspectives for type 1 diabetes., Seminars in Immunology., (2011), pp. 182-194, vol. 23(3).
Bluestone et al., T reg cells—the next frontier of cell therapy., Science., (2018), pp. 154-155, vol. 362(6411).
Boder et al., Yeast surface display for screening combinatorial polypeptide libraries., Nature Biotechnology., (1997), pp. 553-557, vol. 15(6).
Boyman et al., Selective stimulation of T cell subsets with antibody-cytokine immune complexes., Science., (2006), pp. 1924-1927, vol. 311(5769).
Boyman et al., The role of interleukin-2 during homeostasis and activation of the immune system., Nature Reviews Immunology., (2012), pp. 180-190, vol. 12(3).

(Continued)

*Primary Examiner* — Michael P Cohen
(74) *Attorney, Agent, or Firm* — Casimir Jones, S.C.; Thomas A. Isenbarger

(57) ABSTRACT

The disclosure is directed to a biodegradable particle comprising a polyester or polyester blend, a first protein that binds to an immune cell, and a second protein that promotes proliferation and/or activation of immune cells, and a third soluble protein or small molecule encapsulated within the particle. The second protein is a fusion protein comprising at least a portion of an antibody and at least a portion of a cytokine (i.e., an immunocytokine). The disclosure also is directed to methods for treating a disease or condition in a subject (e.g., an autoimmune disease) comprising administering the aforementioned biodegradable particle to the subject.

16 Claims, 31 Drawing Sheets
Specification includes a Sequence Listing.

(56) References Cited

OTHER PUBLICATIONS

Bromberg et al., Inflammation and cancer: IL-6 and STAT3 complete the link., Cancer Cell., (2009),pp. 79-80, vol. 15(2).

Buckner., Mechanisms of impaired regulation by CD4(+)CD25(+)FOXP3(+) regulatory T cells in humanautoimmune diseases., Nature Reviews Immunology., (2010), pp. 849-859, vol. 10(12).

Clemente-Casares et al., Expanding antigen-specific regulatory networks to treat autoimmunity., Nature., (2016), pp. 434-440, vol. 530(7591).

Crawford et al., Specificity and detection of insulin-reactive CD4+ T cells in type 1 diabetes in the nonobese diabetic (NOD) mouse., Proc Natl Acad Sci U S A., (2011), pp. 16729-16734, vol. 108(40).

Dawson et al., Engineered Tolerance: Tailoring Development, Function, and Antigen-Specificity of Regulatory T Cells., Frontiers in Immunology., (2017), vol. 8:1460.

Elessawy et al., Type 1 diabetes and T regulatory cells., Pharmacology Research., (2015), pp. 22-30, vol. 98.

Grinberg-Bleyer et al., IL-2 reverses established type 1 diabetes in NOD mice by a local effect on pancreatic regulatory T cells., Journal of Experimental Medicine., (2010), pp. 1871-1878, vol. 207(9).

Jhunjhunwala et al., Delivery of rapamycin to dendritic cells using degradable microparticles., Journal of Control Release (2009), pp. 191-197, vol. 133(3).

Klatzmann et al., The promise of low-dose interleukin-2 therapy for autoimmune and inflammatory diseases., Nature Reviews Immunology., (2015), pp. 283-294, vol. 15(5).

Kuziel et al., Unexpected effects of the IL-2 receptor alpha subunit on high affinity IL-2 receptor assembly and function detected with a mutant IL-2 analog., Journal of Immunology., (1993), pp. 3357-3365, vol. 150(8).

Lee et al., Attenuation of donor-reactive T cells allows effective control of allograft rejection using regulatory T cell therapy, American Journal of Transplantation (2014), pp. 27-38, vol. 14(1).

Li et al., Suppression of ongoing T cell-mediated autoimmunity by peptide-MHC class II dimer vaccination., Journal of Immunology., (2009), pp. 4809-4816, vol. 183(7).

Liao et al., Interleukin-2 at the crossroads of effector responses, tolerance, and immunotherapy., Immunity., (2013), pp. 13-25, vol. 38(1).

Lin et al., Reversal of type 1 diabetes by a new MHC II-peptide chimera: "Single-epitope-mediated suppression" to stabilize a polyclonal autoimmune T-cell process., European Journal of Immunology., (2010), pp. 2277-2288, vol. 40(8).

Liu et al., Expansion of regulatory T cells via IL-2/anti-IL-2 mAb complexes suppresses experimental myasthenia., European Journal of Immunology., (2010), pp. 1577-1589, vol. 40(6).

Maahs et al., Mortality and renal disease in type 1 diabetes mellitus—progress made,more to be done., The Journal of Clinical Endocrinology & Metabolism., (2006), pp. 3757-3759, vol. 91(10).

Malek., The Biology of Interleukin-2., Annual Review of Immunology., (2008), pp. 453-479, vol. 26(1).

Marek-Trzonkowska et al., Administration of CD4+CD25highCD127- regulatory T cells preserves ß-cell function in type 1 diabetes in children., Diabetes Care., (2012), pp. 1817-1820, vol. 35(9).

Meyer et al., Biodegradable Nanoellipsoidal Artificial Antigen Presenting Cells for Antigen Specific T-Cell Activation., Small., (2015), pp. 1519-1525, vol. 11(13).

Murray., The JAK-STAT signaling pathway: input and output integration., Journal of Immunology., (2007), pp. 2623-2629, vol. 178(5).

Oelke et al., Ex vivo induction and expansion of antigen-specific cytotoxic T cells by HLA-Ig-coated artificial antigen-presenting cells., Nature Medicine., (2003), pp. 619-624, vol. 9(5).

Pasche et al., Immunocytokines: a novel class of potent armed antibodies., Drug Discovery Today., (2012), pp. 583-590, vol. 17(11-12).

Patterson et al., Diabetes in the young—a global view and worldwide estimates of numbers of children with type 1 diabetes., Diabetes Research and Clinical Practice., (2014), pp. 161-175, vol. 103(2).

Raimondi et al., Mammalian target of rapamycin inhibition and alloantigen-specific regulatory T cells synergize to promote long-term graft survival in immunocompetent recipients., Journal of Immunology., (2010), pp. 624-636, vol. 184(2).

Ring et al., Mechanistic and structural insight into the functional dichotomy between IL-2 and IL-15., Nature Immunology., (2012), pp. 1187-1195, vol. 13(12).

Roncarolo et al., Regulatory T-cell immunotherapy for tolerance to self antigens and alloantigens in humans., Nature Reviews Immunology., (2007), pp. 585-598, vol. 7(8).

Rossjohn et al., T Cell Antigen Receptor Recognition of Antigen-Presenting Molecules., Annual Review of Immunology., (2015), pp. 169-200, vol. 33(1).

Spangler et al., Antibodies to Interleukin-2 Elicit Selective T Cell Subset Potentiation through Distinct Conformational Mechanisms., Immunity., (2015), pp. 815-825, vol. 42(5).

Spangler et al., Engineering a Single-Agent Cytokine/Antibody Fusion That Selectively Expands Regulatory T Cells for Autoimmune Disease Therapy., Journal of Immunology., (2018), pp. 2094-2106, vol. 201(7).

Sunshine et al., Particle shape dependence of CD8+ T cell activation by artificial Antigen Presenting Cells., Biomaterials., (2014), pp. 269-277, vol. 35(1).

Tang et al., Central role of defective interleukin-2 production in the triggering of islet autoimmune destruction.,Immunity., (2008), pp. 687-697, vol. 28(5).

Tang et al., Transplant trials with Tregs: perils and promises., Journal of Clinical Investigation., (2017), pp. 2505-2512, vol. 127(7).

Trotta et al., A human anti-IL-2 antibody that potentiates regulatory T cells by a structure-based mechanism., Nature Medicine., (2018), pp. 1005-1014, vol. 24(7).

Turnquist et al., Rapamycin-Conditioned Dendritic Cells are Poor Stimulators of Allogeneic CD4+ T Cells, but Enrich for Antigen-Specific Foxp3+ T Regulatory Cells and Promote Organ Transplant Tolerance., Journal of Immunology., (2007), pp. 7018-7031, vol. 178(11).

Ugel et al., In vivo Administration of Artificial Antigen-Presenting Cells Activates Low-Avidity T Cells for Treatment of Cancer., Cancer Research., (2009), pp. 9376-9384, vol. 69(24).

Walker., Regulatory T cells overturned: the effectors fight back., Immunology., (2009), pp. 466-474, vol. 126(4).

Wang et al., Structure of the quaternary complex of interleukin-2 with its alpha, beta, and gammac receptors., Science., (2005), pp. 1159-1163, vol. 310(5751).

Webster et al., In vivo expansion of T reg cells with IL-2-mAb complexes: induction of resistance to EAE and long-term acceptance of islet allografts without immunosuppression., Journal of Experimental Medicine., (2009), pp. 751-760, vol. 206(4).

Wesley et al., Cellular Requirements for Diabetes Induction in DO11.10xRIPmOVA Mice., Journal of Immunology., (2010), pp. 4760-4768, vol. 185(8).

Writing Team for The Diabetes Control and Complications Trial/Epidemiology of Diabetes Interventions and Complications Research Group., Sustained effect of intensive treatment of type 1 diabetes mellitus on development and progression of diabetic nephropathy: the Epidemiology of Diabetes Interventions and Complications (EDIC) study., JAMA., (2003), pp. 2159-2167, vol. 290(16).

Yodoi et al., TCGF (IL 2)-receptor inducing factor(s). I. Regulation of IL 2 receptor on a natural killer-like cell line(YT cells)., Journal of Immunology., (1985), pp. 1623-1630, vol. 134(3).

You et al., Type 1 diabetes prevalence increasing globally and regionally: the role of natural selection and life expectancy at birth., BMJ Open Diabetes Research and Care., (2016), vol. 4(1):e000161.

Extended European Search Report for 20801487.8, mailed Apr. 6, 2023, 14 pages.

Ben-Akiva Elana et al: "Polymeric micro- and nanoparticles for immune modulation", Biomaterials Science, vol. 7, No. 1, Nov. 1, 2018 (Nov. 1, 2018), pp. 14-30.

(56) References Cited

OTHER PUBLICATIONS

Horwitz David A. et al: "Suppression of Murine Lupus by CD4+ and CD8+ Treg Cells Induced by T Cell-Targeted Nanoparticles Loaded With Interleukin-2 and Transforming Growth Factor [beta]", Arthritis & Rheumatology, vol. 71, No. 4, Mar. 5, 2019 (Mar. 5, 2019), pp. 632-640.

Little, S. R. et al.: "From The Cover: Poly-[beta] amino ester-containing microparticles enhance the activity of nonviral genetic vaccines", Proceedings of The National Academy of Sciences, vol. 101, No. 26, Jun. 29, 2004 (Jun. 29, 2004), pp. 9534-9539.

Pei Weiya et al: "Direct modulation of myelin-autoreactive CD4+ and CD8+ T cells in EAE mice by a tolerogenic nanoparticle co-carrying myelin peptide-loaded major histocompatibility complexes, CD47 and multiple regulatory molecules", International Journal of Nanomedicine, vol. 13, Jun. 27, 2018 (Jun. 27, 2018), pp. 3731-3750.

Steenblock Erin R. et al: "An Artificial Antigen-presenting Cell with Paracrine Delivery of IL-2 Impacts the Magnitude and Direction of the T Cell Response", Journal of Biological Chemistry, vol. 286, No. 40, Aug. 17, 2011 (Aug. 17, 2011), pp. 34883-34892.

\* cited by examiner

Figure 6
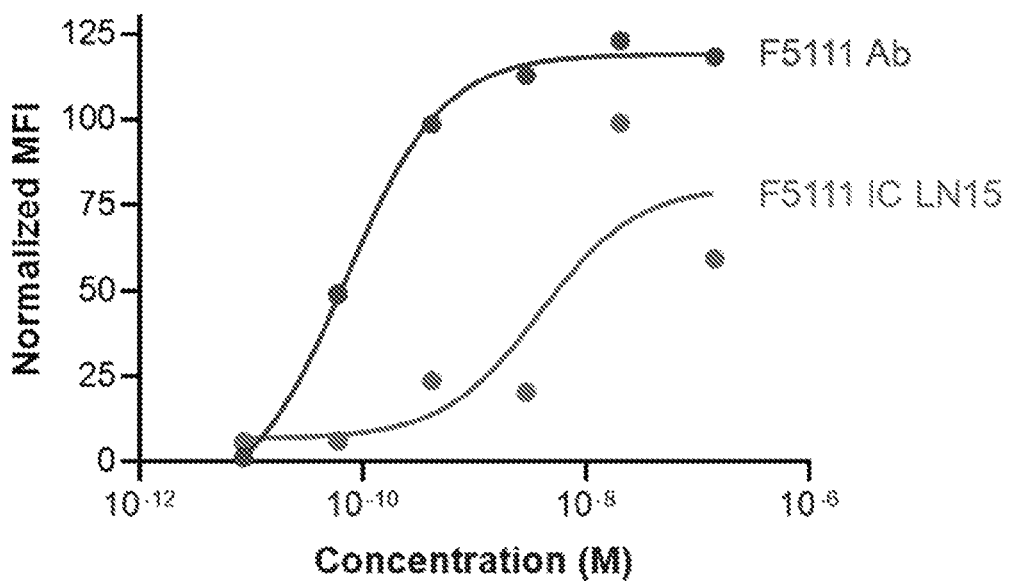
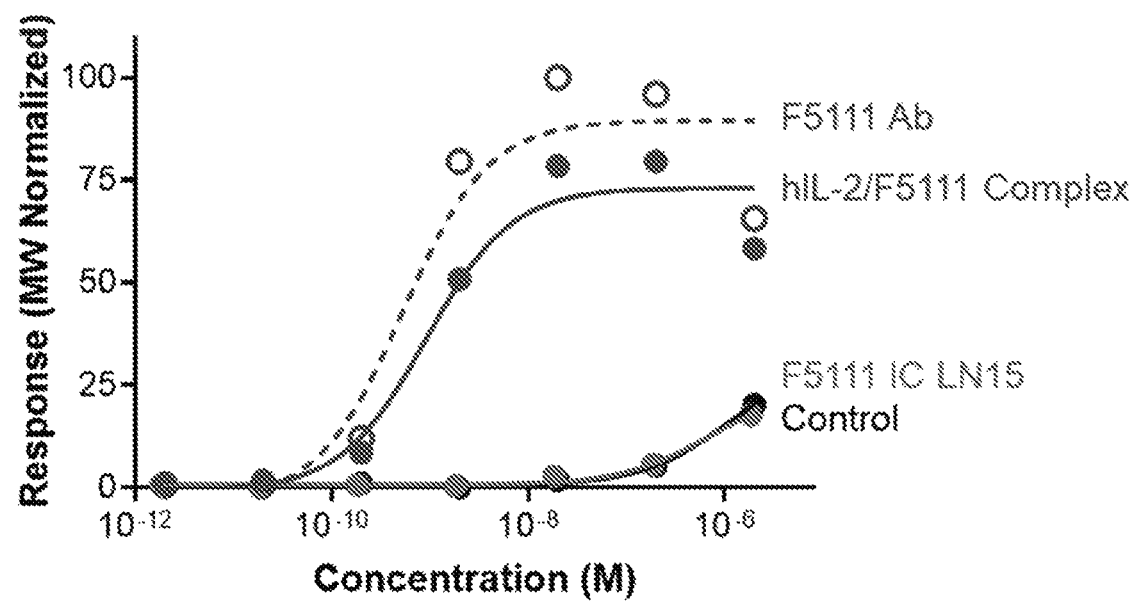

Figure 7
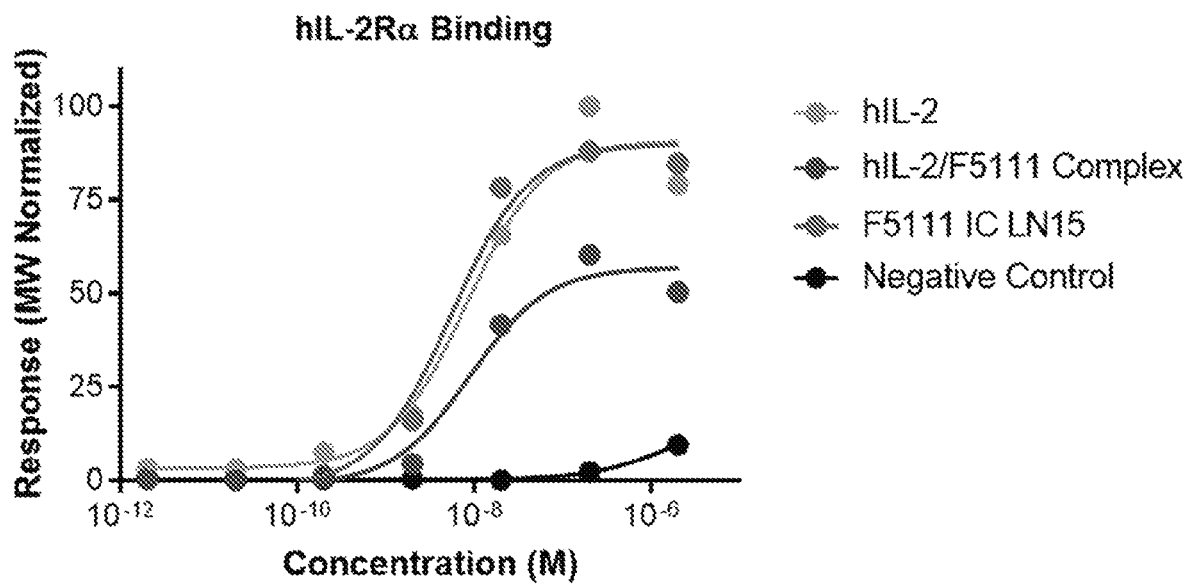
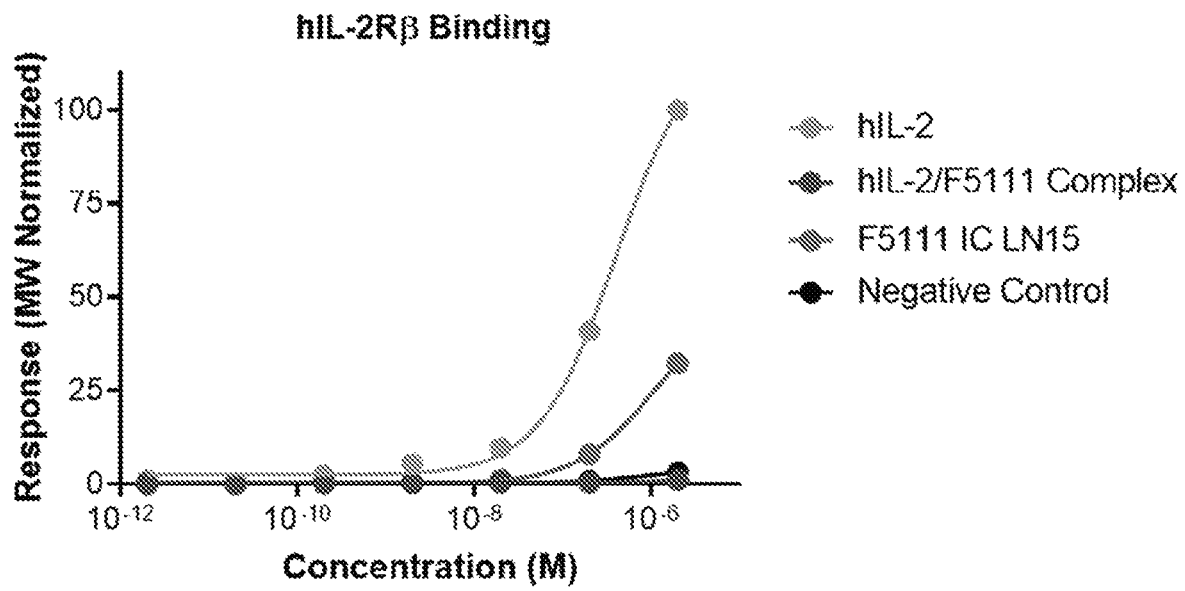

Figure 20

SEQUENCE LISTING

<160> NUMBER OF SEQ ID NOS: 11

<210> SEQ ID NO 1
<211> LENGTH: 121
<212> TYPE: PRT
<213> ORGANISM: Artificial Sequence
<220> FEATURE:
<223> OTHER INFORMATION: Synthetic

<400> SEQUENCE: 1

```
Gln Leu Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Thr Pro Thr Val Thr Gly Asp Trp Phe Asp Pro Trp Gly
            100                 105                 110

Arg Gly Thr Leu Val Thr Val Ser Ser
        115                 120
```

<210> SEQ ID NO 2
<211> LENGTH: 330
<212> TYPE: PRT
<213> ORGANISM: Artificial Sequence
<220> FEATURE:
<223> OTHER INFORMATION: Synthetic

<400> SEQUENCE: 2

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

```
                115                 120                 125
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 3
<211> LENGTH: 21
<212> TYPE: PRT
<213> ORGANISM: Artificial Sequence
<220> FEATURE:
<223> OTHER INFORMATION: Synthetic

<400> SEQUENCE: 3

Met Glu Thr Asp Thr Leu Leu Leu Trp Val Leu Leu Leu Trp Val Pro
1               5                   10                  15

Gly Ser Thr Gly Asp
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic

<400> SEQUENCE: 4

Met Arg Val Pro Ala Gln Leu Leu Gly Leu Leu Leu Leu Trp Leu Pro
1               5                   10                  15

Gly Ala Arg Cys
            20

<210> SEQ ID NO 5
<211> LENGTH: 472
<212> TYPE: PRT
<213> ORGANISM: Artificial Sequence
<220> FEATURE:
```

<223> OTHER INFORMATION: Synthetic

<400> SEQUENCE: 5

Met Glu Thr Asp Thr Leu Leu Leu Trp Val Leu Leu Leu Trp Val Pro
1               5                   10                  15

Gly Ser Thr Gly Asp Gln Leu Gln Leu Gln Glu Ser Gly Pro Gly Leu
            20                  25                  30

Val Lys Pro Ser Gln Thr Leu Ser Leu Thr Cys Thr Val Ser Gly Gly
        35                  40                  45

Ser Ile Ser Ser Gly Gly Tyr Tyr Trp Ser Trp Ile Arg Gln His Pro
    50                  55                  60

Gly Lys Gly Leu Glu Trp Ile Gly Tyr Ile Tyr Tyr Ser Gly Ser Thr
65                  70                  75                  80

Tyr Tyr Asn Pro Ser Leu Lys Ser Arg Val Thr Ile Ser Val Asp Thr
                85                  90                  95

Ser Lys Asn Gln Phe Ser Leu Lys Leu Ser Ser Val Thr Ala Ala Asp
            100                 105                 110

Thr Ala Val Tyr Tyr Cys Ala Arg Thr Pro Thr Val Thr Gly Asp Trp
        115                 120                 125

Phe Asp Pro Trp Gly Arg Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

```
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
            420                 425                 430
Ser Lys Leu Thr Val Asp Lys Ser Arg Trp Gln Gln Gly Asn Val Phe
        435                 440                 445
Ser Cys Ser Val Met His Glu Ala Leu His Asn His Tyr Thr Gln Lys
    450                 455                 460
Ser Leu Ser Leu Ser Pro Gly Lys
465                 470

<210> SEQ ID NO 6
<211> LENGTH: 133
<212> TYPE: PRT
<213> ORGANISM: Artificial Sequence
<220> FEATURE:
<223> OTHER INFORMATION: Synthetic

<400> SEQUENCE: 6

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr
        130

<210> SEQ ID NO 7
<211> LENGTH: 110
<212> TYPE: PRT
<213> ORGANISM: Artificial Sequence
<220> FEATURE:
<223> OTHER INFORMATION: Synthetic

<400> SEQUENCE: 7

Asn Phe Met Leu Thr Gln Pro His Ser Val Ser Glu Ser Pro Gly Lys
1               5                   10                  15
Thr Val Thr Ile Ser Cys Thr Arg Ser Ser Gly Ser Ile Ala Ser Asn
            20                  25                  30
Tyr Val Gln Trp Tyr Gln Gln Arg Pro Gly Ser Ser Pro Thr Thr Val
        35                  40                  45
Ile Tyr Glu Asp Asn Gln Arg Pro Ser Gly Val Pro Asp Arg Phe Ser
    50                  55                  60
Gly Ser Ile Asp Ser Ser Ser Asn Ser Ala Ser Leu Thr Ile Ser Gly
65                  70                  75                  80
Leu Lys Thr Glu Asp Glu Ala Asp Tyr Tyr Cys Gln Ser Tyr Asp Ser
                85                  90                  95
```

```
Ser Asn Val Val Phe Gly Gly Gly Thr Lys Leu Thr Val Leu
            100                 105                 110
```

<210> SEQ ID NO 8
<211> LENGTH: 106
<212> TYPE: PRT
<213> ORGANISM: Artificial Sequence
<220> FEATURE:
<223> OTHER INFORMATION: Synthetic

<400> SEQUENCE: 8

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 9
<211> LENGTH: 20
<212> TYPE: PRT
<213> ORGANISM: Artificial Sequence
<220> FEATURE:
<223> OTHER INFORMATION: Synthetic

<400> SEQUENCE: 9

```
Met Tyr Arg Met Gln Leu Leu Ser Cys Ile Ala Leu Ser Leu Ala Leu
1               5                   10                  15

Val Thr Asn Ser
            20
```

<210> SEQ ID NO 10
<211> LENGTH: 238
<212> TYPE: PRT
<213> ORGANISM: Artificial Sequence
<220> FEATURE:
<223> OTHER INFORMATION: Synthetic

<400> SEQUENCE: 10

```
Met Arg Val Pro Ala Gln Leu Leu Gly Leu Leu Leu Leu Trp Leu Pro
1               5                   10                  15

Gly Ala Arg Cys Gly Ser Asn Phe Met Leu Thr Gln Pro His Ser Val
            20                  25                  30

Ser Glu Ser Pro Gly Lys Thr Val Thr Ile Ser Cys Thr Arg Ser Ser
        35                  40                  45

Gly Ser Ile Ala Ser Asn Tyr Val Gln Trp Tyr Gln Gln Arg Pro Gly
    50                  55                  60

Ser Ser Pro Thr Thr Val Ile Tyr Glu Asp Asn Gln Arg Pro Ser Gly
65                  70                  75                  80

Val Pro Asp Arg Phe Ser Gly Ser Ile Asp Ser Ser Ser Asn Ser Ala
                85                  90                  95
```

```
Ser Leu Thr Ile Ser Gly Leu Lys Thr Glu Asp Glu Ala Asp Tyr Tyr
            100                 105                 110

Cys Gln Ser Tyr Asp Ser Ser Asn Val Val Phe Gly Gly Gly Thr Lys
        115                 120                 125

Leu Thr Val Leu Gly Gln Pro Lys Ala Ala Pro Ser Val Thr Leu Phe
    130                 135                 140

Pro Pro Ser Ser Glu Glu Leu Gln Ala Asn Lys Ala Thr Leu Val Cys
145                 150                 155                 160

Leu Ile Ser Asp Phe Tyr Pro Gly Ala Val Thr Val Ala Trp Lys Ala
                165                 170                 175

Asp Ser Ser Pro Val Lys Ala Gly Val Glu Thr Thr Thr Pro Ser Lys
            180                 185                 190

Gln Ser Asn Asn Lys Tyr Ala Ala Ser Ser Tyr Leu Ser Leu Thr Pro
        195                 200                 205

Glu Gln Trp Lys Ser His Arg Ser Tyr Ser Cys Gln Val Thr His Glu
    210                 215                 220

Gly Ser Thr Val Glu Lys Thr Val Ala Pro Thr Glu Cys Ser
225                 230                 235

<210> SEQ ID NO 11
<211> LENGTH: 384
<212> TYPE: PRT
<213> ORGANISM: Artificial Sequence
<220> FEATURE:
<223> OTHER INFORMATION: Synthetic

<400> SEQUENCE: 11

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Gly Gly Gly Ser Gly Gly
145                 150                 155                 160

Gly Gly Ser Gly Gly Gly Gly Ser Asn Phe Met Leu Thr Gln Pro His
                165                 170                 175

Ser Val Ser Glu Ser Pro Gly Lys Thr Val Thr Ile Ser Cys Thr Arg
            180                 185                 190

Ser Ser Gly Ser Ile Ala Ser Asn Tyr Val Gln Trp Tyr Gln Gln Arg
        195                 200                 205

Pro Gly Ser Ser Pro Thr Thr Val Ile Tyr Glu Asp Asn Gln Arg Pro
    210                 215                 220
```

-continued

```
Ser Gly Val Pro Asp Arg Phe Ser Gly Ser Ile Asp Ser Ser Ser Asn
225                 230                 235                 240

Ser Ala Ser Leu Thr Ile Ser Gly Leu Lys Thr Glu Asp Glu Ala Asp
                245                 250                 255

Tyr Tyr Cys Gln Ser Tyr Asp Ser Ser Asn Val Val Phe Gly Gly Gly
            260                 265                 270

Thr Lys Leu Thr Val Leu Gly Gln Pro Lys Ala Ala Pro Ser Val Thr
        275                 280                 285

Leu Phe Pro Pro Ser Ser Glu Glu Leu Gln Ala Asn Lys Ala Thr Leu
    290                 295                 300

Val Cys Leu Ile Ser Asp Phe Tyr Pro Gly Ala Val Thr Val Ala Trp
305                 310                 315                 320

Lys Ala Asp Ser Ser Pro Val Lys Ala Gly Val Glu Thr Thr Thr Pro
                325                 330                 335

Ser Lys Gln Ser Asn Asn Lys Tyr Ala Ala Ser Ser Tyr Leu Ser Leu
                340                 345                 350

Thr Pro Glu Gln Trp Lys Ser His Arg Ser Tyr Ser Cys Gln Val Thr
        355                 360                 365

His Glu Gly Ser Thr Val Glu Lys Thr Val Ala Pro Thr Glu Cys Ser
    370                 375                 380
```

TOLEROGENIC ARTIFICIAL ANTIGEN-PRESENTING CELLS

CROSS-REFERENCE TO RELATED APPLICATIONS

This application is a § 371 National Stage Entry of Int'l Pat. App. No. PCT/US2020/027989, filed on Apr. 13, 2020, which claims the benefit of U.S. Provisional Patent Application Nos. 62/832,957 and 62/916,404, filed Apr. 12, 2019, and Oct. 17, 2019, respectively, the contents of both of which are incorporated by reference herein.

STATEMENT REGARDING FEDERALLY-SPONSORED RESEARCH

This invention was made with Government support under W81XWH-18-1-0735 awarded by the Army Medical Research and Material Command, EB022148 awarded by the National Institutes of Health, and DGE1232825 awarded by the National Science Foundation. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 18,085 Byte ASCII (Text) file named "2020-04-13_38080-601_SQL_ST25.txt," created on Apr. 13, 2020.

BACKGROUND

Autoimmune diseases are often treated with immunosuppressants that weaken the entire immune system, leaving patients vulnerable to infection. An ideal autoimmune therapy establishes immune tolerance to the specific self-antigen(s) recognized by the host immune system, while the rest of the immune system remains intact. See Sabatos-Peyton C. et al. *Curr. Opin. Immunol.* 2010. One strategy for establishing antigen-specific immune tolerance is targeting regulatory T cells ($T_{Regs}$), which maintain immune homeostasis and dampen immune responses to self-antigens through a variety of mechanisms and are fundamental controllers of the destructive arm of the immune system. Vignali D, et al. *Nat Rev Immunol.* 2008.

Regulatory T ($T_{Reg}$) cells comprise a heterogeneous subset of lymphocytes that inhibit effector T cell activity to orchestrate immune tolerance. Recent work shows that adoptive transfer of TReg cells can suppress effector T cells to ameliorate autoimmune diseases (ElEssawy, B. and Li, X. C., *Pharmacol Res.*, 98 (Supplement C): 22-30 (2015); Battaglia, M., and Roncarolo, M. G., *Semin Immunol.*, 23(3): 182-194 (2011); Marek-Trzonkowska et al., *Diabetes Care*, 35(9): 1817-1820 (2012)). Unfortunately, logistical and manufacturing issues, coupled with concerns about the safety and stability of ex vivo-expanded $T_{Reg}$ cells, impede widespread adoption of this approach (ElEssawy, supra; and Roncarolo, supra). Moreover, expansion of antigen-specific $T_{Reg}$ cells, which are significantly more effective in suppressing effector T cell activity than polyclonal TReg cells, is challenging (Lee et al., *Am J Transplant Off J Am Soc Transplant Am Soc Transpl Surg.*, 14 (1): 27-38 (2014); and Tang, Q. and Vincenti, F., *J Clin Invest.*, 127(7): 2505-2512 (2017)).

BRIEF SUMMARY OF THE INVENTION

The disclosure provides biodegradable particle comprising a polyester or polyester blend, a first protein that binds to an immune cell, and a second protein that promotes proliferation and/or activation of immune cells, and a third soluble protein or small molecule encapsulated within the particle, wherein (i) the first protein is attached to a surface of the particle or to a coating on the surface thereof, and (ii) the second protein is a fusion protein comprising at least a portion of an antibody and at least a portion of a cytokine and is either attached to a surface of the particle or to a coating on the surface thereof or encapsulated within the particle. The disclosure also provides methods for treating a disease or condition in a subject (e.g., an autoimmune disease) comprising administering the aforementioned biodegradable particle to the subject.

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWING(S)

The patent or application file contains at least one drawing executed in color. Copies of this patent or patent application publication with color drawings will be provided by the Office upon request and payment of the necessary fee.

Having thus described the presently disclosed subject matter in general terms, reference will now be made to the accompanying Figures, which are not necessarily drawn to scale, and wherein:

Figure 4:
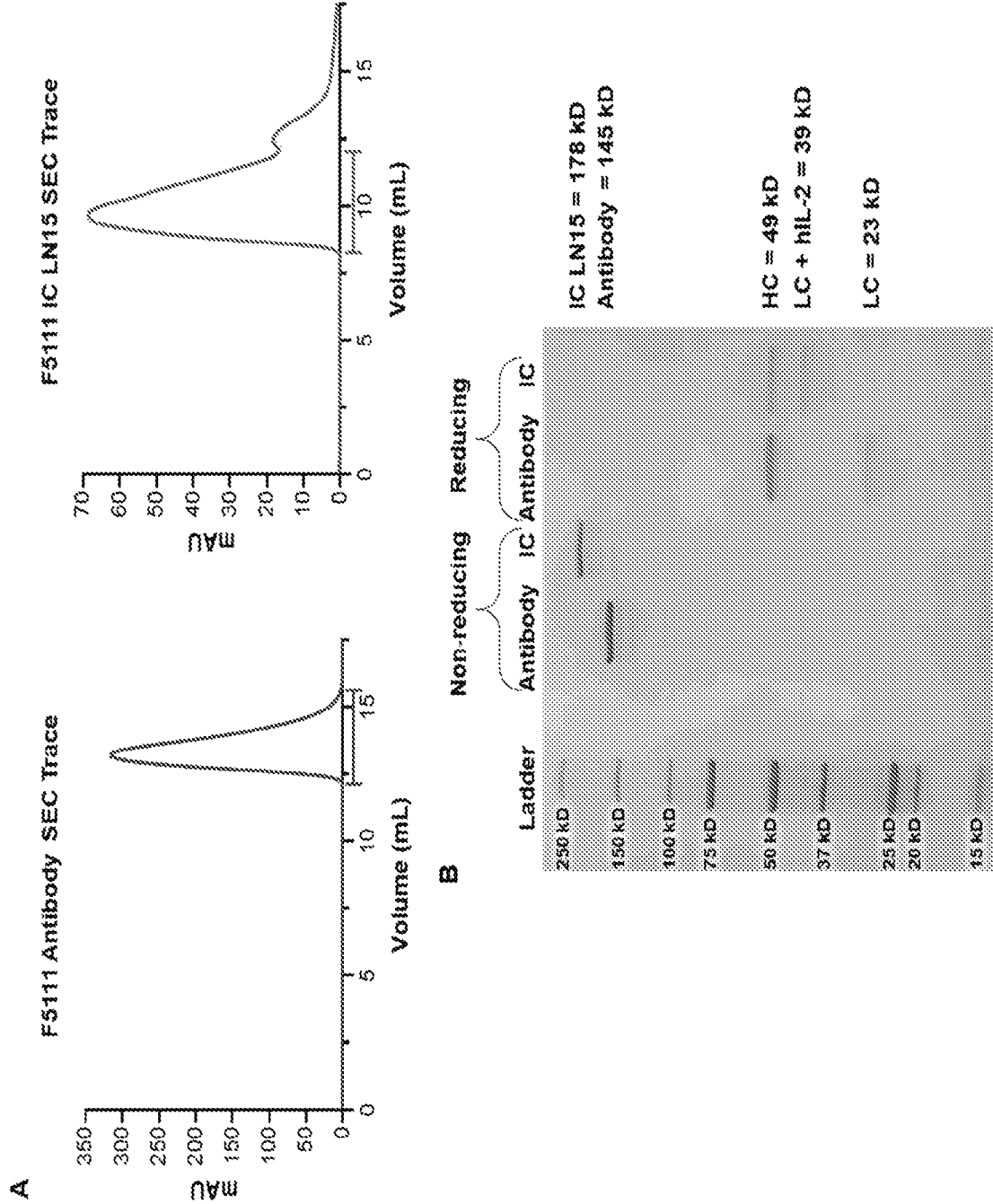

FIG. 4A is a graph illustrating FPLC traces of recombinant F5111 antibody (left panel) and F5111 immunocytokine (IC) LN15 (right panel). LN15 refers to a 15-amino acid linker between the C-terminus of human IL-2 and the N-terminus of the F5111 antibody light chain. Pooled fractions are indicated by a solid line. FIG. 4B is an image of non-reducing and reducing SDS-PAGE analyses of purified F5111 antibody and F5111 IC LN15.

Figure 5:
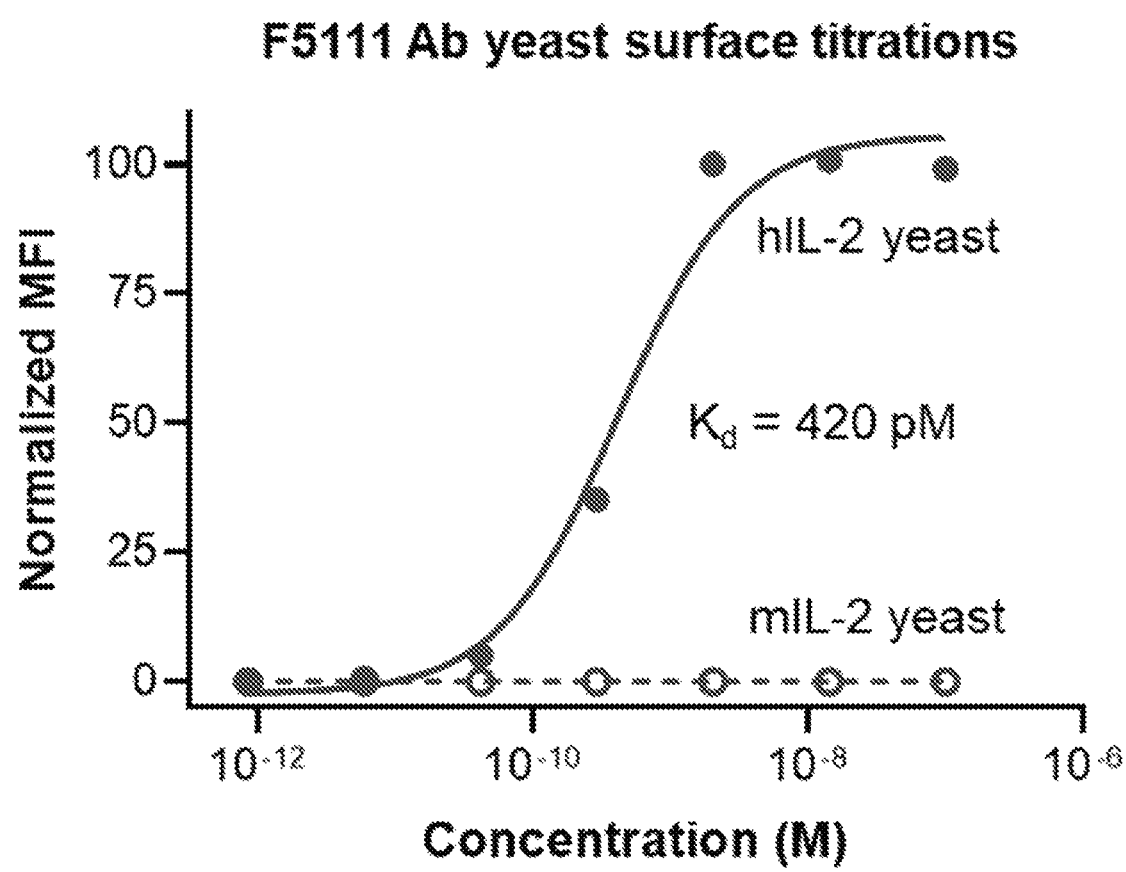

FIG. 5 is a graph showing that F5111 antibody binds human but not mouse IL-2 cytokine. Yeast surface binding of F5111 antibody to human IL-2 (hIL-2, solid line) or mouse IL-2 (mIL-2, dashed line) is shown, as measured by flow cytometry.

FIG. 6A is a graph depicting binding of the F5111 antibody and IC to yeast surface-displayed hIL-2, as measured by flow cytometry. FIG. 6B is a graph showing binding of purified F5111 antibody, hIL-2/F5111 complex, and F5111 IC LN15 to immobilized hIL-2, as measured by bio-layer interferometry.

FIG. 7A is a graph showing bio-layer interferometry binding titrations of hIL-2, hIL-2/F5111 complex, and F5111 IC LN15 against immobilized IL-2Rα. FIG. 7B is a graph showing bio-layer interferometry binding titrations of hIL-2, hIL-2/F5111 complex, and F5111 IC LN15 against immobilized IL-2Rβ.

Figure 8:
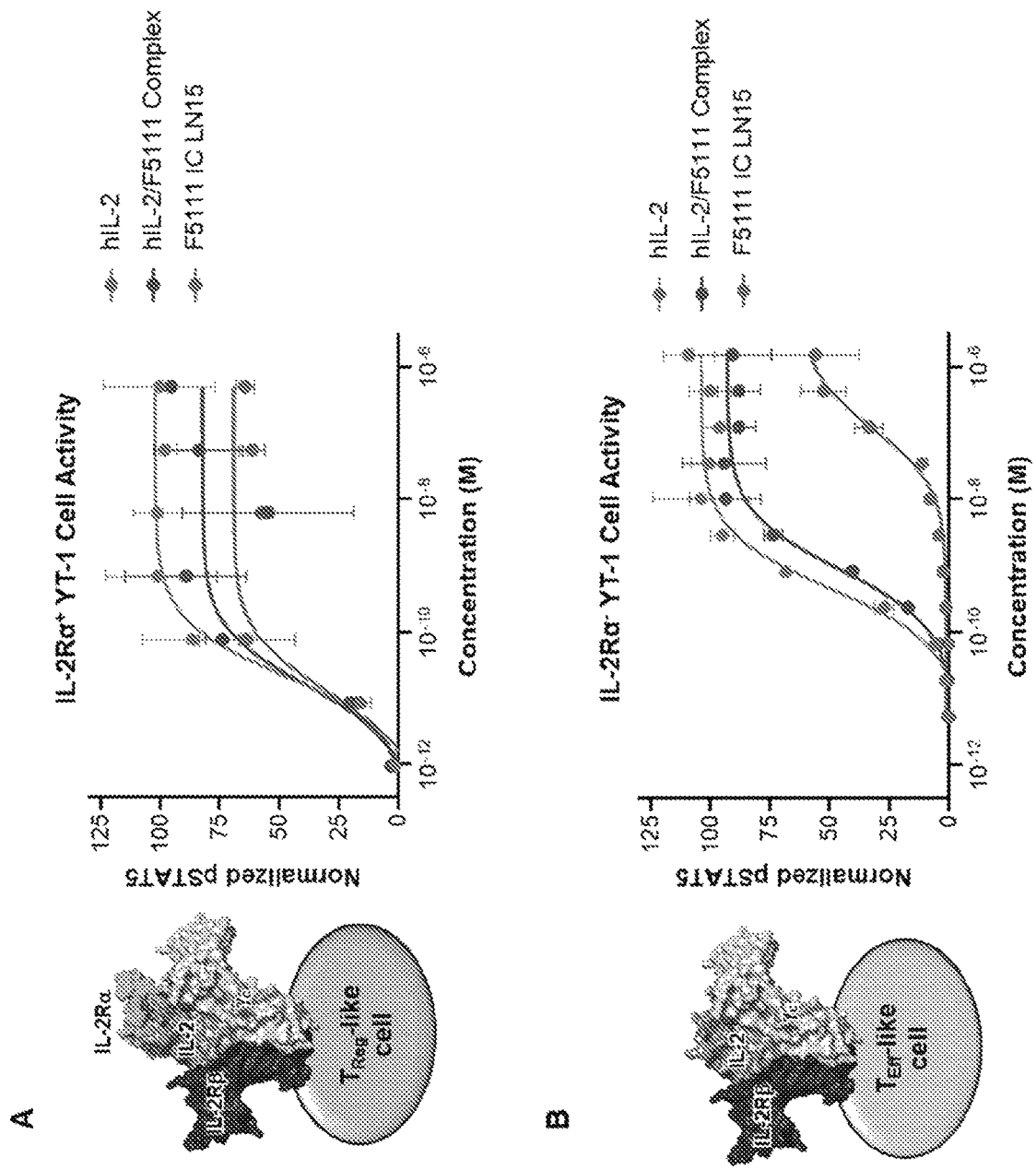

FIG. 8 includes schematics and graphs illustrating that F5111 IC LN15 selectively activates IL-2Rα+ cells. STAT5 activation in response to IL-2, IL-2/F5111 complex, or F5111 IC LN15 on YT-1 human natural killer (NK) cells with (FIG. 8A) or without (FIG. 8B) IL-2Rα is shown, as measured by flow cytometry.

Figure 9:
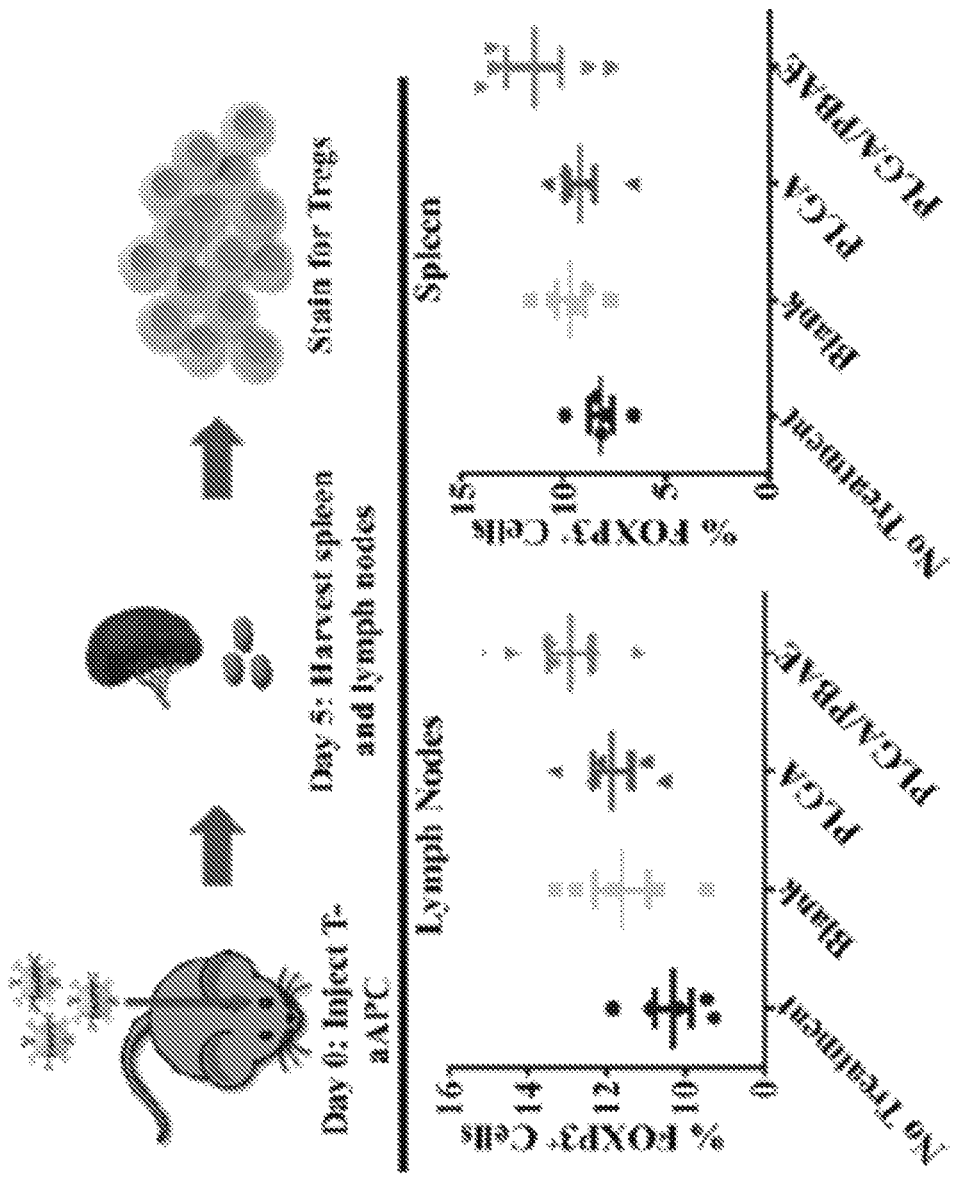

FIG. 9 includes a schematic and graphs illustrating that systemic injection of PLGA/PBAE aAPCs bearing anti-CD3 and anti-CD28 and encapsulating TGF-β into mice induced significantly more FOXP3+ $T_{Reg}$ cells in lymph nodes (FIG. 9A) and spleen (FIG. 9B) compared to controls.

Figure 10:
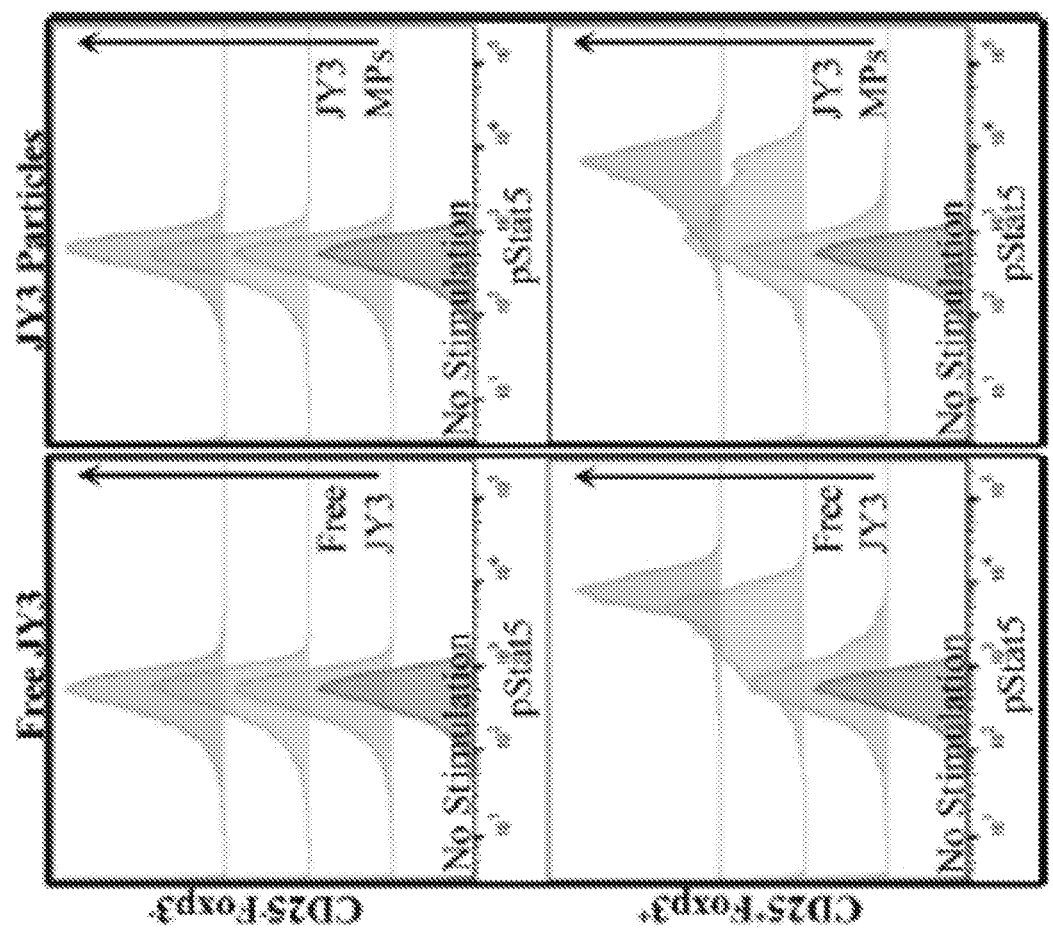

FIGS. 10A and 10B are graphs showing in vitro $T_{Reg}$-selective stimulation by IL-2/JES6-1 single chain IC (denoted JY3 or JY3 IC) microparticles (MPs) (. CD4+ T cells from NOD mice were stimulated with increasing concentrations of unconjugated JY3 IC (FIG. 10A) or JY3 IC conjugated to MPs (FIG. 10B). JY3 IC MPs selectively activated CD25+Foxp3+ $T_{Reg}$ cells with similar potency to unconjugated JY3 IC.

FIGS. 11A-11D are graphs showing that JY3 IC-coated MPs stimulate biased $T_{Reg}$ expansion. Shown is expansion of $T_{Reg}$ versus total CD4+ (FIG. 11A) or CD8+ (FIG. 11B) T cells in NOD mouse spleens after 4 daily intravenous (i.v.) injections of PBS or JY3 IC-coated MPs. Also shown is expansion of $T_{Reg}$ versus total CD4+ (FIG. 11C) or CD8+ (FIG. 11D) T cells in injected versus non-injected lymph nodes (LN) of NOD mice after 2 intranodal (i.n.) injections of PBS or JY3 IC-coated MPs. Statistical significance was assessed by two-tailed unpaired Student's t-test.

Figure 12:
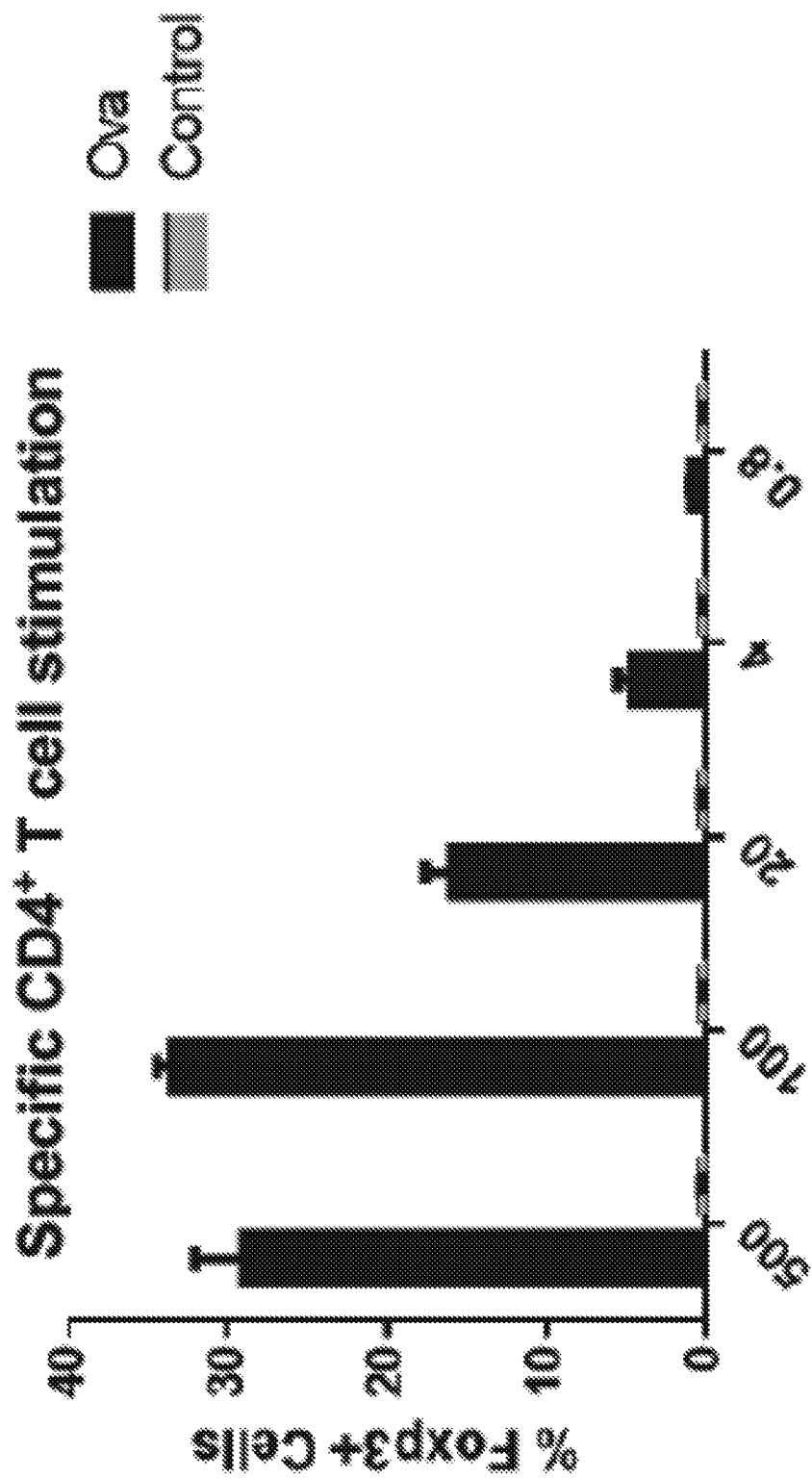

FIG. 12 is a graph illustrating antigen-specific $T_{Reg}$ cell stimulation using aAPCs. MPs surface-conjugated with ovalbumin (OVA) peptide-loaded MHC tetramers and anti-CD28 antibody induced OVA-specific $T_{Reg}$ cells from naïve OT-II CD4+ T cells, while MPs with a control tetramer did not induce $T_{Reg}$ cells. Titrated doses of MPs were incubated with naïve CD4+ T cells in the presence of IL-2 and TGF-β for 3 days, then stained for FOXP3 and analyzed using flow cytometry.

Figure 13:
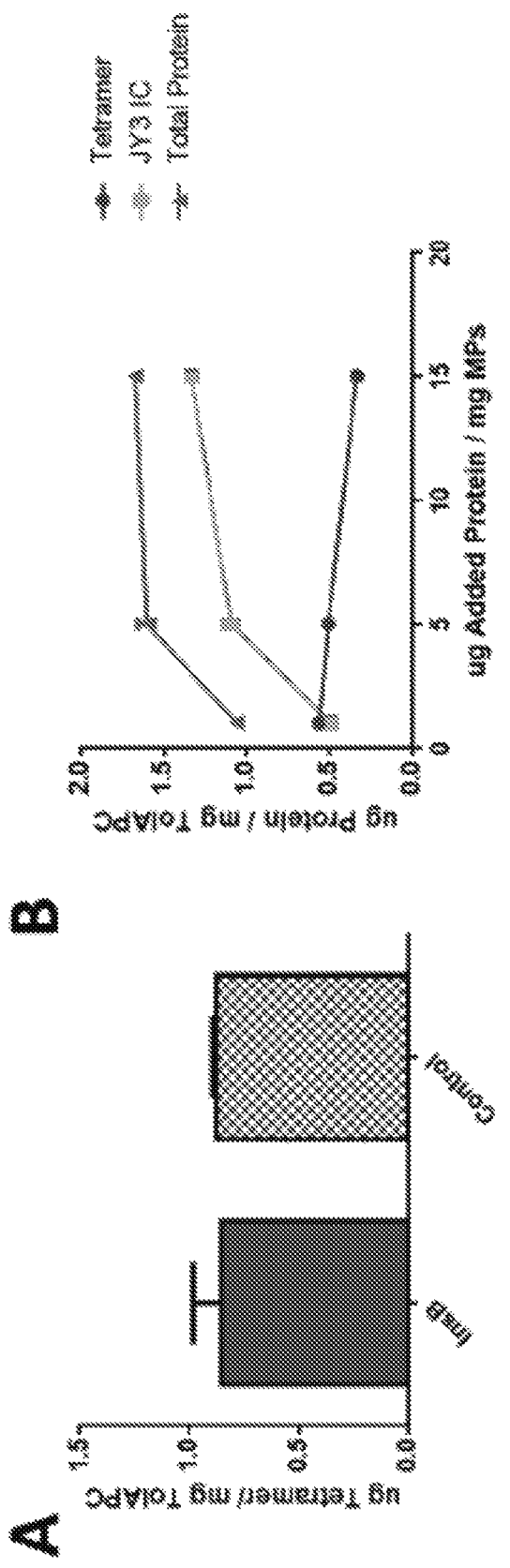

FIGS. 13A and 13B are graphs illustrating the protein conjugation efficiency of TolAPC. FIG. 13A is a graph showing conjugation of PLGA/PBAE MPs with the same amount of insulin B peptide (InsB) or control tetramer. Tetramer was conjugated to the surface of particles using EDC/NHS chemistry. FIG. 13B is a graph showing PLGA/PBAE particles conjugated with different amounts of fluorescently-labeled tetramer and JY3 IC.

Figure 14:
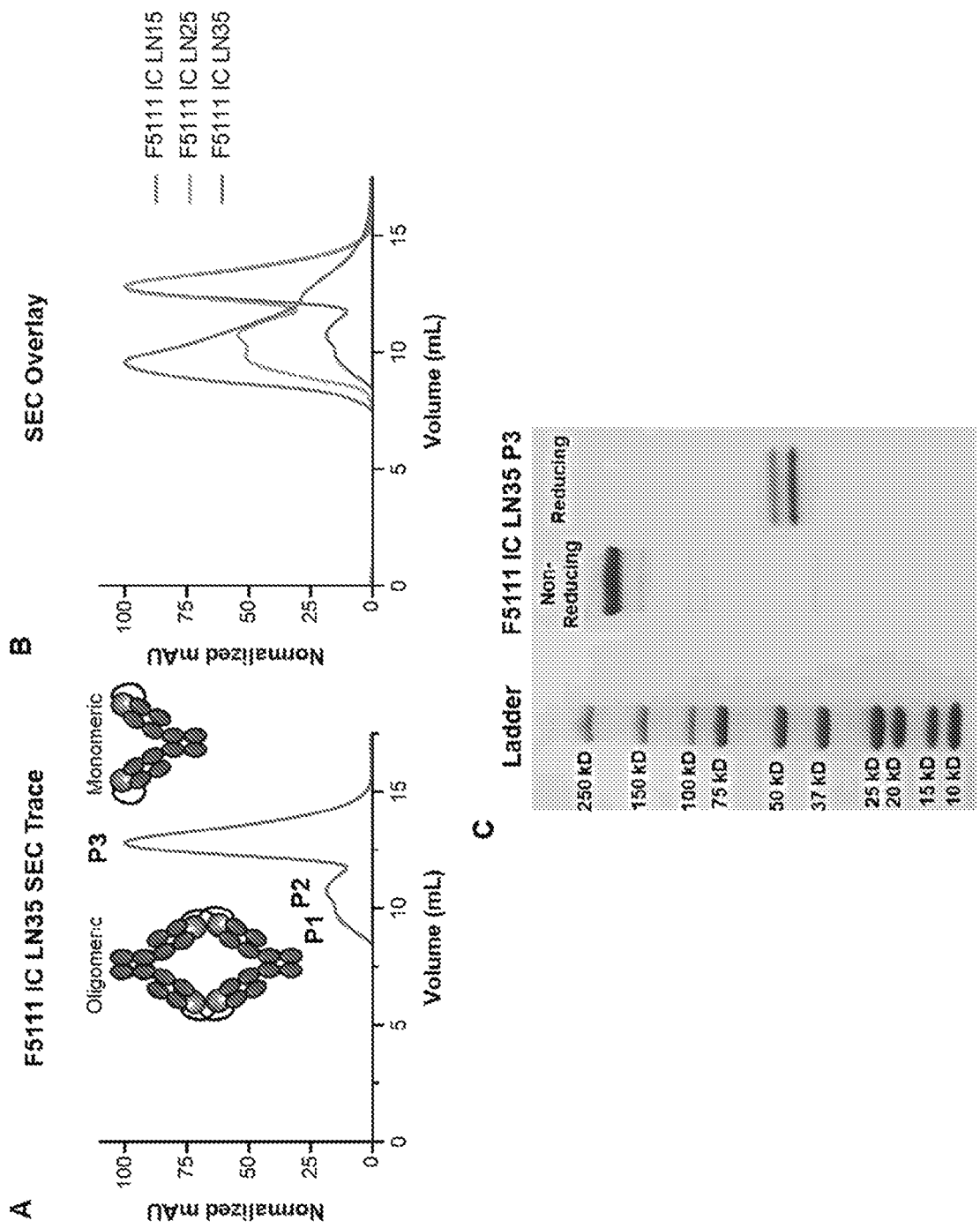

FIG. 14 shows that F5111 IC LN25 and LN35 were produced in HEK293 cells and purified using size exclusion chromatography (SEC). FIG. 14A is a graph showing the SEC trace for the F5111 IC LN35. It is expected that Peak 1 (P1) and Peak 2 (P2) contain higher order oligomeric structures, whereas Peak 3 (P3) contains the monomeric F5111 IC LN35. Therefore, P3 was used for all subsequent experiments, and F5111 IC LN25 and F5111 IC LN35 refer to the pooled P3 fraction unless otherwise specified. FIG. 14B is a graph showing SEC comparison of F5111 IC LN15, F5111 IC LN25, and F5111 IC LN35. FIG. 14C is an image of SDS-PAGE analysis of F5111 IC LN35 P3 under reducing and non-reducing conditions.

Figure 15:
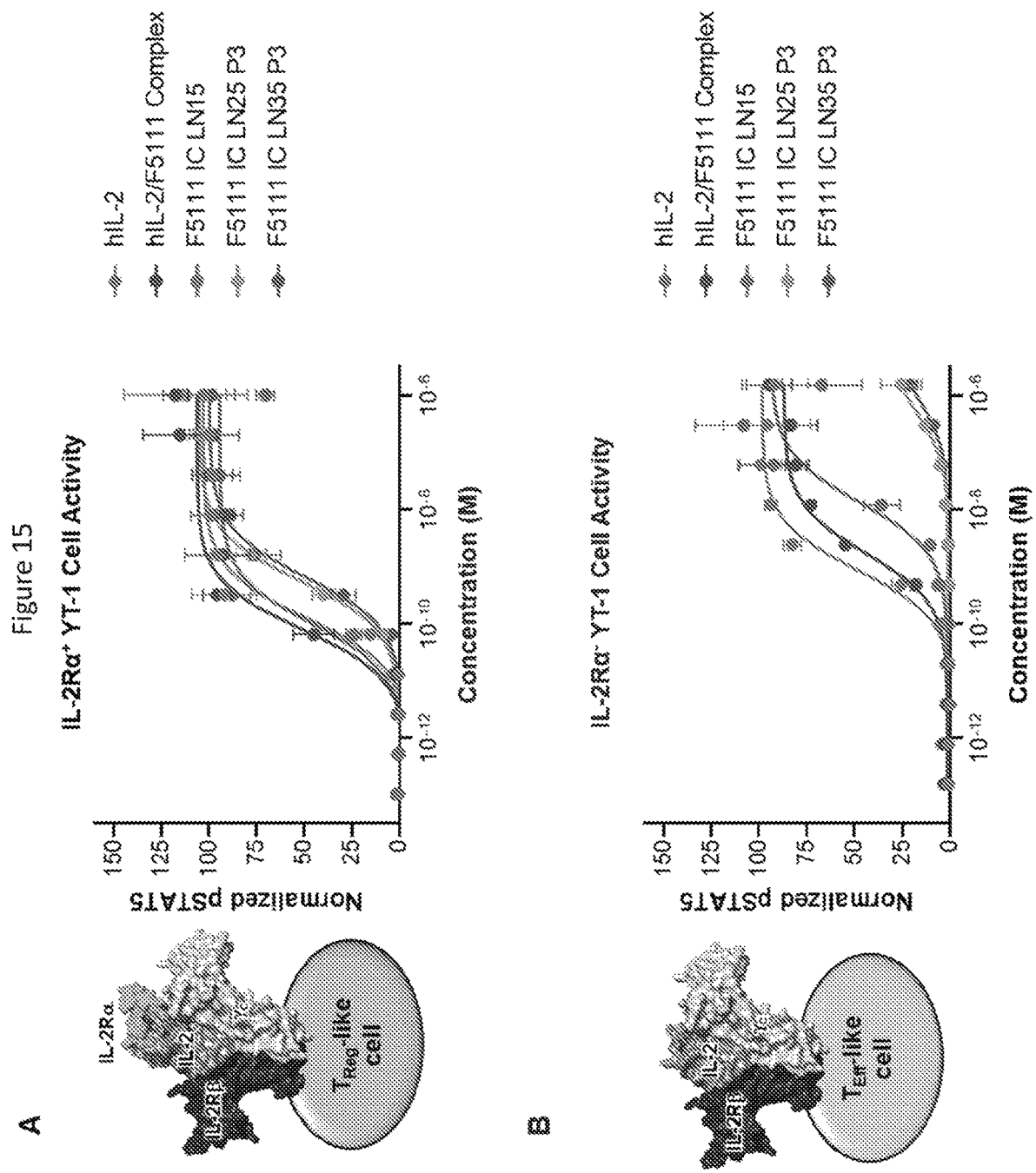

FIG. 15 shows STAT5 activation in response to various IL-2 treatments on IL-2Rα+ and IL-2Rα− YT-1 cells. STAT5 activation in response to IL-2, IL-2/F5111 complex, or F5111 IC variants on YT-1 cells with (FIG. 15A) or without (FIG. 15B) IL-2Rα is shown, as measured by flow cytometry.

Figure 16:
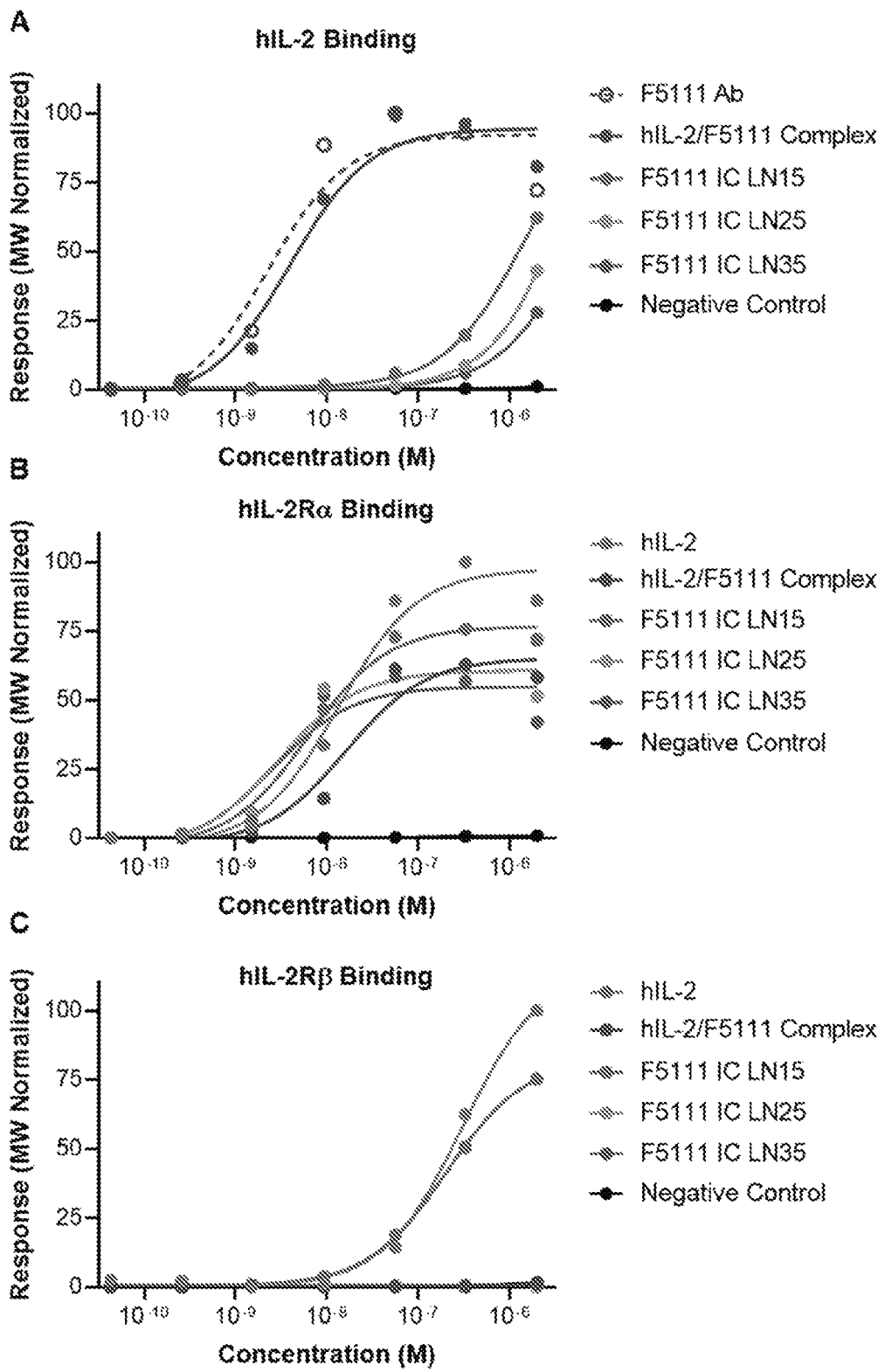

FIG. 16 shows binding of F5111 IC variants to hIL-2 and hIL-2 receptor subunits. FIG. 16A is a graph showing binding of purified F5111 antibody, F5111/hIL-2 complex, and F5111 IC variants to immobilized hIL-2, as measured by bio-layer interferometry. FIG. 16B illustrates binding of purified F5111 antibody, F5111/hIL-2 complex, and F5111 IC variants to immobilized hIL-2Rα, as measured by bio-layer interferometry. FIG. 16C illustrates binding of purified F5111 antibody, F5111/hIL-2 complex, and F5111 IC variants to immobilized hIL-2Rβ, as measured by bio-layer interferometry.

Figure 17:
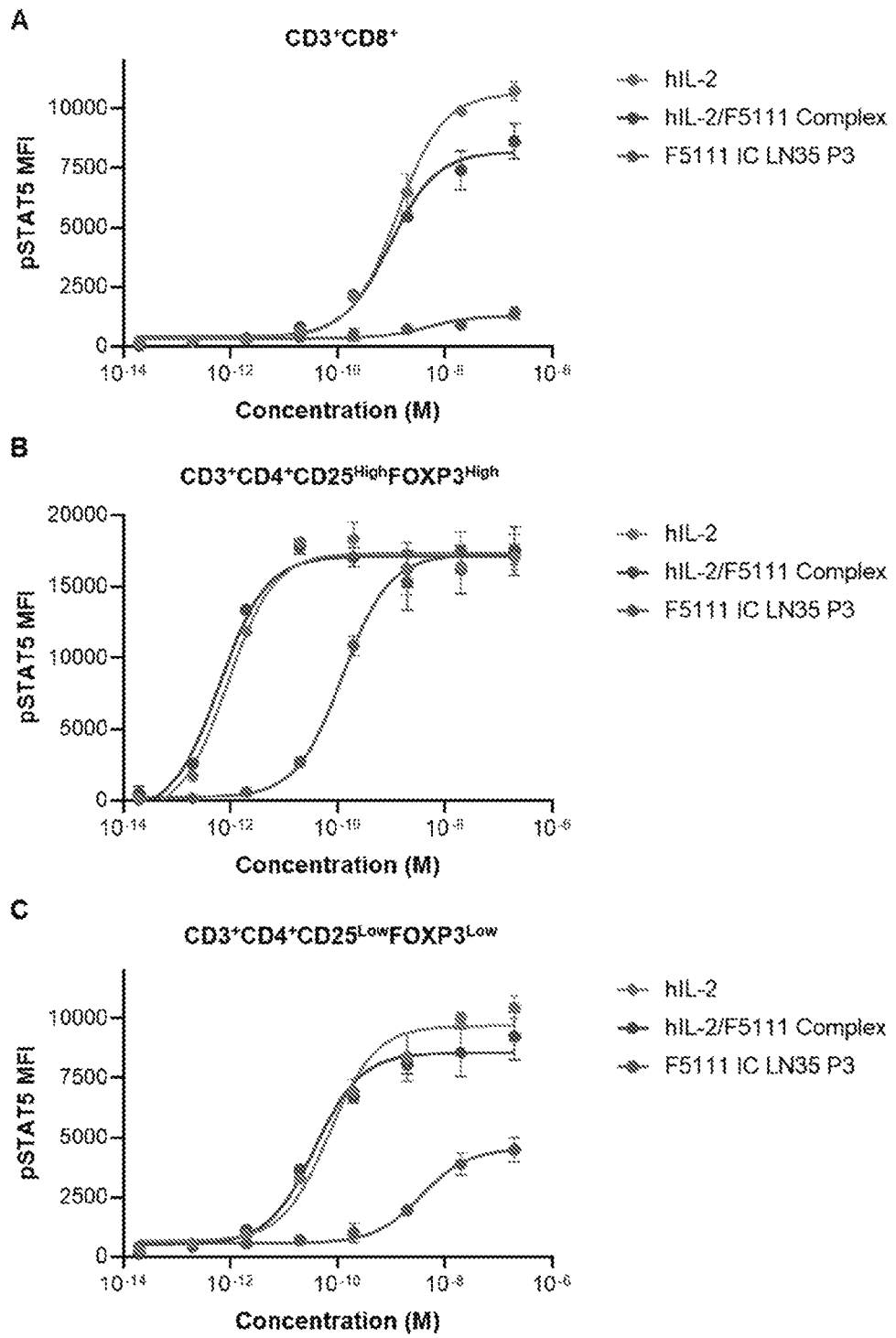

FIG. 17 shows STAT5 activation in response to hIL-2, hIL-2/F5111 complex, and F5111 IC variants on different immune cell subsets of human PBMCs isolated from whole blood. FIG. 17A shows STAT5 activation on CD3+ CD8+ cells (CD8+ effector T cells), FIG. 17B shows STAT5 activation on the CD3+CD4+CD25$^{High}$FOXP3$^{High}$ cells ($T_{Reg}$ cells), and FIG. 17C shows STAT5 activation on the CD3+CD4+CD25$^{Low}$FOXP3$^{Low}$ cells (CD4+ effector T cells).

Figure 18:
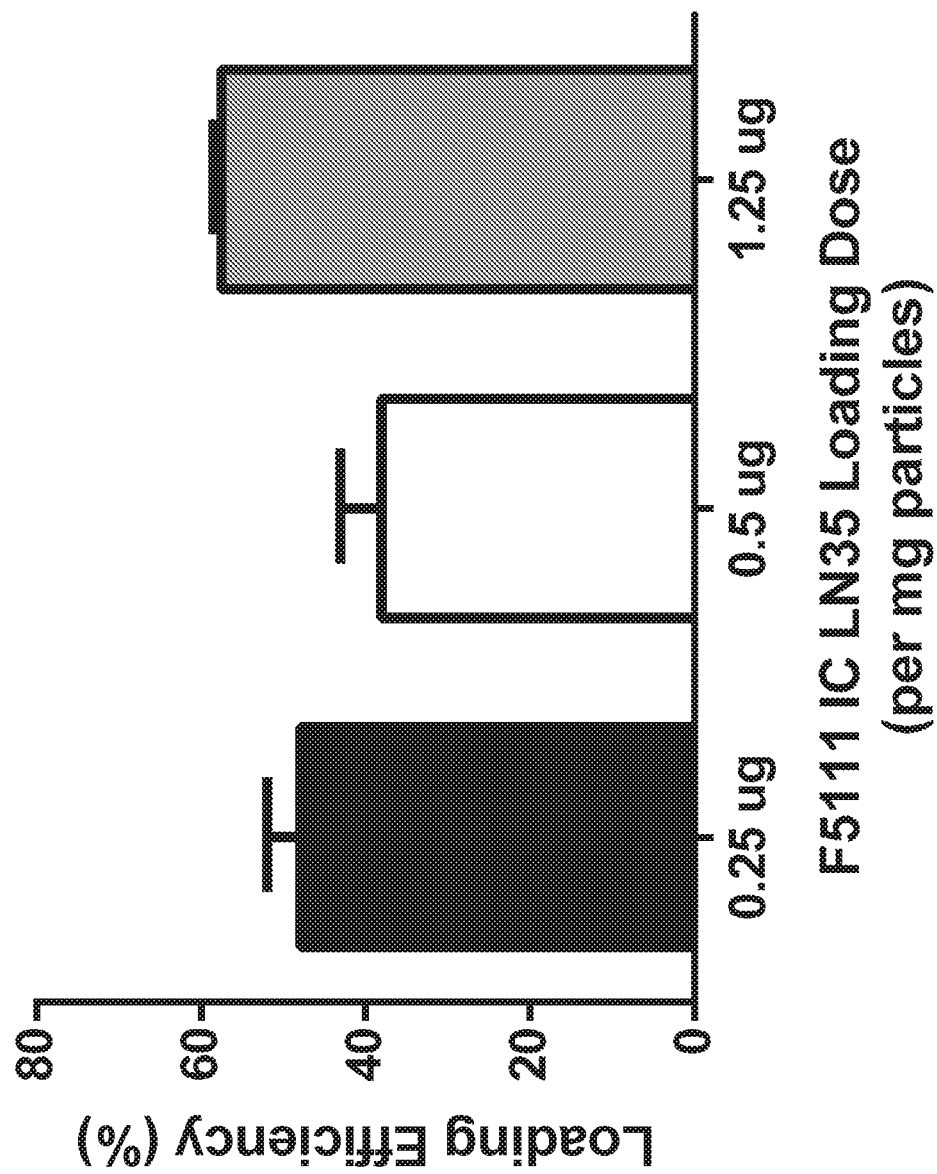

FIG. 18 is a graph illustrating the efficiency of various F5111 IC LN35 loading doses into PLGA particles, as measured by a BCA protein assay. Maximum encapsulation efficiency was observed for a loading dose of 1.25 µg F5111 IC LN35 per mg PLGA.

Figure 19:
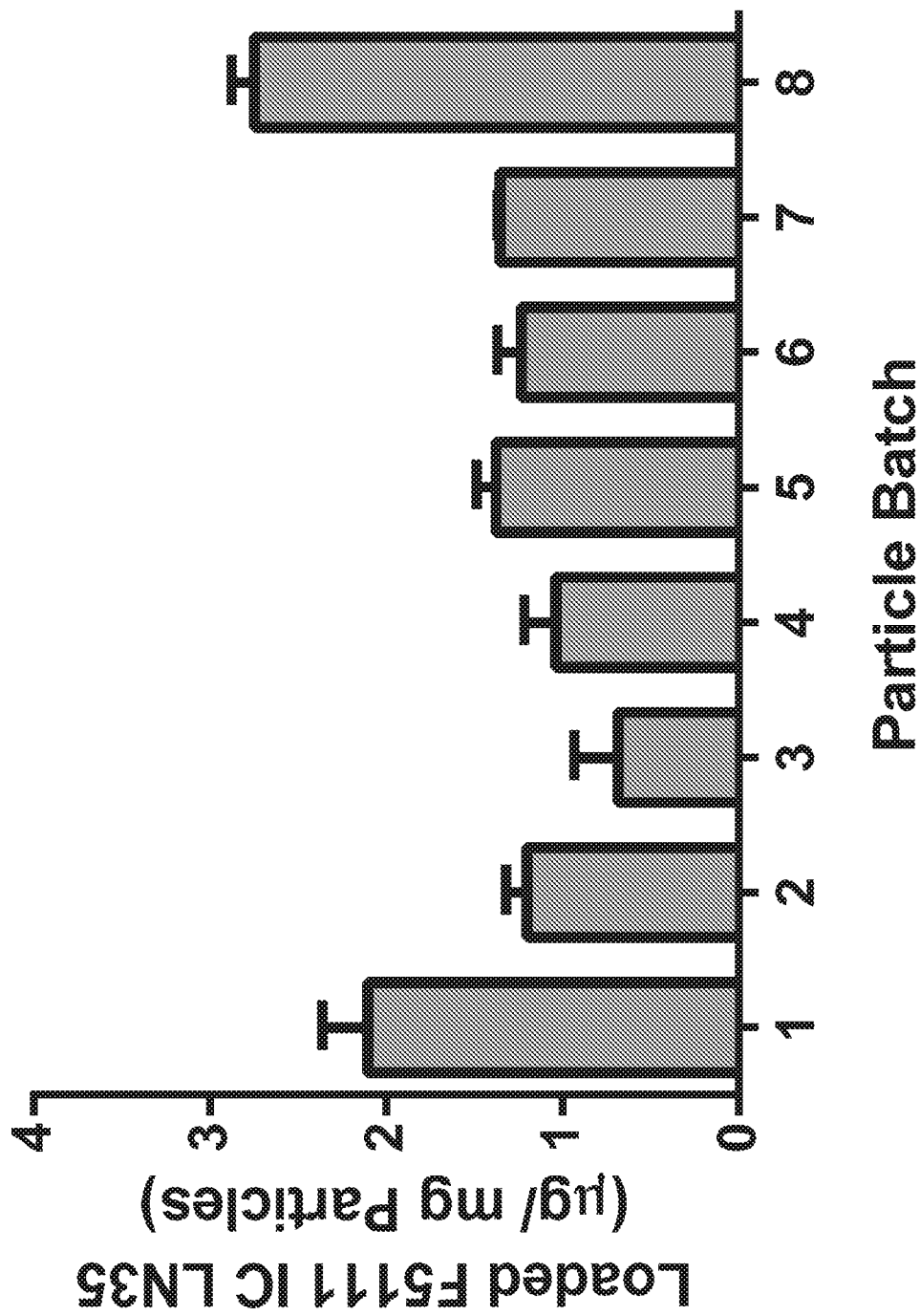

FIG. 19 is a graph showing F5111 IC LN35 loading across a variety of PLGA particle synthesis parameters, as measured by a BCA protein quantification assay. 1.25 µg F5111 IC LN35 per mg PLGA was added during particle synthesis. Maximum loading efficiency was achieved with Batch #8.

Figure 20:
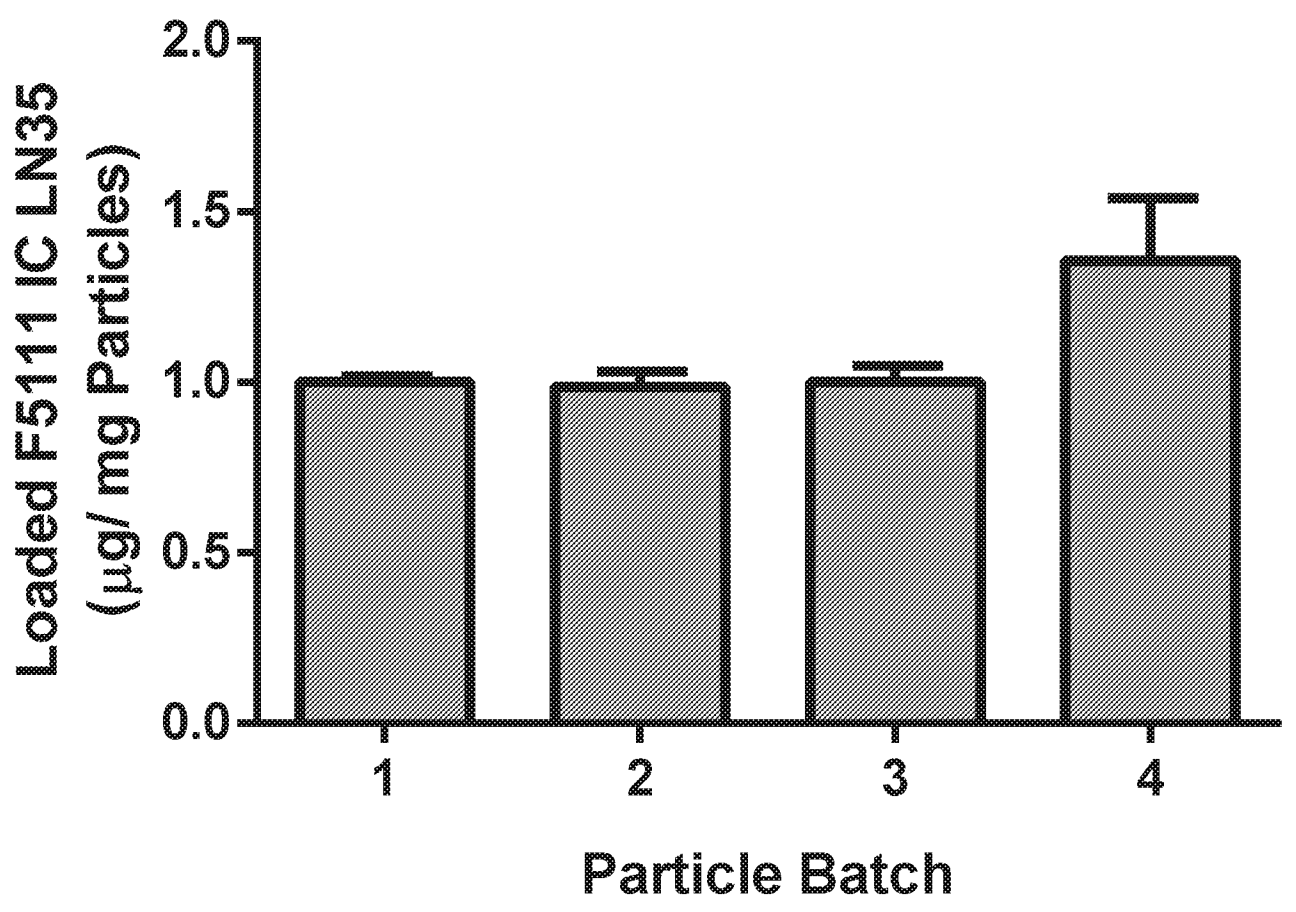

FIG. 20 is a graph showing F5111 IC LN35 loading under acidic conditions, as measured by a BCA protein assay. 1.25 µg F5111 IC LN35 was added per mg PLGA during particle synthesis. Maximum loading efficiency was achieved with Batch #4.

Figure 21:
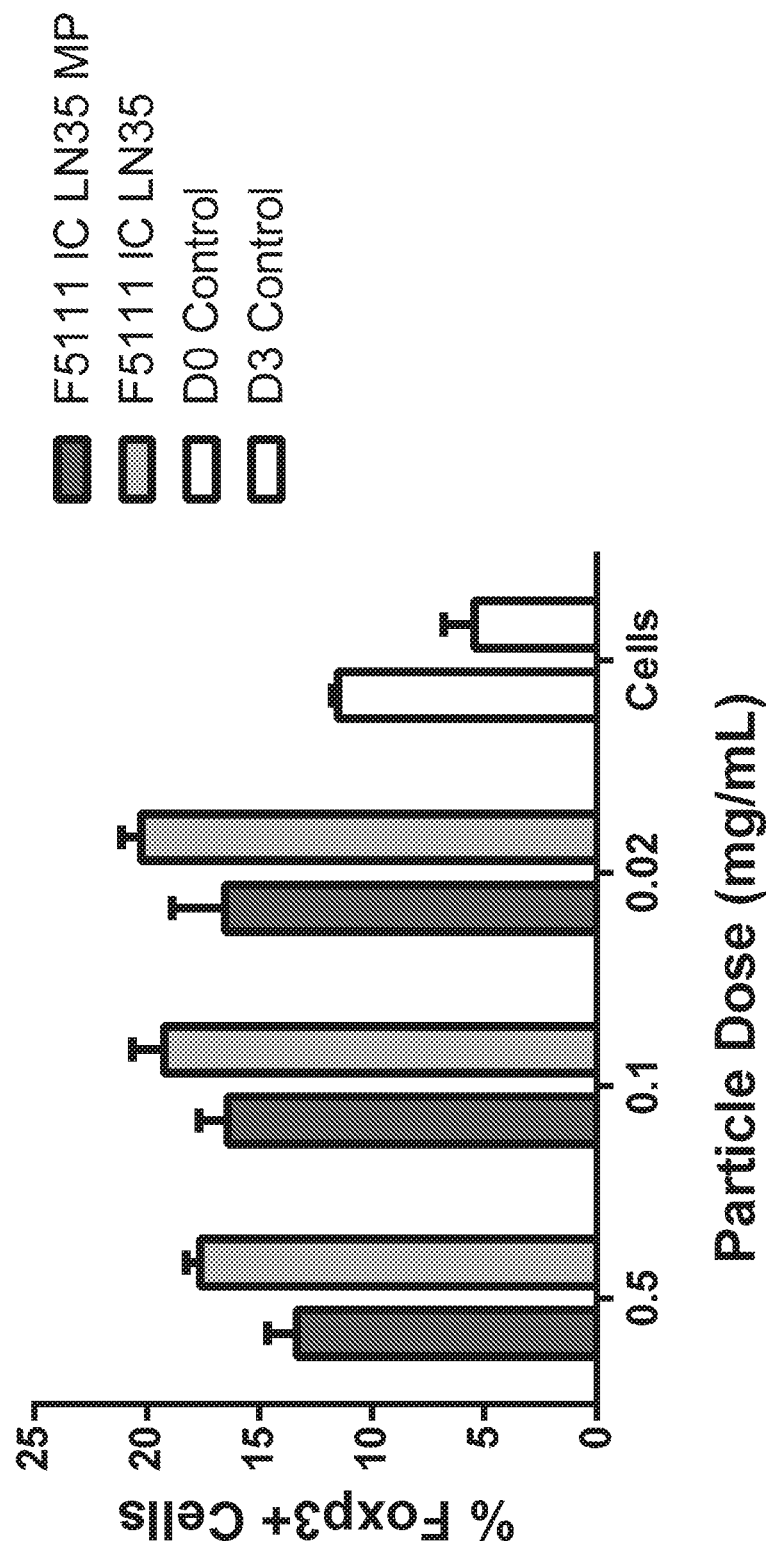

FIG. 21 is a graph showing that F5111 IC LN35-loaded MPs and unconjugated F5111 IC LN35 expanded Foxp3+ cells relative to untreated cells on day 0 and day 3. F5111 IC LN35-loaded microparticles or free F5111 IC LN35 (at a dose equivalent to the particle loading dose) were incubated with CD4+ cells from B6 mice for 3 days, and cells were analyzed for FOXP3 expression via flow cytometry.

Figure 22:
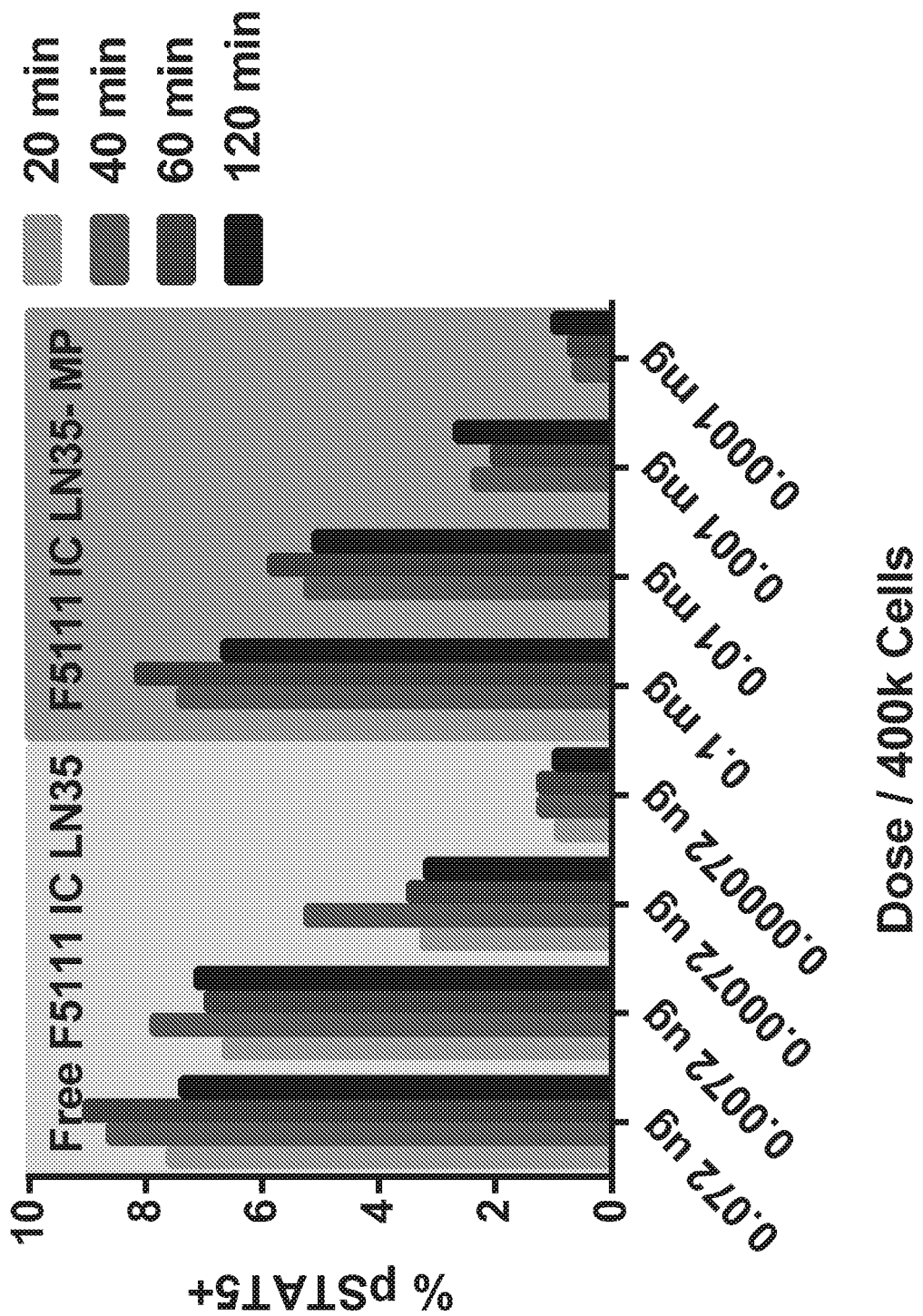

FIG. 22 is a graph showing the results of B6 CD4+ cells stimulation with titrated encapsulated particle doses or equivalent free doses of F5111 for different lengths of time, and the analysis of pSTAT5 expression using flow cytometry. A dose titration for free and MP-loaded F5111 IC LN35 was observed, with maximum pSTAT5 expression achieved after 1 hour of stimulation.

Figure 23:
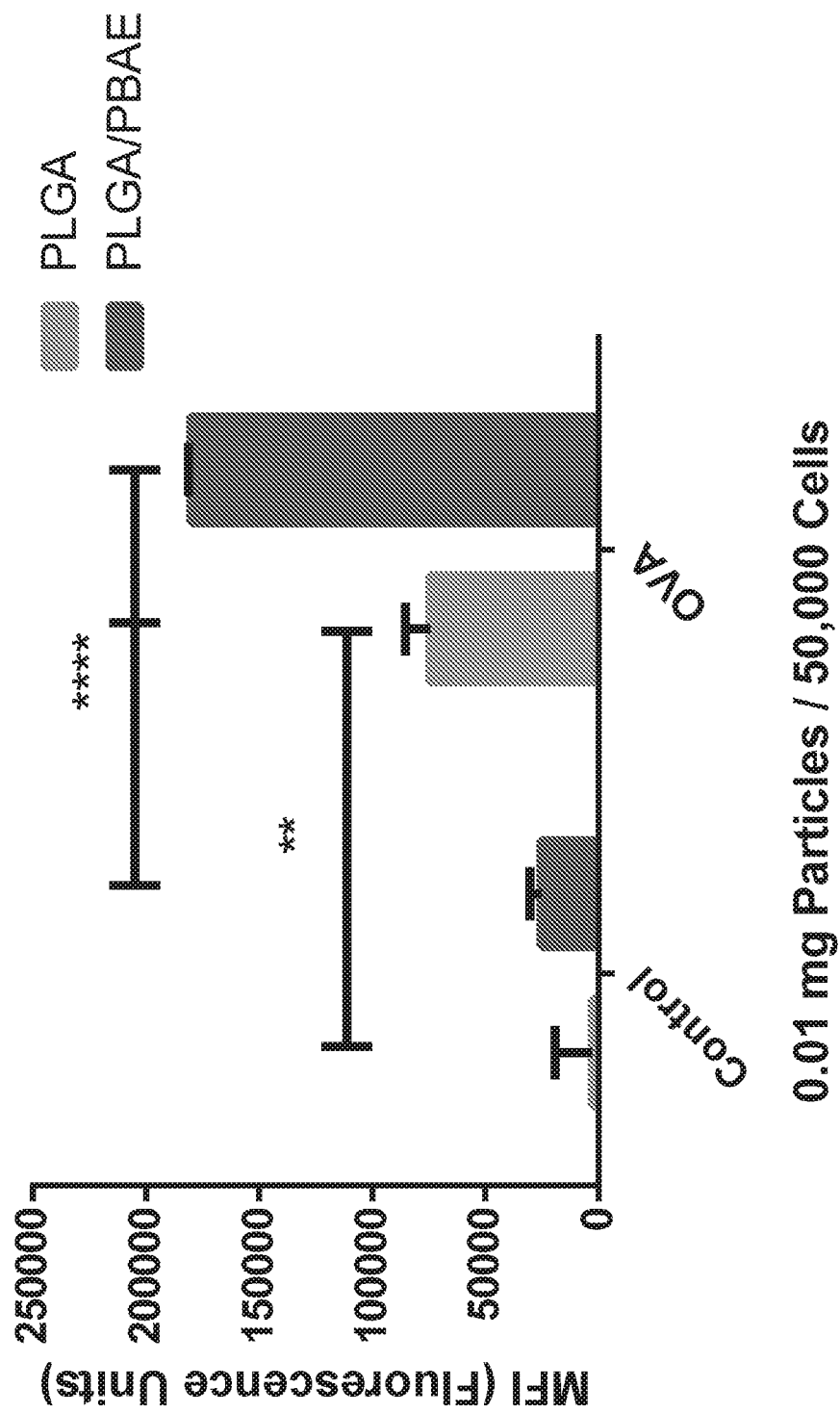

FIG. 23 is a graph showing that OVA-specific TolAPCs exhibited enhanced binding to OT-II cells. PLGA/PBAE TolAPC demonstrated significantly better binding as compared to PLGA TolAPC. Fluorescent TolAPCs were incubated with CFSE-labelled CD4+ T cells from OT-II mice for 1 hour at 37° C. and binding was assessed using flow cytometry. Statistical comparisons were performed using one-way ANOVA with Tukey's post-test using GraphPad Prism software version 6.01.

Figure 24:
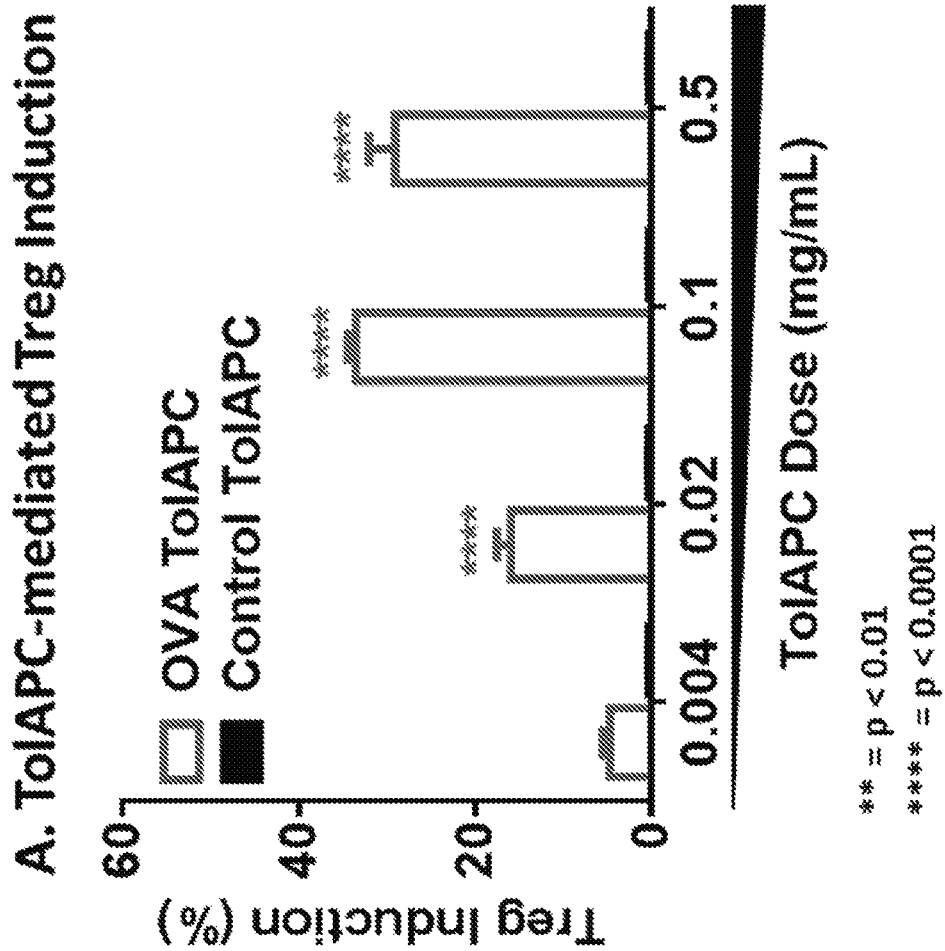

FIG. 24 is a graph showing that unloaded TolAPC surface-conjugated with OVA tetramer and anti-CD28 induced OVA-specific Tregs from naïve OT-II CD4+ T cells, while TolAPC bearing a control tetramer did not induce $T_{Reg}$ cells. Maximum $T_{Reg}$ induction was achieved at a TolAPC dose of 0.1 mg/mL. Statistical comparisons were performed using two-tailed student's t-test using GraphPad Prism software version 6.01.

Figure 25:
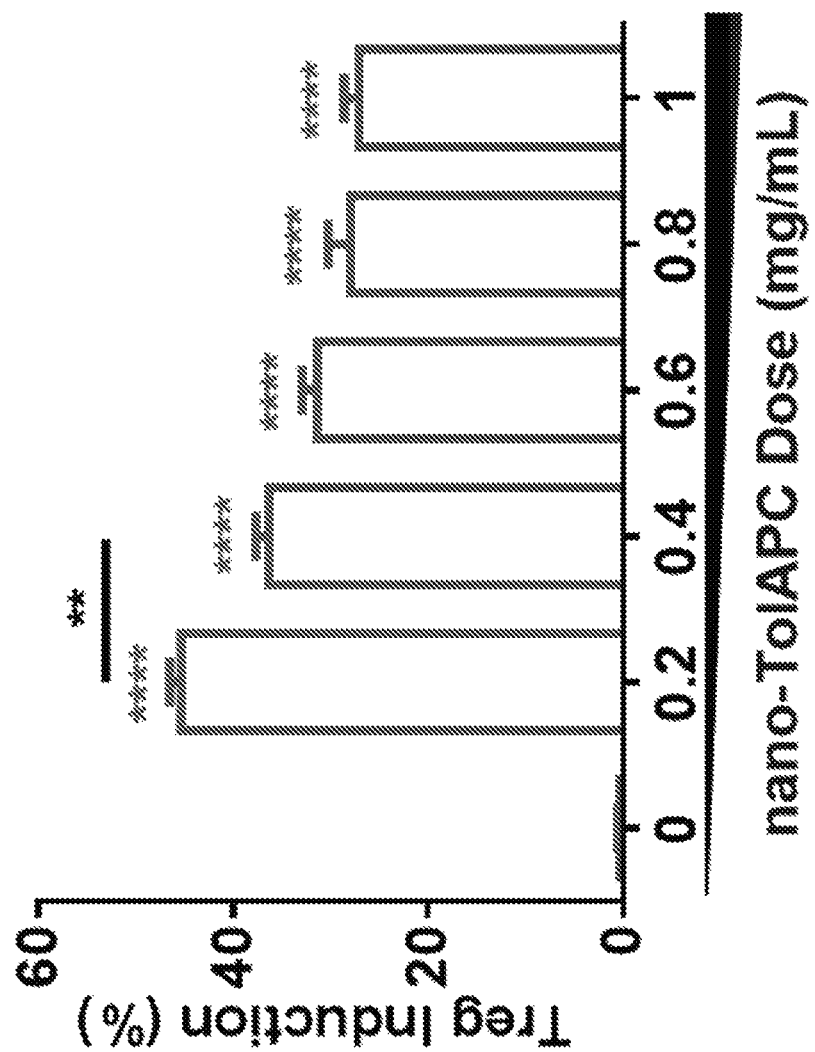

FIG. 25 is a graph showing that nanoscale TolAPCs induced up to 45% ovalbumin-specific $T_{Reg}$ cells in the absence any exogenous factors. TolAPCs were incubated at varying concentrations with naïve CD4+ T cells from OT-II mice for 3 days. FOXP3 expression was analyzed by flow cytometry to assess $T_{Reg}$ cell induction. Statistical comparisons were performed using two-way ANOVA with Sidak's post-test using GraphPad Prism software version 6.01.

Figure 26:
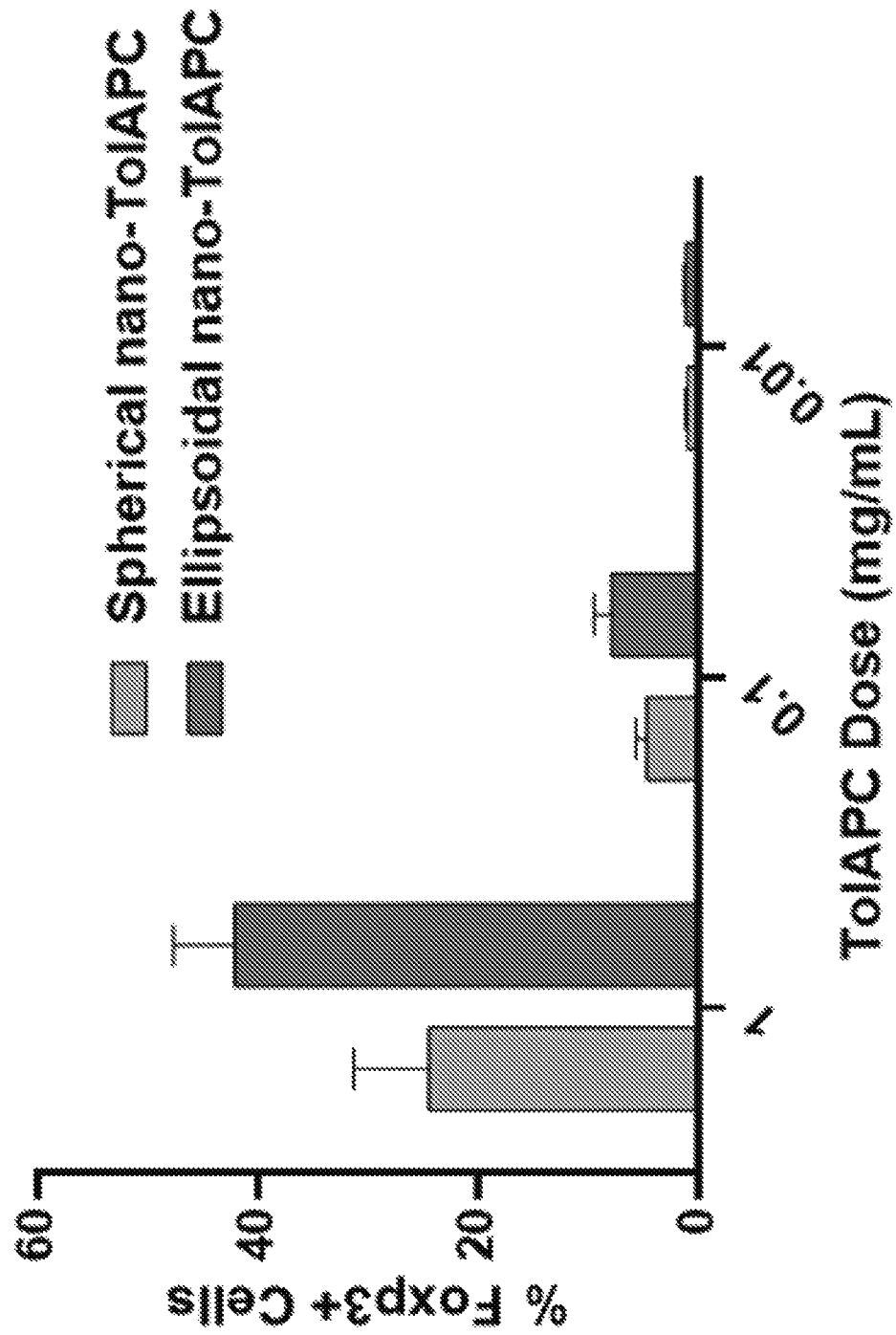

FIG. 26 is a graph showing that ellipsoidal nano-TolAPCs improve $T_{Reg}$ cell induction compared to spherical nano-TolAPCs at a 1 mg/mL dose. TolAPCs were incubated with naïve CD4+ T cells from OT-II mice for 3 days, and then stained for FOXP3 to assess $T_{Reg}$ cell induction.

Figure 27:
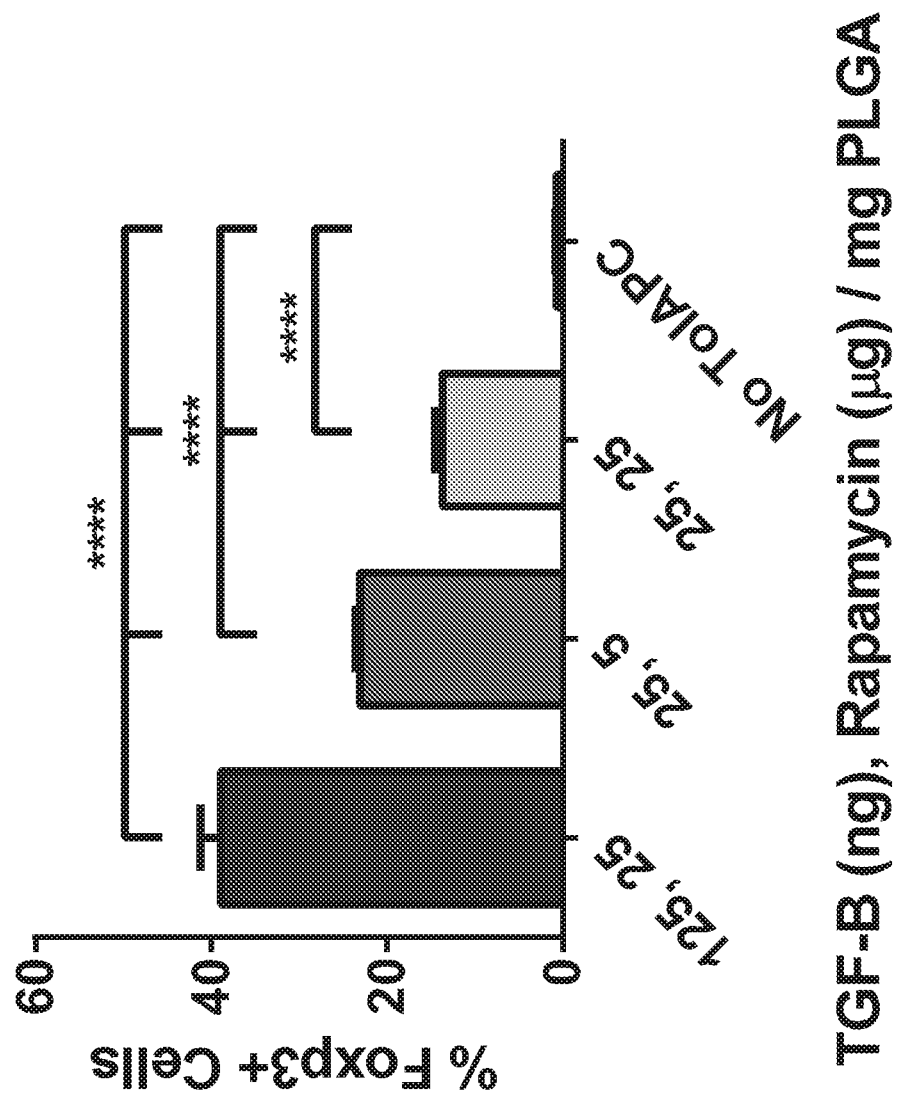

FIG. 27 is a graph showing $T_{Reg}$ cell induction by OVA-TolAPCs loaded with different amounts of TGF-β and rapamycin. A 100 μg/mL dose of OVA-TolAPCs was used to induce $T_{Reg}$ cells from naïve OT-II CD4+ T cells. A loading dose of 125 ng TGF-β and 25 μg rapamycin/mg PLGA during TolAPC synthesis was found to be most effective for $T_{Reg}$ cell induction. Statistical comparisons were performed using one-way ANOVA with Tukey's post-test using GraphPad Prism software version 6.01.

Figure 28:
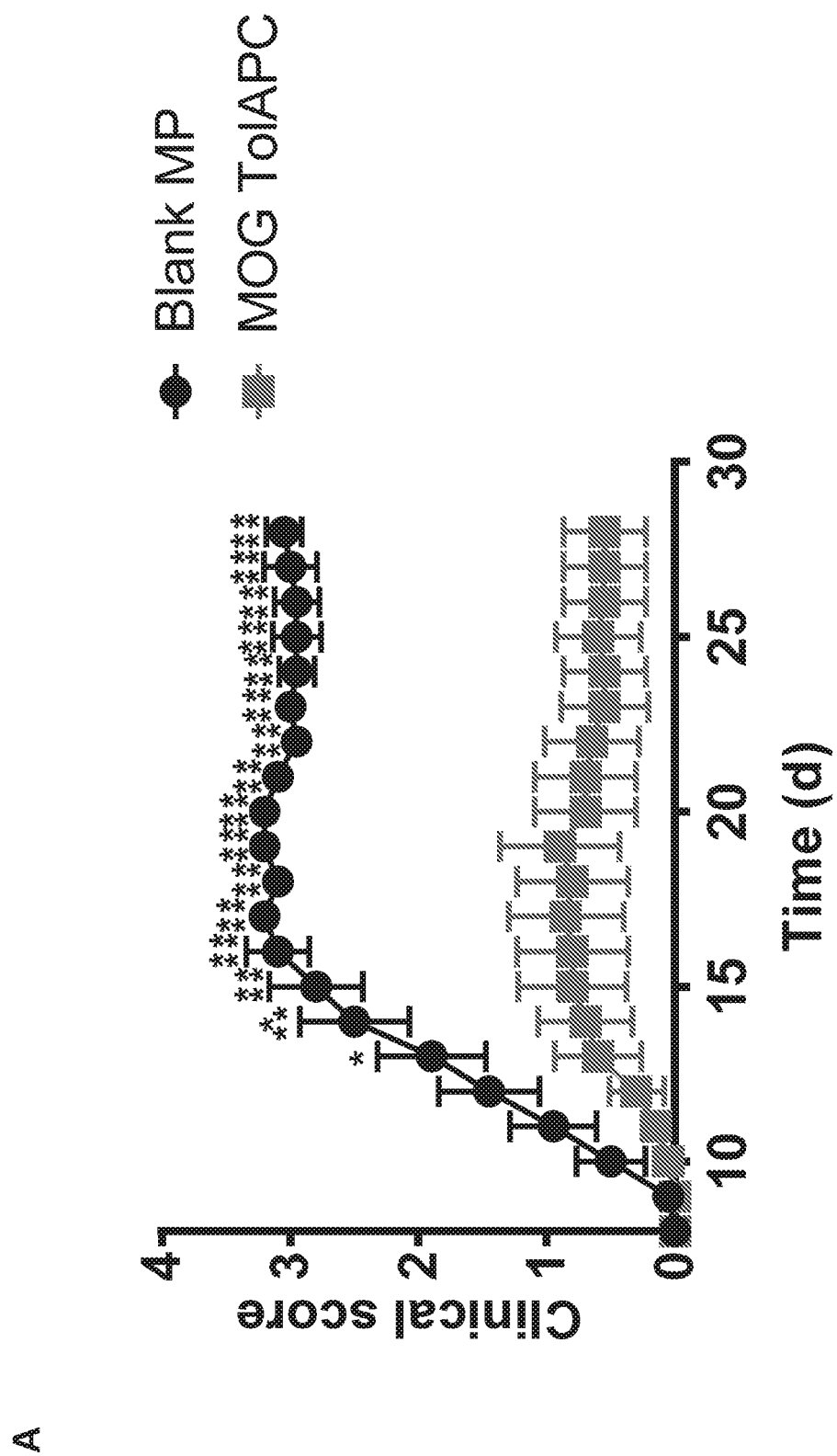
Figure 28:
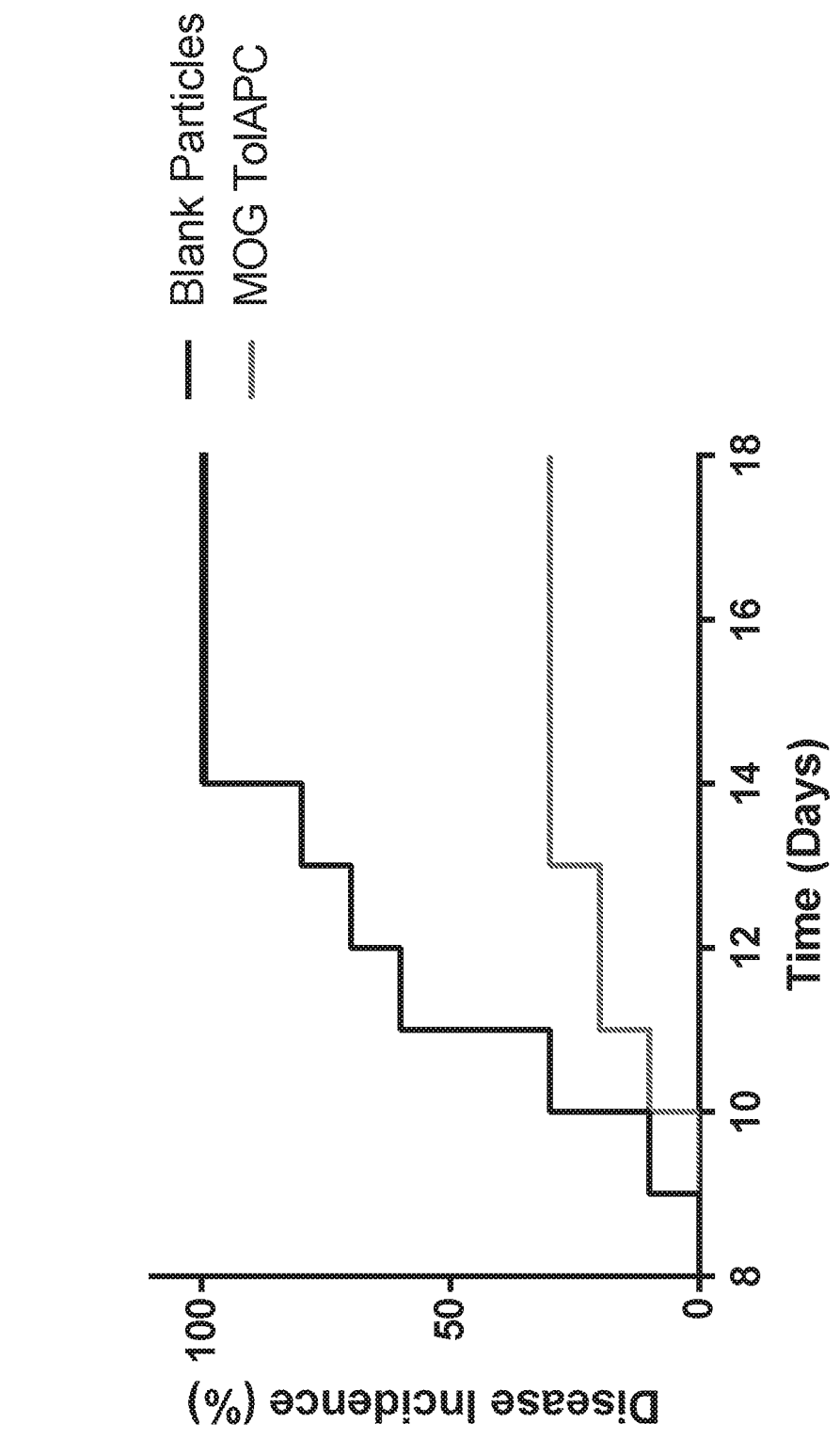

FIG. 28A is a graph showing that MOG-TolAPC treatment partially prevented EAE development in mice compared to blank particles. FIG. 28B is a graph showing that MOG-TolAPC treatment delayed disease onset and reduced disease incidence in mice, with only 30% of TolAPC-treated mice developing disease as compared to 100% of control mice. Statistical comparisons were performed using two-tailed student's t-test in GraphPad Prism software version 6.01.

Figure 29:
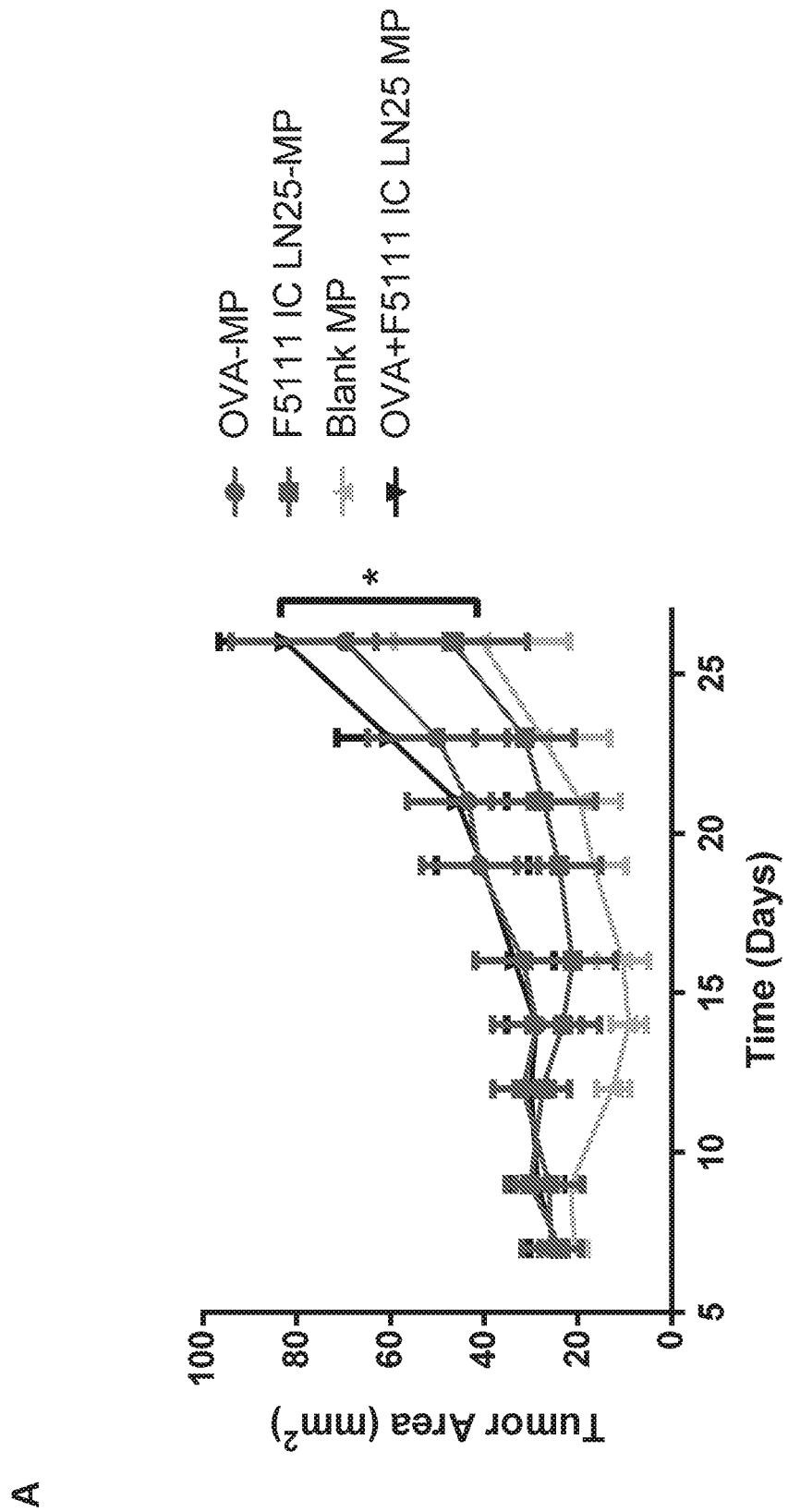
Figure 29:
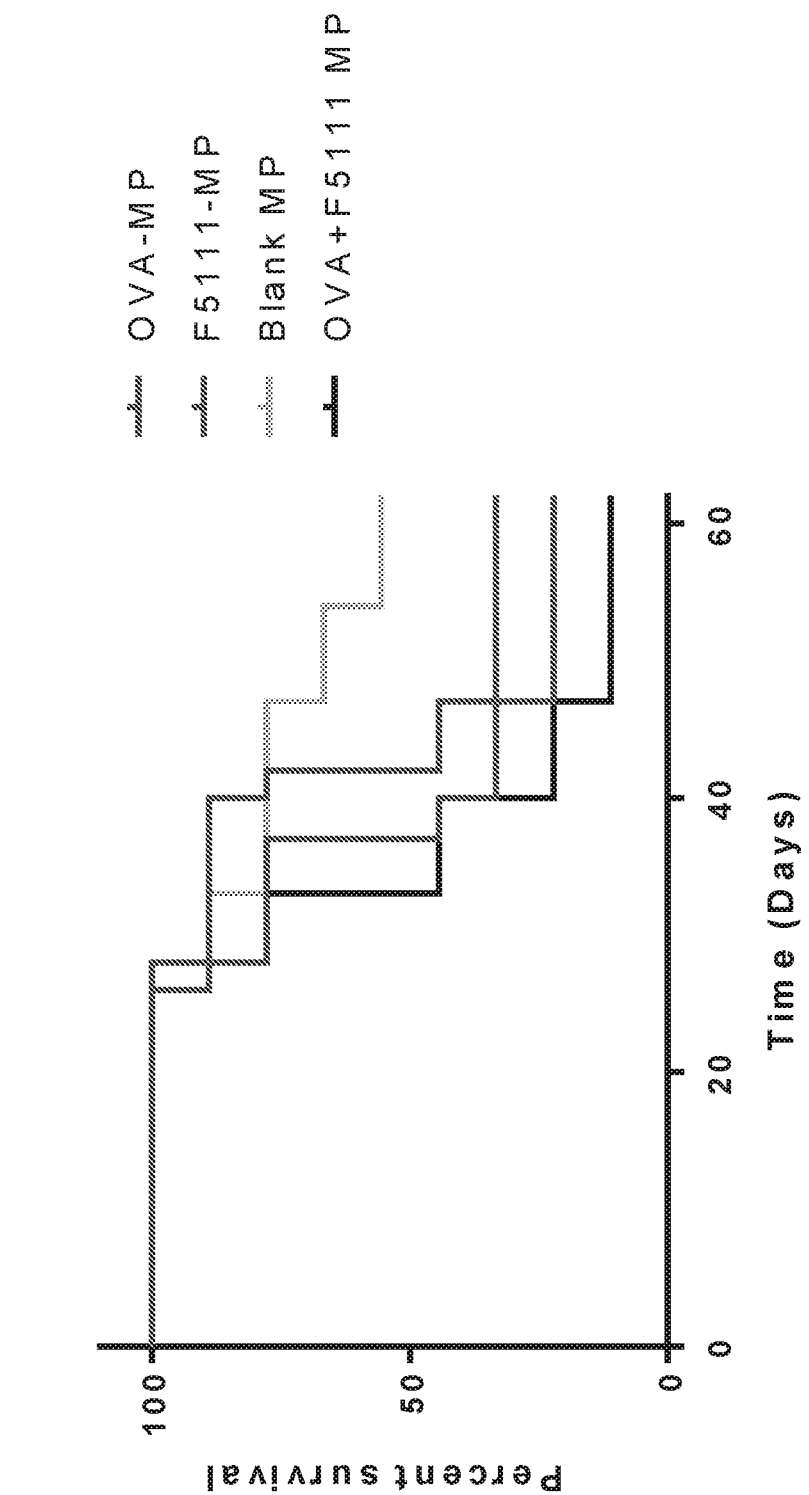

FIG. 29A is a graph showing results of a MC38-OVA tumor protection study. FIG. 29B is a graph showing survival of MC38-OVA-bearing mice. Mice received blank MPs or MPs functionalized with OVA peptide-loaded I-A(b) MHC II tetramers, F5111 IC LN25, or a combination of both via intranodal administration. OVA+F5111 IC LN25 TolAPC treatment conferred tumor protection, translating to more rapid tumor growth and shorter survival in TolAPC-treated mice compared to mice treated with control particles. Statistical comparisons were performed using two-way ANOVA with Sidak's post-test using GraphPad Prism software version 6.01

DETAILED DESCRIPTION OF THE INVENTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Biodegradable Particle-Based Tolerogenic Artificial Antigen Presenting Cells

The presently disclosed subject matter provides biodegradable particles for interacting with immune cells to generate an immunosuppressive effect. More particularly, the presently disclosed subject matter provides biodegradable particle-based tolerogenic artificial antigen presenting cells (also referred to herein as "TolAPC" or "T-aAPC," which are used interchangeably herein) which can be used to induce proliferation of $T_{Regs}$ in vitro and in vivo for autoimmune therapy. As used herein, "$T_{Regs}$" are a subpopulation of T cells that modulate the immune system, maintain tolerance to self-antigens, and prevent autoimmune disease.

The presently disclosed TolAPCs can successfully interact with only those $T_{Regs}$ that recognize the same self-antigens that are displayed by the particles and recognized by only disease-causing cytotoxic T cells. Although primarily used in an immunostimulatory capacity, artificial antigen presenting cells (aAPC) can recapitulate the interaction between tolerogenic antigen presenting cells and naïve CD4+ cells, thereby directing T cells toward a regulatory phenotype. As used herein, an "artificial antigen presenting cell" (aAPC) is an artificial biomimetic particle-based platform that has been made in vitro and has not been made naturally by a body. As used herein, "naïve cells" are cells that have not been activated by or exposed to the selected antigen.

An "antigen" as used herein is a substance that binds specifically to its respective antibody. The term "antibody," as used herein, refers to a protein that binds specifically to a particular substance (i.e., an antigen). Typically, an immunoglobulin or antibody is a protein that comprises at least one complementarity determining region (CDR). The CDRs form the "hypervariable region" of an antibody, which is responsible for antigen binding (discussed further below). A whole immunoglobulin typically consists of four polypeptides: two identical copies of a heavy chain (HC) polypeptide and two identical copies of a light chain (LC) polypeptide. Each of the heavy chains contains one N-terminal variable ($V_H$) region and three C-terminal constant ($C_H1$, $C_H2$, and $C_H3$) regions, and each light chain contains one N-terminal variable ($V_L$) region and one C-terminal constant ($C_L$) region. The light chains of antibodies can be assigned to one of two distinct types, either kappa (κ) or lambda (λ), based upon the amino acid sequences of their constant domains. In a typical immunoglobulin, each light chain is linked to a heavy chain by disulphide bonds, and the two heavy chains are linked to each other by disulphide bonds. The light chain variable region is aligned with the variable region of the heavy chain, and the light chain constant region is aligned with the first constant region of the heavy chain. The remaining constant regions of the heavy chains are aligned with each other.

The variable regions of each pair of light and heavy chains form the antigen binding site of an antibody. The $V_H$ and $V_L$ regions have the same general structure, with each region comprising four framework (FW or FR) regions. The term "framework region," as used herein, refers to the relatively conserved amino acid sequences within the variable region which are located between the CDRs. There are four framework regions in each variable domain, which are designated FR1, FR2, FR3, and FR4. The framework regions form the β sheets that provide the structural framework of the variable region (see, e.g., C. A. Janeway et al. (eds.), *Immunobiology,*

5th Ed., Garland Publishing, New York, N.Y. (2001)). In nature, antibodies are produced by plasma cells in response to infection or immunization, but antibodies may be syn-

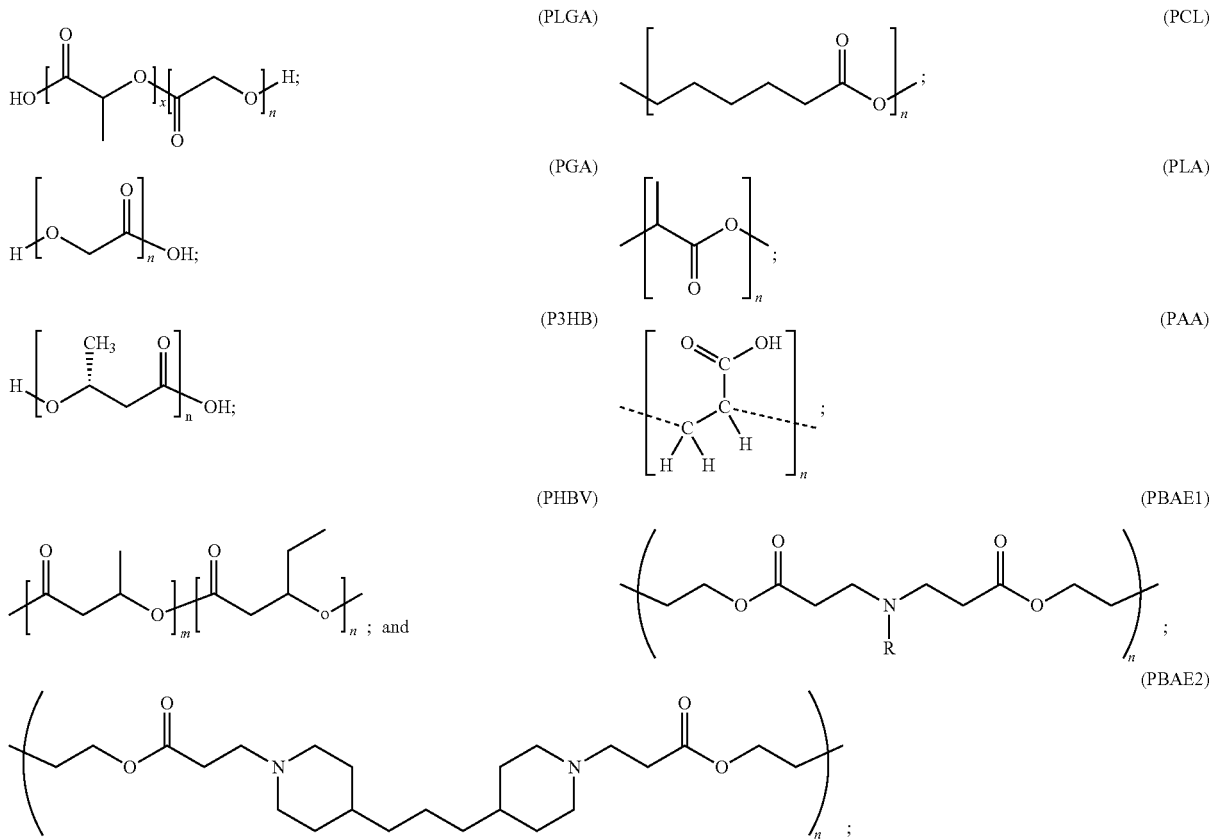

thetically or recombinantly generated using a variety of methods known in the art.

Representative embodiments of artificial antigen presenting cells are provided in U.S. Patent Application Publication Nos. 2018/0256745 and 2014/0370099, each of is incorporated by reference in their entirety.

The presently disclosed particles can be fabricated from materials, for example, blends of polymeric materials, that are generally regarded as safe and that degrade in water. Further, the presently disclosed particles can be fabricated to selectively engage only cells specific for certain autoimmune antigens. The presently disclosed aAPC platform can be adapted in a modular fashion to expand antigen-specific $T_{Regs}$ against any antigen of choice, giving it potential as an "off-the-shelf" therapy for a variety of autoimmune diseases.

In various embodiments, the presently disclosed particles comprise a polyester or polyester blend with at least one soluble protein or small molecule encapsulated within the polymeric particle and at least two types of protein attached to the surface of the polymeric particle or to a coating on its surface. Exemplary polyesters comprise one or more of poly(lactic-co-glycolic acid) (PLGA), polycaprolactone (PCL), polyglycolide (PGA), poly(lactic acid) (PLA), a polyhydroxyalkanoate (PHA), such as poly-3-hydroxybutyrate (P3HB), poly(acrylic acid) (PAA), poly(3-hydroxybutyrate-co-3-hydroxyvalerate) (PHBV), a poly(beta-amino ester) (PBAE), or combinations thereof, or other hydrolytically biodegradable polymers. Accordingly, the presently disclosed biodegradable particles include one or more of the following polyesters:

wherein each x, y, m, and n can independently be an integer from 1 to 10,000.

In particular embodiments, the presently disclosed subject matter includes a PBAE comprising a side chain monomer having two secondary amines instead of one primary amine that reacts with the diacrylate backbone. A representative example is PBAE2 immediately hereinabove, which uses 4,4'-trimethylenedipiperidine as the side chain.

As used herein, "biodegradable" compounds are those that, when introduced into cells, are broken down by the cellular machinery or by hydrolysis into components that the cells can either reuse or dispose of without significant toxic effect on the cells (i.e., fewer than about 20% of the cells are killed when the components are added to cells in vitro). The components preferably do not induce inflammation or other adverse effects in vivo. In certain preferred embodiments, the chemical reactions relied upon to break down the biodegradable compounds are uncatalyzed.

In certain embodiments, the biodegradable particle comprises a material having one or more degradable linkages, such as an ester linkage, a disulfide linkage, an amide linkage, an anhydride linkage, and a linkage susceptible to enzymatic degradation. Representative degradable linkages include, but are not limited to:

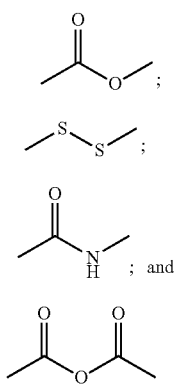

In some embodiments, the biodegradable particle comprises a poly(lactic-co-glycolic acid) polyethylene glycol (PLGA-PEG) block copolymer. In other embodiments, the biodegradable particle comprises poly(lactic acid)-based polymeric matrices, such as polylactic acid (PLA), poly(D,L-lactide-co-glycolide) (PLGA), and poly (D,L-lactic acid) (PDLLA). In other embodiments, the biodegradable particle comprises a copolymer of a poly(lactic acid)-based polymer and a non-poly(lactic acid)-based polymer, such as a combination of PLA and PCL. In some embodiments, blends of polyesters may be used, such as PLGA/PCL or PLGA/PBAE. In some embodiments, the PLGA content is between about 50 to about 90% with the remainder being PCL and/or PBAE. In particular embodiments, the biodegradable particle comprises a blend of PLGA and a (PBAE). In yet other embodiments, nondegradable polymers that are used in the art, such as polystyrene, are blended with a degradable polymer or polymers disclosed immediately hereinabove to create a copolymer system. Accordingly, in some embodiments, a nondegradable polymer is blended with the biodegradable polymer.

Exemplary PBAEs suitable for use with the presently disclosed subject matter include those disclosed in U.S. Pat. Nos. 9,884,118; 9,802,984; 9,717,694; and 8,992,991; and U.S. Patent Application Publication Nos. 2018/0256745; 2018/0112038; 2017/0216363; and 2015/0273071.

In some embodiments, a specific PBAE or end-modified biodegradable PBAE is used, such as 1-(3-aminopropyl)-4-methylpiperazine end-capped poly(1,4-butanediol diacrylate-co-4,4-trimethylenedipiperidine) having the structure:

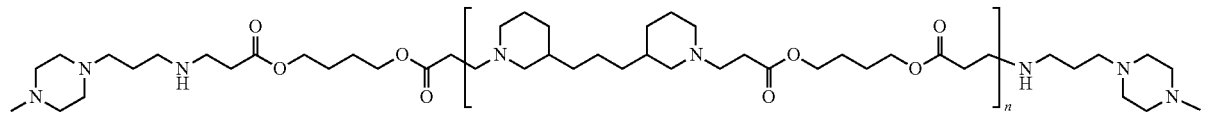

In particular embodiments, the presently disclosed tolerogenic artificial antigen presenting cells (T-aAPCs) comprise a three-dimensional microparticle or nanoparticle having a non-spherical asymmetrical shape. In such embodiments, as the particle becomes flatter, the radius of curvature of the particle becomes larger. Conversely, as a surface on the particle becomes more curved, the radius of curvature becomes smaller. In particular embodiments, the asymmetrical shape of the three-dimensional microparticle or nanoparticle has at least one surface having a radius of curvature along at least one axis selected from one of the following ranges: (a) about 1 nm to about 10 nm; (b) about 11 nm to about 100 nm; (c) about 101 nm to about 400 nm; (d) about 401 nm to about 1 µm; (e) about 10 µm to about 20 µm; (f) about 20 µm to about 100 µm; and (g) about 101 µm to about 1 mm. In some embodiments, the particle has at least one surface that has a radius of curvature that does not include the range from about 1 micron to about 10 microns.

In certain embodiments, the asymmetrical shape of the three-dimensional microparticle or nanoparticle is defined by a dimension (a) along an x-axis, a dimension (b) along a y-axis, and a dimension (c) along a z-axis, wherein at least one of (a), (b), or (c) is not equal to at least one other dimension (a), (b), or (c).

In yet other embodiments, the three-dimensional microparticle or nanoparticle comprises an ellipsoid selected from the group consisting of: a prolate ellipsoid, wherein the dimension (a) along the x-axis is greater than the dimension (b) along the y-axis, and wherein the dimension (b) along the y-axis is equal to the dimension (c) along the z-axis, such that the prolate ellipsoid can be described by the equation a>b=c; a tri-axial ellipsoid, wherein the dimension (a) along the x-axis is greater than the dimension (b) along the y-axis, and wherein the dimension (b) along the y-axis is greater than the dimension (c) along the z-axis, such that the tri-axial ellipsoid can be described by the equation a>b>c; and an oblate ellipsoid, wherein the dimension (a) along the x-axis is equal to the dimension (b) along the y-axis, and wherein the dimension (b) along the y-axis is greater than the dimension (c) along the z-axis, such that the oblate ellipsoid can be described by the equation a=b>c.

In some embodiments, the microparticle or nanoparticle has an aspect ratio ranging from about 1.1 to about 5, including about 1.1, 1.5, 2.0, 2.5, 3.0, 3.5, 4.0, and 4.5 to about 5.

In some embodiments, the T-aAPC has a three-dimensional shape that mimics a shape of a cell or a microorganism. In particular embodiments, the cell or a microorganism is selected from the group consisting of a bacterium, an archaeon, a protozoan, a fungus, an algae, and a virus. In yet more particular embodiments, the cell or microorganism has a shape selected from the group consisting of a spiral, a cube, a rod, a comma, a star, a square, a column, a polyhedran, a helix, an icosahedran, a cylinder, a tetrahedron, and a pyramid.

In certain embodiments, as described in part hereinabove, the three-dimensional microparticle or nanoparticle comprises a material having one or more of the following characteristics: (i) one or more degradable linkages, as defined hereinabove; (ii) a stretchable modulus; and (iii) a glass transition temperature such that the material comprising the three-dimensional microparticle or nanoparticle is a solid at room temperature and/or body temperature.

As used herein, "glass transition temperature" refers to the temperature at which amorphous polymers undergo a transition from a rubbery, viscous amorphous liquid, to a brittle, glassy amorphous solid. As used herein, "Young's modulus of elasticity" quantifies the elasticity of the polymer. It is defined, for small strains, as the ratio of rate of change of stress to strain.

As used herein, the term "nanoparticle," refers to a particle having at least one dimension in the range of about 1 nm to about 1000 nm, including any integer value between 1 nm and 1000 nm (including about 1, 2, 5, 10, 20, 50, 60, 70, 80, 90, 100, 200, 500, and 1000 nm and all integers and fractional integers in between). In some embodiments, the nanoparticle has at least one dimension, e.g., a diameter, of about 100 nm. In some embodiments, the nanoparticle has a diameter of about 200 nm. In other embodiments, the nanoparticle has a diameter of about 500 nm.

In yet other embodiments, the nanoparticle has a diameter of about 1000 nm (1 µm). In such embodiments, the particle also can be referred to as a "microparticle." Thus, the term "microparticle" includes particles having at least one dimension in the range of about one micrometer (1 µm), i.e., $1 \times 10^{-6}$ meters, to about 1000 µm. The term "particle" as used herein is meant to include nanoparticles and microparticles.

Proteins Conjugated to or Encapsulated in TolAPCs

The biodegradable particle described herein comprises a first protein that binds to an immune cell, and a second protein that promotes proliferation and/or activation of immune cells, and a third soluble protein or small molecule encapsulated within the particle, wherein the first and second proteins are attached to a surface of the particle or to a coating on the surface thereof. Exemplary proteins conjugated to the surface of the particle includes a first protein that binds to immune cells, and in particular T cells, such as anti-CD3, MHC-peptide complex, including MHC-I and MHC-II molecules, or other T cell receptor (TCR) binder. In some embodiments, the first protein is a peptide-loaded MHC II tetramer complex (also referred to as an "MHC II tetramer-peptide complex"). It will be appreciated that peptide-MHC (pMHC) class II multimers display an antigenic peptide in the class H binding groove, and function as a surrogate for recognition events that occur as part of T cell interaction with antigen-presenting cells. Various methods for displaying peptide-MHC class II molecules have been successfully used, ranging from monomeric pMHC bound to solid substrates or soluble in solution, to higher order multimers complexed with various scaffold molecules. The most prevalent form of multimer used in the art typically contains biotin-labeled pMHC displayed on streptavidin molecules, forming tetravalent or "tetramer" complexes (Nepom, G. T., *J Immmunol.*, 188(6): 2477-2482 (2012); Rossjohn et al., *Annu Rev Immunol.*, 33(1): 169-200 (2015)). The MHC II tetramer may be loaded with any suitable peptide antigen. In some embodiments, the MHC II tetramer is loaded with an insulin B peptide or a chromogranin peptide.

The biodegradable particle also comprises a second protein conjugated to the surface of the particle. In certain embodiments, the second protein promotes expansion, proliferation, activation, differentiation, etc., of certain types of immune cells (e.g., T cells). Although the second protein preferably is conjugated to the surface of the particle, in some embodiments the second protein may be encapsulated within the biodegradable particle. In some embodiments, the second protein may be a fusion protein comprising at least a portion of an antibody and at least a portion of a cytokine. Such antibody-cytokine fusion proteins are referred to in the art as "immunocytokines." Immunocytokines (IC) have been used in the art to extend the serum half-life of cytokines or for targeting to disease antigens (see, e.g., Pasche, N. and D. Neri, *Drug Discovery Today*, 17(11-12): 583-590 (2012); and Kontermann, R. E., *Arch. Biochem. Biophys.*, 526(2): 194-205 (2012)). The term "cytokine," as used herein, refers to a protein produced by cells that affect the behavior of other cells. Cytokines act on specific cytokine receptors expressed by target cells. Cytokines produced by lymphocytes often are referred to as "lymphokines" or "interleukins." The immunocytokine conjugated to the surface of the biodegradable particle may be comprised of any suitable combination of antibody and cytokine, or portions thereof. In one embodiment, the cytokine portion of the immunocytokine is IL-2, and the antibody portion of the immunocytokine is an anti-IL-2 antibody. In some embodiments, the fusion protein is a single chain protein. For example, a single chain immunocytokine described herein can be a fusion polypeptide that includes a cytokine fused to at least a portion (e.g., an immunoglobulin heavy chain and/or an immunoglobulin light chain) of an anti-cytokine antibody. For example, a single chain immunocytokine described herein can be a fusion polypeptide that includes an immunoglobulin heavy chain (e.g., an immunoglobulin heavy chain from an anti-cytokine antibody) fused to an IL-2 polypeptide (or fragment thereof) that can bind an IL-2Rα/IL-2Rβ/γc polypeptide complex fused to an immunoglobulin light chain (e.g., an immunoglobulin light chain from an anti-cytokine antibody).

Figure 1:
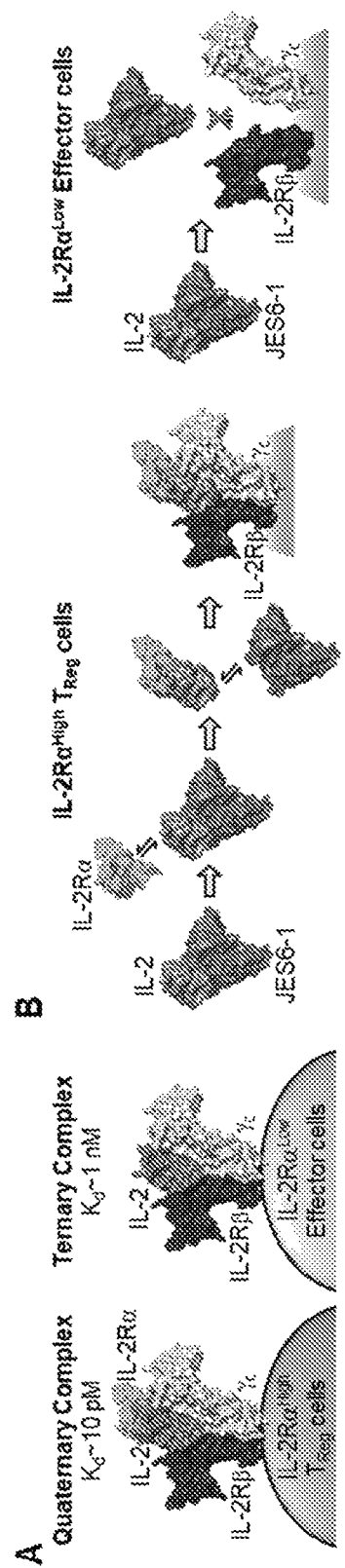
FIG. 1A is a schematic showing that IL-2 activates both IL-2$\alpha^{High}$ $T_{Reg}$ and IL2R$\alpha^{Low}$ T cells (thereafter referred to as "effector cells").
FIG. 1B is a schematic illustrating the mechanism of action for the JES 6-1 antibody.

IL-2 is a multi-functional cytokine that regulates immune cell differentiation, proliferation, survival, and activity. IL-2 forms a high-affinity (Kd~10 pM) quaternary complex with the IL-2 receptor-α (IL-2Rα, also CD25), IL-2Rβ, and common $\gamma_c$ chains or an intermediate-affinity (Kd~1 nM) ternary complex with only the IL-2Rβ and $\gamma_c$ chains (see FIG. 1A) (Liao et al., *Immunity*, 38(1): 13-25 (2013); and Wang et al., *Science*, 310(5751): 1159-1163 (2005)). Thus, expression of the non-signaling IL-2Rα subunit regulates cytokine sensitivity, whereas IL-2Rβ and $\gamma_c$ mediate signaling (Liao et al., supra; and Malek, T. R., *Annu Rev Immunol.*, 26(1): 453-479 (2008)). Since IL-2Rα is abundantly expressed on $T_{Reg}$ cells, but virtually absent from naïve immune effector cells (i.e. CD4+ T, CD8+ T, and natural killer (NK) cells), low-dose IL-2 treatment preferentially stimulates polyclonal expansion of $T_{Regs}$ over effector cells (Liao et al., supra, and Boyman, O and Sprent, J., *Nat Rev Immunol.*, 12(3):180-190 (2012)). Extensive preclinical and clinical work demonstrates that low dose IL-2 effectively promotes $T_{Reg}$ expansion; however, IL-2 also expands effector cells, which leads to undesirable off-target effects and toxicities (Boyman, O and Sprent, J., *Nat Rev Immunol.*, 12(3):180-190 (2012); and Klatzmann, D. and Abbas, A. K., *Nat Rev Immunol.*, 15(5): 283-294 (2015)). Development of a 'biased' version of IL-2 that potentiates the activity of $T_{Reg}$ but not effector cells would represent a significant advance for treatment of autoimmune diseases such as type 1 diabetes (T1D), as well as for transplantation medicine. It was recently found that administration of IL-2 in complex with the anti-IL-2 antibody JES6-1 potently expands $T_{Reg}$ but not effector cells (Boyman et al., *Science*, 311(5769): 1924-1927 (2006). Subsequent work showed that IL-2/JES6-1 complexes prevent diabetes (Tang et al., *Immunity*, 28(5): 687-697 (2008); Grinberg-Bleyer et al., *J Exp Med.*, 207(9): 1871-1878 (2010)) and other autoimmune diseases in mice (Webster et al., *J. Exp. Med.*, 206(4): 751-760 (2009); and Liu et al., *Eur J Immunol.*, 40(6): 1577-1589 (2010)). Determination of the crystal structure of the IL-2/JES6-1 complex revealed that JES6-1 acts through a unique exchange mechanism in which antibody binding sterically obstructs IL-2 interaction with IL-2Rβ and $\gamma_c$, but IL-2Rα allosterically displaces JES6-1 from IL-2 to allow for IL-2Rβ and $\gamma_c$ activation on IL-2Rα$^{High}$ T$_{Reg}$ cells. In contrast, JES6-1 ablates IL-2 activity on IL-2Rα$^{Low}$ effector cells via steric blockade (see FIG. 1B) (Spangler et al., *Immunity,* 42(5): 815-825 (2015)).

In addition to JES6-1, any other suitable anti-IL-2 antibody, or portion thereof, may be included in the immunocytokine, several of which are known in the art and are commercially available (see, e.g., Letourneau et al., *Proc. Natl. Acad. Sci. USA,* 107(5): 2171-2176 (2010)). Examples of antibodies whose heavy chain variable domain and/or constant domains can be used in a single chain immunocytokine described herein include, without limitation, monoclonal antibody F5111 (referred to herein as "F5111") heavy chains, monoclonal antibody F5111.4 heavy chains, monoclonal antibody F5111.7 heavy chains, monoclonal antibody F5111.8 heavy chains, and monoclonal antibody F5111.2 heavy chains. Other immunoglobulins whose heavy chain variable domains and/or constant domains can be used in the single chain immunocytokine described herein also are described in, e.g., Trotta et al., *Nat Med.,* 24(7): 1005-1014 (2018).

For example, the single chain immunocytokine described herein can include an antibody heavy chain variable domain having the amino acid sequence set forth in SEQ ID NO: 1, or an amino acid sequence that is at least about 80% identical thereto (e.g., about 82%, about 85%, about 88%, about 90%, about 93%, about 95%, about 97%, about, 98%, about 99%, or 100% sequence identity). In other embodiments, the single chain immunocytokine described herein can include an antibody heavy chain constant domain having the amino acid sequence set forth in SEQ ID NO:2, or an amino acid sequence that is at least about 80% identical thereto (e.g., about 82%, about 85%, about 88%, about 90%, about 93%, about 95%, about 97%, about, 98%, about 99%, or 100% sequence identity). In some embodiments, the immunoglobulin heavy chain included in the immunocytokine may also include a signal sequence, such as a signal sequence comprising SEQ ID NO: 3 or SEQ ID NO: 4. An exemplary anti-IL-2 heavy chain amino acid sequence, including a signal sequence, that may be included in the immunocytokine comprises SEQ ID NO: 5.

A single chain immunocytokine described herein (e.g., a single chain immunocytokine that can bind to an IL-2Rα/IL-2Rβ/γc polypeptide complex) can include any appropriate IL-2 protein (or fragment thereof) that can bind an IL-2Rα/IL-2Rβ/γc polypeptide complex. For example, the immunocytokine can include an IL-2 protein comprising the amino acid sequence of SEQ ID NO: 6, or an amino acid sequence that is at least about 80% identical thereto (e.g., about 82%, about 85%, about 88%, about 90%, about 93%, about 95%, about 97%, about, 98%, about 99%, or 100% sequence identity).

Figure 2:
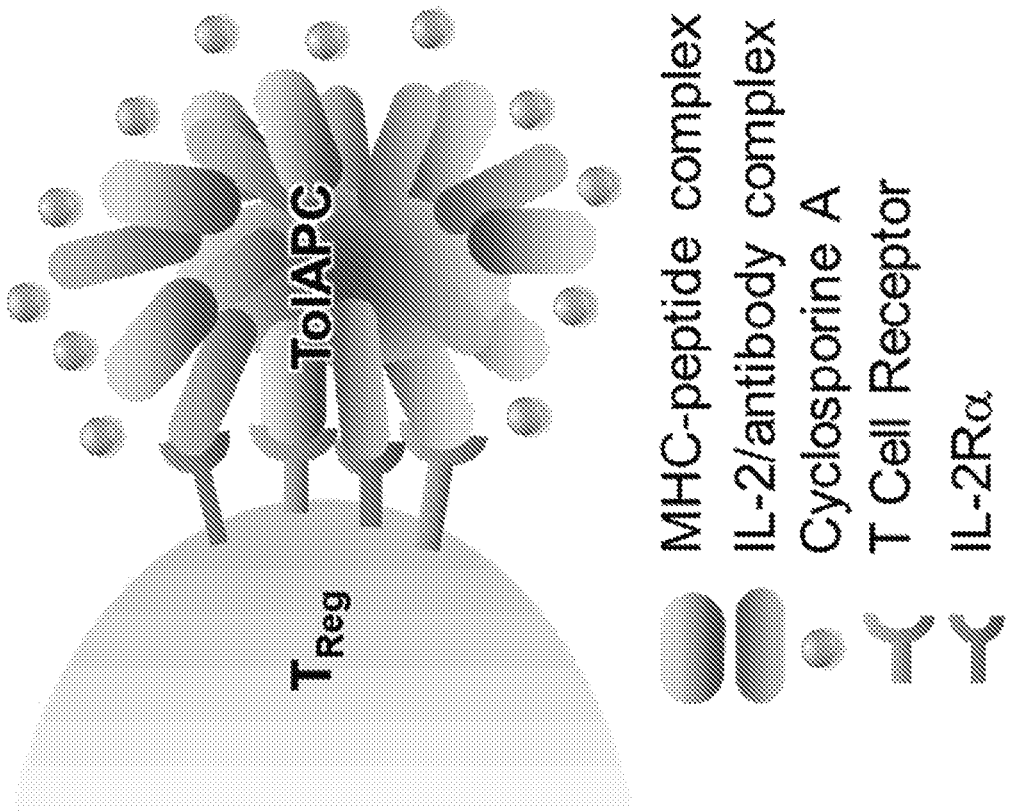
FIG. 2 is a schematic showing the design of TolAPCs. Shown is a layout of an engineered nanoparticle (NP) that selectively expands antigen-specific $T_{Reg}$ cells and releases immunosuppressive drug.

Examples of antibodies whose light chain variable domain and/or constant domains can be used in the single chain immunocytokine described herein include, without limitation, monoclonal antibody F5111.7 light chains, monoclonal antibody F5111.8 light chains, and monoclonal antibody F5111.2 light chains. Other immunoglobulins whose light chain variable domains and/or constant domains can be used in the single chain immunocytokine described herein also are described in, e.g., Trotta et al., *Nat Med.,* 24(7): 1005-1014 (2018)). The single chain immunocytokine described herein may include an antibody light chain variable domain having the amino acid sequence set forth in SEQ ID NO: 7, or an amino acid sequence that is at least about 80% identical thereto (e.g., about 82%, about 85%, about 88%, about 90%, about 93%, about 95%, about 97%, about, 98%, about 99%, or 100% sequence identity). In other embodiments, the single chain immunocytokine described herein can include an antibody light chain constant domain having the amino acid sequence set forth in SEQ ID NO: 8, or an amino acid sequence that is at least about 80% identical thereto (e.g., about 82%, about 85%, about 88%, about 90%, about 93%, about 95%, about 97%, about, 98%, about 99%, or 100% sequence identity). In some embodiments, the immunoglobulin heavy chain included in the immunocytokine may also can include a signal sequence, such as a signal sequence comprising SEQ ID NO: 4 or SEQ ID NO: 9. An exemplary anti-IL-2 light chain amino acid sequence, including a signal sequence, that may be included in the immunocytokine comprises SEQ ID NO: 10. An exemplary TolAPC comprising an immunocytokine is schematically depicted in FIG. 2.

In certain embodiments, the IL-2 protein (or fragment thereof) portion of the immunocytokine can be fused to the immunoglobulin light chain (e.g., the immunoglobulin light chain variable domain) portion of the immunocytokine. In such cases, the IL-2 protein (or fragment thereof) and the immunoglobulin light chain variable domain can be fused via a linker. Any suitable linker of any suitable size may be used. In some cases, a linker can be flexible (e.g., to allow for intramolecular interaction(s)). The linker may be a peptide linker. A peptide linker can include any appropriate number of amino acids. For example, a peptide linker can comprise from about 10 amino acids to about 60 amino acids (e.g., about 15, 20, 25, 30, 35, 40, 45, 50, or 55 amino acids). The linker may comprise any appropriate amino acids, but desirably comprises one or more glycine (Gly) and one or more serine (Ser) residues. For example, the linker may be a (Gly$_4$Ser)$_3$ linker. An exemplary fusion protein amino acid sequence comprising a signal sequence, human IL-2 protein, a linker, and anti-IL-2 light chain variable and constant regions is set forth in SEQ ID NO: 11.

The biodegradable particle may further comprise a third soluble protein or small molecule encapsulated within the particle. Exemplary proteins that may be encapsulated within the biodegradable particle includes interleukins and cytokines, such as the transforming growth factor (TGF) beta family of cytokines, including TGF-β1, TGF-β2, TGF-β3, and TGF-β4. Representative interleukins include, but are not limited to, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, and IL-37.

In some embodiments, the biodegradable particle comprises a small molecule encapsulated within the particle. The small molecule may be any suitable small molecule, such as, for example, an immunosuppressive drug. Examples of immunosuppressive drugs include, but are not limited to, rapamycin, cyclosporine A, or analogs thereof. Small molecule immunosuppressive drugs are described in further detail in, e.g., Fantini et al., *Nature Clinical Practice Gastroenterology & Hepatology,* 3: 633-644 (2006)). Rapamycin and its analogs (i.e., "rapalogs") inhibit activation of T cells and B cells by reducing their sensitivity to IL-2 through mammalian target of rapamycin (mTOR) inhibition. Representative analogs of rapamycin include, but are not limited to temsirolimus (a prodrug of rapamycin), everolimus, and ridaforolimus.

In some embodiments, the particle has a coating comprising one or more synthetic and/or natural lipids and/or lipid membranes. In particular embodiments, at least two types of protein are attached to the coating comprising one or more synthetic and/or natural lipids and/or lipid membranes. In other particular embodiments, at least one type of protein is attached to the coating comprising one or more synthetic and/or natural lipids and/or lipid membranes. Representative lipids suitable for use in coating the presently disclosed particles include, but are not limited to, fatty acids, glycerolipids, glycerophospholipids, sphingolipids, sterol lipids, prenol lipids, saccharolipids, and polyketides.

Kits

In other embodiments, the disclosure provides a kit comprising the presently disclosed T-aAPC. In general, a kit contains some or all of the components, reagents, supplies, and the like to practice a method according to the presently disclosed subject matter. In some embodiments, the term "kit" refers to any intended article of manufacture (e.g., a package or a container) comprising the disclosed biodegradable particle formulation. In some embodiments, the kit can be packaged in a divided or undivided container, such as a carton, bottle, ampule, tube, etc. The disclosed biodegradable particle, or compositions comprising same, can be packaged in dried, lyophilized, or liquid form. Additional components provided can include vehicles for reconstitution of dried components. Preferably all such vehicles are sterile and apyrogenic so that they are suitable for injection into a patient without causing adverse reactions. The kit can further include instructions for use.

Methods of Treating an Autoimmune Disease

The disclosure also provides method for treating a disease or condition in subject in need of treatment thereof, as well as a method for modulating an immune response in a subject, which comprises administering to the subject a therapeutically effective amount of the biodegradable particle described herein. The presently disclosed TolAPCs can be useful for treating multiple autoimmune diseases in a modular, flexible way. For example, in type 1 diabetes (T1D), incorrect information is sent to target immune cells, generating an autoimmune response that destroys pancreatic islet β cells. To alleviate this disease, the presently disclosed biodegradable particles can be designed as artificial, synthetic cells to reprogram the immune response to not attack and actively defend the pancreatic islet β cells. Selective induction and expansion of these diabeto-protective $T_{Regs}$ will allow them to act as an army of protectors to effectively shield the pancreatic islet β cells from harm to allow for normal and healthy insulin production.

More generally, the disease or condition to be treated can be immune disorder. As used herein, the term "immune disorders" includes diseases involving the immune system that can include but not be limited to allergies, autoimmune diseases, immune complex diseases, immunodeficiency diseases and cancers of the immune system. Autoimmunity is the failure of an organism to recognize its own constituent parts (down to the sub-molecular levels) as "self," which results in an immune response against its own cells and tissues. Any disease that results from such an aberrant immune response is termed an autoimmune disease. An unwanted immune response may be, for example, immune responses associated with an autoimmune disorder, transplants, allergies, or inflammatory disorders.

Exemplary autoimmune diseases and disorders that may be treated with the presently disclosed methods include, for example, inflammatory responses, such as inflammatory skin diseases, including psoriasis and dermatitis (e.g., atopic dermatitis); dermatomyositis; systemic scleroderma and sclerosis: responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions, such as eczema and asthma, and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitus); multiple sclerosis; Reynaud's syndrome; autoimmune thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Bechet disease; giant cell arteritis; immune complex nephritis; IgA nephropathy; IgM polyneuropathies; immune thrombocytopenic purpura (ITP) or autoimmune thrombocytopenia and autoimmune hemolytic diseases, Hashimoto's thyroiditis, Wegener's granulomatosis, cold agglutinin disease associated with indolent lymphoma, acquired factor VIII inhibitors disease, and the like.

The term "chronic inflammatory diseases" may include but not be limited to Tuberculosis, Chronic cholecystitis, Bronchiectasis, ulcerative colitis, silicosis and other pneumoconiosis, as well as the above listed autoimmune diseases.

In particular embodiments, the disease or condition is diabetes. In yet more particular embodiments, the disease or condition is type 1 diabetes. In other embodiments, the presently disclosed TolAPCs can be useful for preventing rejection in transplantation. Thus, in such embodiments, the subject to be treated is an organ transplant recipient or a subject who is treated in advance of becoming an organ transplant recipient.

In yet more particular embodiments, the presently disclosed subject matter provides a method for modulating an immune response in a subject, the method comprising administering an effective amount of a presently disclosed biodegradable particle. In certain embodiments, the subject is afflicted with an autoimmune disease.

As used herein, the term "treating" can include reversing, alleviating, inhibiting the progression of, preventing or reducing the likelihood of the disease, disorder, or condition to which such term applies, or one or more symptoms or manifestations of such disease, disorder or condition. Preventing refers to causing a disease, disorder, condition, or symptom or manifestation of such, or worsening of the severity of such, not to occur. Accordingly, the disclosed compounds can be administered prophylactically to prevent or reduce the incidence or recurrence of the disease, disorder, or condition.

In general, the "effective amount" of an active agent refers to the amount necessary to elicit the desired biological response. As will be appreciated by those of ordinary skill in this art, the effective amount of an agent may vary depending on such factors as the desired biological endpoint, the agent to be delivered, the composition of the encapsulating matrix, the target tissue, and the like. As used herein, a "dose" refers to the amount of TolAPC administered to a subject that is sufficient to treat the subject for a disease, disorder, or dysfunction.

An "immune response" can entail, for example, antibody production and/or the activation of immune effector cells (e.g., T cells).

In the various embodiments described above, the TolAPC can be administered in a variety of forms depending on the desired route and/or dose. The TolAPC can be administered in a pharmaceutically acceptable carrier. As used herein, "pharmaceutically acceptable carrier" is intended to include, but is not limited to, water, saline, dextrose solutions, human serum albumin, liposomes, hydrogels, microparticles and nanoparticles.

Depending on the specific conditions being treated, the TolAPCs may be formulated into liquid or solid dosage forms and administered systemically or locally. The agents may be delivered, for example, in a timed- or sustained-low release form as is known to those skilled in the art. Techniques for formulation and administration may be found in *Remington: The Science and Practice of Pharmacy* (20th ed.) Lippincott, Williams & Wilkins (2000). Suitable routes may include oral, buccal, inhalation, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, intraocular injections, or other modes of delivery.

While the form and/or route of administration can vary, in some embodiments the TolAPC or pharmaceutical composition is administered parenterally (e.g., by subcutaneous, intravenous, or intramuscular administration), or in some embodiments is administered directly to the lungs. Local administration to the lungs can be achieved using a variety of formulation strategies including pharmaceutical aerosols, which may be solution aerosols or powder aerosols. Powder formulations typically comprise small particles. Suitable particles can be prepared using any means known in the art, for example, by grinding in an airjet mill, ball mill or vibrator mill, sieving, microprecipitation, spray-drying, lyophilization or controlled crystallization. Typically, particles will be about 10 microns or less in diameter. Powder formulations may optionally contain at least one particulate pharmaceutically acceptable carrier known to those of skill in the art. Examples of suitable pharmaceutical carriers include, but are not limited to, saccharides, including monosaccharides, disaccharides, polysaccharides and sugar alcohols such as arabinose, glucose, fructose, ribose, mannose, sucrose, trehalose, lactose, maltose, starches, dextran, mannitol or sorbitol. Alternatively, solution aerosols may be prepared using any means known to those of skill in the art, for example, an aerosol vial provided with a valve adapted to deliver a metered dose of the composition. Where the inhalable form of the active ingredient is a nebulizable aqueous, organic or aqueous/organic dispersion, the inhalation device may be a nebulizer, for example a conventional pneumatic nebulizer such as an airjet nebulizer, or an ultrasonic nebulizer, which may contain, for example, from 1 mL to 50 mL, commonly 1 mL to 10 ml, of the dispersion; or a hand-held nebulizer which allows smaller nebulized volumes, e.g. 10 μL to 100 μL.

For injection, the disclosed biodegradable particles may be formulated and diluted in aqueous solutions, such as in physiologically compatible buffers (e.g., Hank's solution, Ringer's solution, or physiological saline buffer).

Use of pharmaceutically acceptable inert carriers to formulate the compounds herein into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances such as, saline, preservatives, such as benzyl alcohol, absorption promoters, and fluorocarbons.

The "subject" treated by the disclosed methods is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals such as, but not limited to, primates (e.g., humans, monkeys, apes, etc.); bovines (e.g., cattle, oxen, etc.); ovines (e.g., sheep); caprines (e.g., goats); porcines (e.g., pigs, hogs, etc.; equines (e.g., horses, donkeys, zebras, etc.); felines, including wild and domestic cats; canines, including dogs; lagomorphs (e.g., rabbits, hares, etc.); and rodents (e.g., mice, rats, etc.). An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Materials and Methods

Protein expression and purification. The published variable heavy and light chain sequences ($V_H$ and $V_L$) of F5111 were used to formulate the recombinant antibody on the human immunoglobulin (IgG) 1 lambda isotype platform.

The heavy chain (HC) and light chain (LC) of the F5111 antibody were separately cloned into the gWiz vector (Genlantis). Antibodies were expressed recombinantly in human embryonic kidney (HEK) 293F cells via transient cotransfection of plasmids encoding the HC and LC. HC and LC plasmids were titrated in small-scale cotransfection tests to determine optimal ratios for large-scale expression. Secreted antibodies were purified from cell supernatants 5 days post-transfection via protein G affinity chromatography followed by size-exclusion chromatography on a Superdex 200 column (GE Healthcare) on an FPLC instrument, equilibrated in HEPES buffered saline (HBS, 150 mM NaCl in 10 mM HEPES pH 7.3). Purity (>99%) was verified by SDS-PAGE analysis. For immunocytokine (IC) production, the human IL-2 (hIL-2) cytokine was fused to the full F5111 antibody at the N-terminus of the LC, connected by either a flexible 15-amino acid $(Gly_4Ser)_3$ linker (LN15), 25-amino acid $(Gly_4Ser)_5$ linker (LN25), or a 35-amino acid $(Gly_4Ser)_7$ linker (LN35) to allow for intramolecular interaction. Separate plasmids were prepared in the gWiz vector (Genlantis) encoding the F5111 HC and the hIL-2-fused F5111 LC. ICs were expressed and purified via transient co-transfection of HEK 293F cells, as described for the F5111 antibody.

The full hIL-2 cytokine (residues 1-133) and the extracellular domains of the hIL-2Rα (residues 1-214) and hIL-2Rβ (residues 1-214) receptor subunits were cloned into the gWiz vector (Genlantis) with a C-terminal hexahistidine tag. Proteins were expressed via transient transfection of HEK 293F cells, as described for HEK, and purified via Ni-NTA affinity chromatography followed by size-exclusion chromatography on a Superdex 200 column (GE Healthcare) on an FPLC instrument, equilibrated in HBS. Purity (>99%) was verified by SDS-PAGE analysis.

For expression of biotinylated hIL-2Rα and hIL-2Rβ, protein containing a C-terminal biotin acceptor peptide (BAP)-LNDIFEAQKIEWHE was expressed and purified via Ni-NTA affinity chromatography and then biotinylated with the soluble BirA ligase enzyme in 0.5 mM Bicine pH 8.3, 100 mM ATP, 100 mM magnesium acetate, and 500 mM biotin (Sigma). Excess biotin was removed by size exclusion chromatography on a Superdex 200 column (GE Healthcare) on an FPLC instrument, equilibrated in HBS.

Cell lines. HEK 293F cells were cultivated in Freestyle 293 Expression Medium (Thermo) supplemented with 0.01% penicillin-streptomycin (Gibco). Unmodified YT-136 and IL-2Rα+ YT-1 human natural killer cells (Kuziel et al., J. Immunol., 150(8): 3357-3365 (1993)) were cultured in RPMI complete medium (RPMI 1640 medium supplemented with 10% fetal bovine serum, 2 mM L-glutamine, minimum non-essential amino acids, sodium pyruvate, 25 mM HEPES, and penicillin-streptomycin [Gibco]) and maintained at 37° C. in a humidified atmosphere with 5% $CO_2$.

The subpopulation of YT-1 cells expressing IL-2Rα was purified via magnetic selection as described previously (Ring et al., Nat. Immunol., 13(12): 1187-1195 (2012)). Ten million unsorted IL-2Rα+ YT-1 cells were washed with FACS buffer (phosphate-buffered saline (PBS) pH 7.2 containing 0.1% bovine serum albumin) and incubated in FACS buffer with PE-conjugated antihuman IL-2Rα antibody (Biolegend, clone BC96) for 2 hours at 4° C. PE-labeled IL-2Rα+ cells were then incubated with paramagnetic microbeads coated with an anti-PE IgG for 20 min at 4° C., washed once with cold FACS buffer, and sorted on an LS MACS separation column (Miltenyi Biotec) according to the manufacturer's protocol. Purified eluted cells were re-suspended and grown in RPMI complete medium. Enrichment of IL-2Rα+ cells was evaluated using a CytoFLEX flow cytometer (Beckman Coulter) and persistence of IL-2Rα expression was monitored by PE-conjugated anti-human IL-2Rα antibody (Biolegend) labeling and flow cytometric analysis of sorted IL-2Rα+ YT-1 cells.

Yeast surface binding studies. For antibody binding studies on yeast, hIL-2 (residues 1-133) or mIL-2 (residues 1-149) were cloned into the pCT302 vector and presented on the surface of yeast, as described previously (Boder et al., Nat. Biotechnol., 15(6): 553-557 (1997)). Yeast displaying human or mouse IL-2 were incubated in PBSA containing serial dilutions of recombinant F5111 antibody for 2 hours at room temperature. Cells were then washed and stained with a 1:200 dilution of Alexa647-conjugated streptavidin (Thermo) in PBSA for 15 minutes at 4° C. After a final wash, cells were analyzed for antibody binding using a CytoFLEX flow cytometer (Beckman Coulter). Background-subtracted and normalized binding curves were fitted to a first-order binding model and equilibrium dissociation constant (KD) values were determined using GraphPad Prism. Studies were performed three times with similar results.

Bio-layer interferometry binding studies. For IL-2 versus immunocytokine affinity titration studies, biotinylated human IL-2 cytokine or IL-2Rα or IL-2Rβ receptor chains were immobilized to streptavidin-coated tips for analysis on an OCTET® Red96 bio-layer interferometry (BLI) instrument (ForteBio). Less than 5 signal units (nm) of receptor was immobilized to minimize mass transfer effects. Tips were exposed to serial dilutions of hIL-2, IL-2/F5111 complex, or single-chain IL-2/F5111 IC constructs in a 96-well plate for 300 seconds and dissociation was measured for 600 seconds. An irrelevant protein was included in a reference well to subtract non-specific binding. Surface regeneration for all interactions was conducted using a 15 second exposure to 0.1 M glycine pH 3.0. Experiments were carried out in PBSA (phosphate-buffered saline, pH 7.3 plus 0.1% bovine serum albumin (BSA, Thermo Fisher Scientific)) at 25° C. Data was visualized and processed using the Octet® Data Analysis software version 7.1 (Molecular Devices). Equilibrium titration curve fitting and KD value determination was implemented using GraphPad Prism, assuming all binding interactions to be first order. Experiments were reproduced two times with similar results.

YT-1 cell STAT5 phosphorylation studies. Approximately $2\times10^5$ IL-2Rα− YT-1 or IL-2Rα+ YT-1 cells were plated in each well of a 96-well plate and re-suspended in RPMI complete medium containing serial dilutions of the indicated treatments. Cytokine/antibody complexes were formed by incubating a 1:1 molar ratio of F5111 antibody to hIL-2 for 1 hour at 37° C. Cells were stimulated for 20 minutes at 37° C. and immediately fixed by addition of formaldehyde to 1.5% and 10 minute incubation at room temperature. Permeabilization of cells was achieved by resuspension in ice-cold 100% methanol for 30 minutes at 4° C. Fixed and permeabilized cells were washed twice with FACS buffer (phosphate-buffered saline [PBS] pH 7.2 containing 0.1% BSA [Thermo Fisher Scientific]) and incubated with Alexa Fluor® 647-conjugated anti-STAT5 pY694 (BD Biosciences) diluted in FACS buffer for 2 hours at room temperature. Cells were then washed twice in FACS buffer and mean fluorescence intensity (MFI) was determined on a Cyto-FLEX flow cytometer (Beckman-Coulter). Dose-response curves were fitted to a logistic model and half-maximal effective concentrations ($EC_{50s}$) were calculated using GraphPad Prism data analysis software after subtraction of the mean fluorescence intensity (MFI) of unstimulated cells and normalization to the maximum signal intensity. Experiments were conducted in triplicate and performed three times with similar results.

Human PBMC STAT5 phosphorylation studies. Human PBMCs were isolated from whole blood of healthy donors via Ficoll gradient following manufacturer protocols and then incubated with ACK lysis buffer for removal of red blood cells. Approximately $1\times10^6$ human PBMCs were plated in each well of a 96-well plate and re-suspended in RPMI complete medium containing serial dilutions of the indicated treatments. Cytokine/antibody complexes were formed by incubating a 1:1 molar ratio of F5111 antibody to hIL-2 for 1 hour at 37° C. Cells were stimulated for 20 minutes at 37° C. and immediately fixed by addition of 1X Fix/Perm Buffer (BD Biosciences) and 50 minute incubation at 4° C. Permeabilization of cells was achieved by resuspension in Perm Buffer III (BD Biosciences) overnight at −20° C. Fixed and permeabilized cells were washed twice with FACS buffer (phosphate buffered saline [PBS] pH 7.2 containing 0.1% BSA [Thermo Fisher Scientific]) and incubated with an appropriate panel of antibodies (for human PBMCs: anti-CD3, anti-CD4, anti-CD8, anti-FOXP3, anti-CD25, anti-CD127, and anti-phosphorylated STAT5) diluted in FACS buffer for 2 hours at room temperature. Cells were then washed twice in FACS buffer and MFI was determined on a CytoFLEX flow cytometer (Beckman-Coulter). Dose-response curves were fitted to a logistic model and half-maximal effective concentrations (EC50s) were calculated using GraphPad Prism data analysis software after subtraction of the mean fluorescence intensity (MFI) of unstimulated cells and normalization to the maximum signal intensity. Experiments were conducted in triplicate and performed two times with similar results.

Manufacturing and characterization of TolAPCs coated with MC-peptide complexes and immunocytokines. PLGA/PBAE particles were fabricated via standard emulsion methods. PLGA (50:50 copolymer ratio; 46 kDa MW) was blended with PBAE at a 75/25 mass ratio, and this blend was dissolved in dichloromethane (DCM). The polymer solution was emulsified in a poly(vinyl alcohol) (PVA) solution to create a single emulsion. Particles were hardened for 4 hours, washed, and lyophilized. To prepare TolAPCs, EDC/NHS chemistry was used to couple the carboxylic acid-terminated PLGA to primary amines on one of two tetramer MHC-peptide complexes: (i) the BDC12-4.1 mimotope mouse Insulin B peptide (B9:23) variant pE8, denoted Bpep, loaded in the I-A(b) Class II MHC protein (Crawford et al., Proc. Natl. Acad. Sci. USA, 108(40): 16729-16734 (2011); or (ii) the chicken ovalbumin peptide (329-337), denoted Ova, loaded in the I-A(b) Class II MHC protein. Both peptide-MHC complexes were obtained from the NIH Tetramer Core Facility, and were described previously (Meyer et al., Small, 11(13):1519-1525 (2015). EDC/NHS chemistry was also used to coat the particle surface with protein G, which binds the Fc region on proteins of interest. Tetramer- and protein G-functionalized particles were then incubated with IC to generate two TolAPC formulations: TolAPCBpep and TolAPCChrA that present correctly oriented proteins on their surface. Similarly, TolAPCCon particles were produced that contained MHCs loaded with an irrelevant peptide. Surface protein conjugation efficiency and density on the TolAPC surface was measured by conjugating fluorescently-labeled peptides and ICs and measuring fluorescence intensity with a Biotek plate reader, and the protein incubation concentrations were adjusted so that all TolAPCs displayed the desired protein amount on their surface (protein density to be optimized, with 0.2 µg/mg protein as the initial standard amount). Particle size was analyzed via a LEO field-emission scanning electron microscope (SEM) and Hitachi 7600 transmission electron microscope (TEM), and surface charge and size were measured via Malvern Zetasizer.

In vivo immune cell subset expansion studies in mice. Microparticles coated with IC (1 mg dose per mouse) were injected into NOD mice for 4 consecutive days via intravenous (i.v.) or intranodal (i.n.) injection. Mice were sacrificed 24 hours after the final injection and spleens and lymph nodes were harvested. Single-cell suspensions were prepared by mechanical homogenization, and treated with ACK lysis buffer to remove red blood cells. Absolute cell counts for each organ were assessed for each spleen by automated cell counter (Vi-CELL; Beckman Coulter). Cells were resuspended in PBS and subsequently stained for 30 minutes on ice with fluorophore-conjugated anti-mouse antibodies for phenotyping of $T_{Reg}$ (CD4$^+$IL-2R$\alpha^+$Foxp3$^+$) or CD8$^+$ effector T cells (CD8$^+$) using BV605-conjugated anti-CD4 (clone RM4-5; BioLegend), PeCy7-conjugated anti-IL-2R$\alpha$ (clone PC61.5; eBioscience), and PerCP-Cy5.5-conjugated anti-CD8 (clone 53-6.72; eBioscience) antibodies. Fixable Blue Dead Cell Stain Kit (Life Technologies) was used to assess live cells. Cells were then washed twice with FACS buffer (1% BSA, 1% sodium azide) and fixed in Foxp3 Transcription Factor Fixation/Permeabilization Buffer (eBioscience) for 30 minutes on ice. After two washes in Permeabilization Buffer (eBioscience), $T_{Reg}$ cells were stained with FITC-conjugated anti-mouse/rat Foxp3 antibody (clone FJK-16s; eBioscience) for 1 hour on ice. Two final washes were conducted in Permeabilization Buffer, and cells were resuspended in FACS buffer for flow cytometric analysis on CytoFLEX flow cytometry (Beckman Coulter). Data were analyzed using FlowJo X software (Tree Star). Ratios of the absolute numbers of $T_{Reg}$ cells to either CD8$^+$ effector T cells or total CD4$^+$ T cells are presented. Statistical significance was determined by two-tailed un-paired Student t-test. Experiments were performed three times with similar results.

Encapsulation of F5111 IC LN35, TGF-β, and rapamycin into MPs. To synthesize F5111 IC-loaded microparticles, 25 µg F5111 IC was diluted into 500 µL of a 5 mM NaCl solution (unless otherwise indicated). 20 mg of polymer was dissolved in 5 mL dichloromethane. F5111 IC solution was added dropwise to the polymer solution during sonication to generate the first emulsion. The polymer solution was then homogenized into a 2% PVA solution to generate the second emulsion, and subsequently diluted into a 1% PVA solution. TGF-β was loaded into particles using the same technique, except 2.5 µg TGF-β was diluted into 200 µL of a 5 mg/mL BSA solution in diH$_2$O. To synthesize rapamycin-loaded particles, rapamycin was added at indicated amounts to the polymer solution in dichloromethane. Particles were then synthesized using single or double emulsion techniques.

Experimental autoimmune encephalomyelitis (EAE) mouse model. Four milligrams of blank (unconjugated) MPs or TolAPCs surface-conjugated with F5111 IC LN15 and tetramer loaded with myelin oligodendrocyte glycoprotein (MOG) peptide [I-A(b) mouse MOG 38-49] were injected into the inguinal lymph nodes of female C57BL/6 mice (9 weeks old) (2 mg per lymph node) on t=−1 day. Mice were also administered 4 mg MPs or TolAPCs intravenously on t=1 day. EAE was induced by subcutaneous injection of an emulsion of MOG peptide and complete Freund's adjuvant (MOG/CFA) on t=0 and intraperitoneal injection of 100 ng pertussis toxin (PTX) on t=0 and t=1 day, according to instructions from the kit manufacturer (Hooke Laboratories, Lawrence, MA). Starting from t=7 days until euthanasia at t=28 days, mice were scored according to severity of disease following the manufacturer's protocol.

Melanoma tumor protection mouse model. Four milligrams of TolAPCs were injected into the inguinal lymph nodes of female C57BL/6 mice (9 weeks old) (2 mg per lymph node) on t=−1 day. TolAPCs consisted of iron dextran microbeads surface-conjugated with (1) tetramer loaded with ovalbumin (ova) peptide (I-A(b) chicken ova 329-337); (2) F5111 IC LN25; (3) ova tetramer and F5111 IC LN25; or (4) nothing (blank) on t=−1 day. On t=0, $5\times10^5$ MC38-ova murine colorectal cancer cells were injected subcutaneously on the flank of each mouse. Tumor size was measured over time to determine the ability of TolAPCs to protect tumors from rejection. Mice were euthanized either when tumors reached 200 mm$^2$ or when tumors ulcerated.

Example 1

This example demonstrates the production of an immunocytokine comprising the F5111 antibody and IL-2 in mammalian cells.

Figure 3:
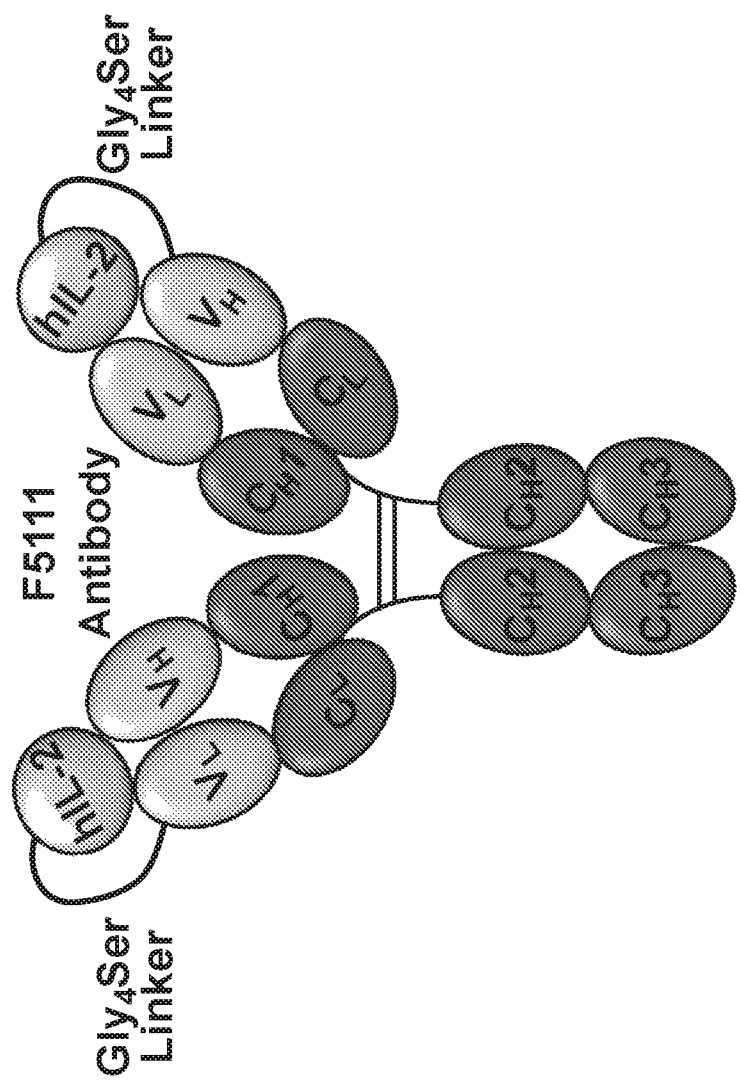
FIG. 3 is a schematic of the design of the IL-2/F5111 single chain fusion protein (immunocytokine). Human IL-2 is fused to the N-terminus of the F5111 antibody light chain.

To combine the potency of cytokines with the pharmacokinetically favorable properties of antibodies in a targeted fashion, human IL-2 (hIL-2) was fused to the cytokine-biasing F5111 antibody to create an immunocytokine (IC) (FIG. 3). A rapid small-scale HEK 293F cell transfection assay was developed to optimize immunocytokine expression. Cells were transfected in 6-well plates with predefined ratios of heavy chain (HC) and IL-2-fused light chain (LC) plasmid DNA. After a 3-day incubation, secreted protein was captured from the supernatant with protein G resin, eluted with 0.1 M glycine pH 2.0, and analyzed via SDS-PAGE. This assay was validated using an immunocytokine comprised of hIL-2 fused to the full-length F5111 human IgG1 lambda antibody at the LC N-terminus, connected by either a flexible 15-amino acid (Gly$_4$Ser)$_3$ linker (LN15), 25-amino acid (Gly$_4$Ser)$_5$ linker (LN25), or a 35-amino acid (Gly$_4$Ser)$_7$ linker (LN35). Titration of the HC:LC ratio revealed the optimal expression conditions. Immunocytokine expression was scaled up in HEK 293F cells and the secreted protein was purified via protein G affinity chromatography followed by size-exclusion chromatography. F5111 IC constructs were purified to homogeneity on an FPLC instrument (FIG. 4A), and purity was verified via SDS-PAGE analysis (FIG. 4B). To verify binding of the recombinant F5111 antibody to the target hIL-2 cytokine, soluble antibody was titrated binding to yeast-displayed hIL-2 or mIL-2. As expected, the antibody bound hIL-2 with an apparent bivalent affinity of KD=430 pM. The antibody did not cross react with mIL-2 (FIG. 5).

Example 2

This example demonstrates that the recombinantly expressed single-chain IL-2/F5111 immunocytokine is properly assembled.

To demonstrate that hIL-2 is intramolecularly bound to the antibody within the IC, the binding affinity of F5111 IC LN15 for hIL-2 was measured and compared to F5111 antibody (Ab). The binding of purified F5111 antibody and IC to yeast surface-displayed hIL-2, as measured by flow cytometry, is shown in FIG. 6A. The binding affinities were also evaluated using bio-layer interferometry on an OCTET® instrument with biotinylated hIL-2 immobilized on a streptavidin-coated tip (FIG. 6B). For both yeast surface and bio-layer interferometry studies, a significant reduction in binding affinity was observed for F5111 IC LN15 relative to F5111 Ab, confirming intramolecular cytokine/antibody assembly. Bio-layer interferometry based binding studies were also conducted to assess the interaction between F5111 IC LN15 and the IL-2Rα and IL-2Rβ receptor chains, to ensure that the single-chain antibody/cytokine fusion was biased toward engagement of IL-2Rα (which is highly expressed on $T_{Reg}$ cells but not effector cells) compared with IL-2Rβ. Indeed, biophysical assessment showed that F5111 IC LN15 bound IL-2Rα with equal potency to the free IL-2 cytokine (FIG. 7A), whereas F5111 IC LN15 exhibited significantly impaired binding to IL-2Rβ relative to the free IL-2 cytokine (FIG. 7B). These data corroborate the proper folding, intramolecular binding, and activity of the IC.

Example 3

This example demonstrates that the immunocytokine selectively biases IL-2 signaling.

IL-2 signals through activation of signal transducer and activator of transcription 5 (STAT5), which translocates to the nucleus to effect transcriptional programs (Murray, P. J. *J Immunol Baltim Md* 1950, 178(5): 2623-2629 (2007); and Bromberg, J., and Wang, T. C., *Cancer Cell,* 15(2): 79-80 (2009)). To characterize IC variant-mediated immune bias, the YT-1 NK cell line was employed (Yodoi et al., *J Immunol Baltim Md* 1950, 134(3): 1623-1630 (1985), which inducibly expresses IL-2Rα (Kuziel et al., supra). Flow cytometry-based studies were performed to quantify STAT5 signaling elicited by IL-2, the IL-2/F5111 complex, and F5111 variants on induced IL-2Rα$^+$ versus uninduced IL-2Rα$^-$ YT-1 cells as a surrogate for $T_{Reg}$ versus effector cell activation. Untethered IL-2 signals on both IL-2Rα$^+$ and IL-2Rα$^-$ cells, and IL-2/F5111 complex, fully activated IL-2Rα$^+$ cells and exhibited only mildly impaired activity on IL-2Rα$^-$ cells and no activity on IL-2Rα$^-$ cells. In contrast, F5111 IC LN15 activity was only mildly impaired on IL-2Rα$^+$ cells, but its activity was dramatically reduced on IL-2Rα$^-$ cells.

These results indicate that the F5111 immunocytokine effectively biases IL-2 activity toward $T_{Reg}$ cells over immune effector cells, even more effectively than the mixed IL-2/F5111 complex (FIG. 8).

Example 4

This example demonstrates that coated nanoparticles can stimulate $T_{Reg}$ cells.

To establish proof of concept for the TolAPC approach, successful stimulation of $T_{Reg}$ cells was demonstrated using conjugated nanoparticles. As a preliminary demonstration, aAPCs were synthesized conjugated with a polyclonal T cell stimulator (anti-CD3 and anti-CD28 antibodies) and encapsulating a tolerogenic agent (TGF-β) for sustained local release. These early particle-based formulations engaged and stimulated T cells polyclonally and significantly increased the polarization of primary T cells to a $T_{Reg}$ phenotype. These polarized $T_{Reg}$ cells were in turn able to suppress the proliferation of potentially pathogenic cytotoxic T cells. It was also shown that these early particle-based formulations effectively expanded $T_{Reg}$ cells in both the spleens and lymph nodes of treated mice (FIG. 9). Through these results, it was also discovered that particles fabricated from a novel combination of biodegradable polymers (poly(lactic-co-glycolic acid) [PLGA] and poly(beta-amino ester) [PBAE]) at a 75:25 mass ratio resulted in enhanced capacity to engage and program T cells. These studies also demonstrated the potential of engineered artificial cells to treat autoimmune disease by concomitantly presenting peptide-loaded MHC molecules and the disclosed engineered $T_{Reg}$-biased ICs, as MHC-peptide complexes will promote the engagement of antigen-specific T cells, and single-chain IL-2/antibody ICs direct the selective delivery of IL-2 to IL-2R$\alpha^{High}$ $T_{Reg}$ cells, based on the molecular bias enacted by the component anti-cytokine antibodies. At the same time, the selectivity conferred by ICs caused other potentially autoreactive naïve T cells to receive only tolerogenic TCR signals (i.e., MHC-peptide engagement in the absence of co-stimulation), enhancing the regulation of self-antigen reactivity (Clemente-Casares et al., Nature, 530(7591): 434-440 (2016)). To further prevent the activation and expansion of disease-promoting effector T cells, the $T_{Reg}$ cell permissive immunosuppressive drug rapamycin (Raimondi et al., J Immunol Baltim Md 1950, 184(2): 624-636 (2010); and Turnquist et al., J Immunol., 178(11): 7018-7031 (2007)) can be encapsulated into TolAPCs, similar to an approach used previously (Jhunjhunwala et al., J Control Release Off J Control Release Soc., 133(3): 191-197 (2009))

Figure 11:
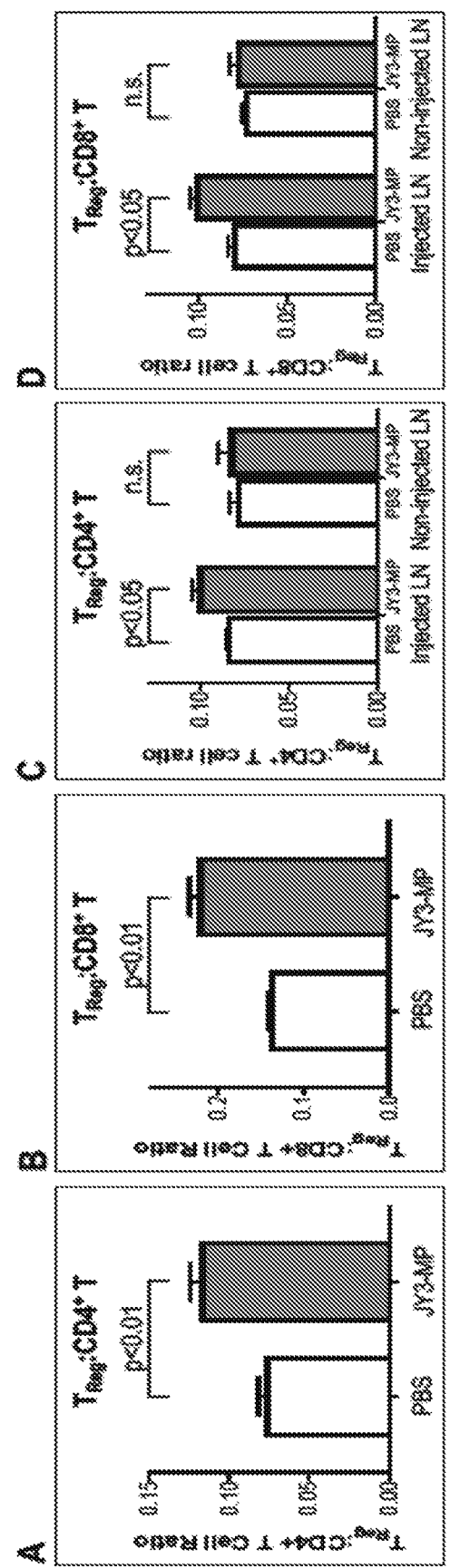

To further establish feasibility for the TolAPC platform, an IL-2/JES6-1 single chain IC (denoted JY3 or JY3 IC) was conjugated to PLGA/PBAE microparticles (MPs) without loss of function. In vitro coculture of bulk mouse CD4+ T cells with JY3 IC-coated MP and flow cytometry-based measurement of pSTAT5 induction demonstrated that JY3 IC-coated MPs specifically stimulate IL-2Ra$^+$Foxp3$^+$ $T_{Regs}$ over other populations of T cells both in vitro (FIG. 10) and in vivo (FIG. 11). Notably, increased TReg expansion following in vivo dosing of JY3 IC-coated MP was observed in the spleen of i.v.-injected animals and the injected lymph node but not a non-injected lymph node of i.n.-injected animals.

The results of this example reveal the ability for selective $T_{Reg}$ stimulation from the surface of particles, laying the foundation for development of TolAPCs.

Example 5

This example demonstrates that MHC tetramer-conjugated particles induce antigen-specific $T_{Reg}$ cell expansion.

As preliminary evidence of the potential to achieve antigen-specific activation with MHC-coated nanoparticles, MHCII tetramers carrying the OVA peptide were conjugated to the surface of nanoparticles. In particular, PLGA MPs conjugated with an OVA tetramer and an anti-CD28 antibody were incubated with naïve CD4+ T cells obtained from harvested spleens of OT-II mice (a transgenic strain with T cells specific for OVA) in the presence of IL-2 and soluble TGF-β. After 3 days, cells were stained for FoxP3 to evaluate $T_{Reg}$ cell induction via flow cytometry (a sign of successful engagement). MPs conjugated with the OVA tetramer and anti-CD28 antibody induced $T_{Reg}$ cells from a naïve OT-II CD4+ T cell pool in a dose-dependent manner, whereas MPs conjugated with a control tetramer did not induce $T_{Reg}$ cells (FIG. 12).

The results of this example demonstrate that an OVA tetramer on the surface of NPs can engage OVA-specific T cells, further supporting the utility of the TolAPC approach for induction of antigen-specific $T_{Reg}$ cells.

Example 6

This example describes the formulation and characterization of TolAPCs.

Building on the successful conjugation of both IC and MHC-peptide complexes to particles, an initial iteration of TolAPCs were synthesized. Specifically, microparticles (MPs) approximately 1 μm in diameter were fabricated from a 75:25 (w/w) blend of poly(lactic-co-glycolic acid) (PLGA) to poly(beta-amino ester) (PBAE). EDC/NHS chemistry was used to conjugate JY3 IC alone or a combination of the BDC12-4.1 mimotope mouse Insulin B peptide (B9:23) variant pE8 (InsB9:23) I-A(g7) (obtained from the NIH tetramer core) and JY3 IC to the surface of the particles to generate JY3 IC-MPs or TolAPCs. It was first verified that InsB tetramer conjugation efficiency was the same as that of a control I-A(g7) tetramer (FIG. 13A). A series of TolAPC variants were then synthesized by adding various amounts of InsB tetramer and JY3 IC to MPs activated with EDC/NHS. Ranges of 0.33-0.56 μg tetramer and 0.5-1.3 μg JY3 IC per mg of TolAPCs were measured (FIG. 13B). The maximum total protein conjugation efficiency was about 53%.

The TolAPC platform described above represents a significant advance for the treatment of autoimmune disease and for transplantation medicine by providing a safe, off-the-shelf therapeutic that activates $T_{Reg}$ cells directly in patients. The targeted nature of this platform circumvents the generalized immunosuppression that is observed with current clinical therapies, and the modular design of TolAPCs allows for substitution of any desired peptide-MHC specificity and for controlled release of other factors (in addition to rapamycin) that impact the migration and/or expansion of $T_{Reg}$ to maximize therapeutic performance (Dawson et al., Front Immunol., 8: 1460 (2017); and Bluestone, J. A. and Tang, Q. T., Science, 362(6411): 154-155 (2018)).

Example 7

This example describes experiments to optimize expression and function of the F5111 immunocytokine.

F5111 IC LN15 includes a 15-amino acid flexible linker between the C-terminus of hIL-2 and the N-terminus of the light chain of the F5111 antibody. Alternative F5111 IC constructs were designed substituting the 15-amino acid linker with a 25-amino acid linker (F5111 IC LN25) and a 35-amino acid linker (F5111 IC LN35). Expression of F5111 IC LN25 and LN35 was conducted in HEK 293F cells via transient co-transfection of plasmids encoding the F5111 heavy chain and the IL-2-fused F5111 light chain. The protein was purified from cell supernatants via protein G affinity chromatography followed by SEC on a fast protein liquid chromatography (FPLC) instrument. Three peaks were observed by SEC for F5111 IC LN25 and LN35 (labeled P1, P2, P3) and each peak was pooled for analysis. It was expected that since P1 and P2 elute earlier from the SEC column, they contain higher order oligomeric structures, whereas P3 represents the monomeric F5111 IC LN35 (FIG. 14A). The SEC traces for F5111 IC LN25 and LN35 were compared to the SEC trace for F5111 IC LN15 (FIG. 14B). As seen in FIG. 14B, most of the produced the F5111 IC LN15 was oligomerized, demonstrated by its coincident elution with P1 and P2 of F5111 IC LN25 and LN35 from the SEC column. Furthermore, P3 of F5111 IC LN25 and LN35 eluted at a volume close to the molecular weight of an antibody, suggesting that this peak consists of the monomeric IC. Therefore, P3 was used for evaluation in further experiments with F5111 IC LN25 and LN35, and references to F5111 IC LN25 and LN35 represent P3 unless otherwise specified. F5111 IC LN35 contained overall less oligomer compared to F5111 IC LN25. SDS-PAGE was performed to verify purity (>99%).

It was demonstrated that F5111 IC LN25 and LN35 selectively activate IL-2Rα$^+$ T$_{Reg}$-like cells over IL-2Rα$^-$ T effector (T$_{Eff}$)-like cells with greater bias than F5111 IC LN15 and the hIL-2/F5111 complex. A cell signaling assay was performed on YT-1 human NK cells with or without IL-2Rα. FIGS. 15A and 15B show STAT5 phosphorylation in response to hIL-2, hIL-2/F5111 complex, F5111 IC LN15, F5111 IC LN25, or F5111 IC LN35 on IL-2Rα$^+$ cells (FIG. 15A) or IL-2Rα$^-$ cells (FIG. 15B), as measured by flow cytometry. F5111 IC LN25 and LN35 activated IL-2Rα+ cells at sub-nanomolar concentrations, whereas the activity of F5111 IC LN25 and LN35 on IL-2Rα$^-$ cells was immeasurable.

Experiments were conducted to demonstrate that hIL-2 is intramolecularly bound to the antibody within the F5111 IC LN25 and LN35 and that the F5111 IC LN25 and LN35 selectively direct hIL-2 to T$_{Reg}$ cells by blocking the IL-2Rβ binding site to favor interaction with cells that express high levels of IL-2Rα. Binding interactions between IL-2 and F5111 IC LN25 and LN35 were evaluated using bio-layer interferometry on an Octet® instrument with biotinylated hIL-2 immobilized to streptavidin-coated tips (FIG. 16A). Additionally, binding interactions between F5111 IC LN25 and LN35 with the human IL-2Rα (hIL-2Rα) and hIL-2Rβ subunits were measured using bio-layer interferometry on an Octet® instrument by immobilizing biotinylated hIL-2Rα and IL-2Rβ on streptavidin-coated tips. As shown in FIG. 16B, F5111 IC LN25 and LN35 had similar binding affinities toward hIL-2Rα compared to free hIL-2, hIL-2/F5111 complex, and F5111 IC LN15. In contrast, there was a significant reduction in the binding affinity to hIL-2Rβ for the F5111 IC LN25 and LN35 compared to free hIL-2, hIL-2/F5111 complex and F5111 IC LN15, further illustrating the improved molecular bias of F5111 IC LN25 and LN35 compared to F5111 IC LN15 (FIG. 16B).

Immunocytokine activity was also interrogated on human PBMCs, isolated from healthy donor whole blood. STAT5 phosphorylation was measured to quantify activation of 3 cell populations: CD3$^+$CD8$^+$ cells (CD8$^+$ effector T cells) (FIG. 17A), CD3$^+$CD8$^+$CD25$^{High}$FOXP3$^{High}$ cells (T$_{Reg}$ cells) (FIG. 17B), and CD3$^+$CD8$^+$CD25$^{Low}$FOXP3$^{Low}$ cells (CD4$^+$ effector T cells) (FIG. 17C). F5111 IC LN35 demonstrated significantly more potent activation of CD3$^+$CD8$^+$CD25$^{High}$FOXP3$^{High}$ T$_{Reg}$ cells compared to both CD3$^+$CD8$^+$ CD8$^+$ effector T cells and CD3$^+$CD8$^+$CD25$^{Low}$FOXP3$^{Low}$ CD4$^+$ effector T cells. In contrast, hIL-2/F5111 complex treatment showed no T cell subset bias compared to free hIL-2.

Example 8

This example describes the fabrication of a microparticle encapsulating the F5111 immunocytokine. The immunocytokine used in this example is F5111 IC LN35.

Encapsulation of F5111 IC within the TolAPC core was explored. Three loading doses of F5111 IC were tested during particle synthesis, ancapsulated F5111 IC was measured using a BCA protein assay. The highest loading dose (1.25 µg F5111/mg PLGA) led to the most efficient encapsulation and was used for subsequent experiments (FIG. 18). Next, particle synthesis parameters were varied to further optimize F5111 encapsulation efficiency, including particle size, concentration of NaCl in the external phase, and the pH of the internal aqueous phase (Table 1).

TABLE 1

| Batch # | Diameter | External NaCl | Inner Phase |
| --- | --- | --- | --- |
| 1 | 1 um | None | 5 mM NaCl |
| 2 | 7-8 um | None | 5 mM NaCl |
| 3 | >>8 um | None | 5 mM NaCl |
| 4 | 1 um | 125 mM | 5 mM NaCl |
| 5 | 1 um | 400 mM | 5 mM NaCl |
| 6 | 1 um | None | PBS pH 7 |
| 7 | 1 um | None | PBS pH 6 |
| 8 | 1 um | None | PBS pH 5 |

Maximum loading efficiency was achieved under acidic conditions (FIG. 19, Batch #8), and loading efficiency also increased when water was used as the inner aqueous phase (Batch #1) instead of PBS (Batch #6). F5111 IC-loaded particles were synthesized substituting various buffers at pH 5 into the inner aqueous phase (Table 2).

TABLE 2

| Batch # | Diameter | External NaCl | Inner Phase |
| --- | --- | --- | --- |
| 1 | 1 um | None | 5 mM NaCl |
| 2 | 1 um | None | PBS pH 5 |
| 3 | 1 um | None | Citrate Buffer pH 5 |
| 4 | 1 um | None | Acetate Buffer pH 5 |

The first three batches of particles encapsulated similar amounts of F5111 IC, and the highest loading was achieved using an inner phase consisting of a sodium acetate buffer at pH 5 (FIG. 20).

To determine whether F5111 IC-encapsulated MPs could induce in vitro T$_{Reg}$ cell expansion, CD4$^+$ T cells were isolated from the spleens of B6 mice and incubated with unconjugated F5111 IC or F5111 IC-loaded PLGA MPs for 3 days. Cells were then stained for CD4, CD25, and FOXP3, and analyzed using flow cytometry. As shown in FIG. 21, both unconjugated F5111 IC and F5111 IC-loaded MPs expanded FOXP3+ cells as compared to untreated cells on day 0 and day 3.

Example 9

This example describes T$_{Reg}$ cell stimulation with F5111 IC-loaded microparticles. The immunocytokine used in this example is F5111 IC LN35.

To evaluate the functionality of F5111 IC-loaded particles, mouse CD4+ T cells were stimulated with F5111 IC-loaded microparticles to identify an optimal stimulation time for maximum pSTAT5 expression, and pSTAT5 expression was compared to that of cells stimulated with free F5111 IC. CD4+ T cells were isolated from C57BL/6 mice and incubated with various doses of F5111 IC-loaded microparticles or equivalent doses of free F5111 IC for 20, 40, 60, or 120 minutes. CD4$^+$ T cells were activated by both F5111 IC-loaded microparticles and free F5111 IC in a dose-dependent manner, and maximum pSTAT5 activation was observed after a stimulation time of 60 minutes (FIG. 22). These results suggest that encapsulation of F5111 IC can be used as an alternative to surface-conjugated F5111 IC to generate antigen-specific TolAPCs.

Example 10

This example demonstrates antigen-specific engagement of T cells by peptide/MHC-coated MPs.

MPs of ~1 μm diameter were fabricated from poly(lactic-co-glycolic acid) (PLGA) or a 75:25 (w/w) blend of PLGA to poly(beta-amino ester) (PBAE). EDC/NHS chemistry was used to conjugate I-Ab OVA(329-337)-loaded MHC II tetramer to the surface of the particles to generate ova-MPs. A control I-A(b) tetramer was used to generate control MPs. CD4$^+$ T cells were enriched from OT-II mice, labelled with CFSE, and incubated with 0.01 mg fluorescent MPs for 1 hour at 37° C. to evaluate the extent of OVA-specific binding using flow cytometry. Compared to blank particle controls, OVA peptide-loaded MHC-coated MPs demonstrated enhanced engagement of OVA-specific CD4$^+$ T cells, illustrating that coated MPs can achieve antigen-specific T cell engagement (FIG. 23).

Example 11

This example describes the generation of TolAPCs that effect antigen-specific $T_{Reg}$ induction.

OVA peptide/MHC tetramer-coated and control TolAPCs were synthesized as in example 10, except that during conjugation, a monoclonal antibody directed against CD28 was also added as a costimulatory signal. Naïve CD4$^+$ T cells were harvested from OT-II mice and incubated with TolAPCs for 3 days in the presence of IL-2 and TGF-β. Following incubation, cells were stained for FOXP3 to assess $T_{Reg}$ cell induction. TolAPCs surface-conjugated with OVA peptide/MHC tetramers and anti-CD28 induced OVA-specific $T_{Reg}$ cells from naïve OT-II CD4+ T cells, whereas TolAPC surface-conjugated with control tetramer did not induce $T_{Reg}$ cells, as shown in FIG. 24. These data indicate that TolAPCs can induce $T_{Reg}$ cells in an antigen-specific manner.

Nano-scale TolAPCs with surface-conjugated proteins also were generated. Specifically, PLGA or PLGA/PBAE nanoparticles (~200 nm in diameter) were synthesized using emulsion techniques. Four proteins were chemically coupled to the surface of TolAPCs to provide specificity and regulatory cues for $T_{Reg}$ cell induction: (i) OVA peptide/MHC tetramers, (ii) a monoclonal antibody against CD28, (iii) TGF-β, and (iv) IL-2. TolAPCs were cultured with primary naïve CD4$^+$ T cells isolated from OT-II mice. Flow cytometry was used to assess TolAPC/T cell binding and $T_{Reg}$ cell induction based on FOXP3 staining. Nanoscale TolAPCs induced up to 45% ovalbumin-specific $T_{Reg}$ cells without the presence of any exogenous factors (FIG. 25), further supporting the use of TolAPCs for antigen-specific $T_{Reg}$ cell induction.

Anisotropic nano-TolAPCs with surface-conjugated signals also were prepared. PLGA or PLGA/PBAE nanoparticles (~200 nm in diameter) were synthesized using emulsion techniques. Using an automated thin-film stretching device, spherical particles were mechanically stretched along one axis to an aspect ratio of 2:1 to generate ellipsoidal particles. Four proteins were chemically coupled to the surface of spherical or ellipsoidal TolAPCs to provide specificity and regulatory cues for $T_{Reg}$ cell induction: (i) OVA peptide/MHC tetramers, (ii) a monoclonal antibody against CD28, (iii) TGF-β, and (iv) IL-2. TolAPCs were cultured with primary naïve CD4$^+$ T cells isolated from OT-II mice. Flow cytometry was used to assess TolAPC/T cell binding and $T_{Reg}$ cell induction via FOXP3 staining. Ellipsoidal nano-TolAPCs improved $T_{Reg}$ cell induction compared to spherical nano-TolAPCs, as shown in FIG. 26.

Example 12

This example describes the generation of TolAPCs comprising a protein or small molecule encapsulated within the particle core.

PLGA microparticles loaded with varying amounts of the TGF-β cytokine and the small molecule immunosuppressive drug rapamycin were synthesized using a double emulsion technique. Rapamycin loading efficiency was determined by UV spectrophotometry and TGF-β release was measured by ELISA. Particles were surface-functionalized with ova peptide-loaded I-A(b) MHC II tetramers and anti-CD28 to generate TolAPCs. Naïve CD4$^+$ T cells isolated from OT-II mice were incubated with TolAPCs for 3 days in the presence of IL-2. Cells were then analyzed for FOXP3 levels via flow cytometry. TolAPCs containing TGF-β and rapamycin elicited robust $T_{Reg}$ cell induction, and loading doses of 125 ng TGF-β and 25 μg rapamycin/mg PLGA during TolAPC synthesis were found to be most effective (FIG. 27).

Example 13

This example describes the generation of antigen-specific TolAPCs with surface-conjugated F5111 IC and their use in vivo to target and expand $T_{Reg}$ cells.

An EAE prevention study was performed in mice. PLGA/PBAE MPs (~1 μm diameter) were synthesized using emulsion techniques. Particles were chemically conjugated with MOG peptide-loaded I-A(b) MHC II tetramers (5 μg/mg) and F5111 IC LN15 (5 μg/mg) to generate TolAPCs. TolAPCs or blank control MPs were injected into the inguinal lymph nodes of 9-week-old female B6 mice (2 mg/lymph node) one day before EAE induction. One day after induction, 2 mg TolAPCs were injected intravenously. Mice were scored according to disease severity (0=no paralysis; 3=complete hind limb paralysis). TolAPC treatment significantly prevented EAE development in mice compared to blank particles (FIG. 28A). Moreover, treatment delayed disease onset and reduced disease incidence in mice, with only 30% of TolAPC-treated mice developing disease compared to 100% of mice treated with blank control MPs.

An OVA-expressing tumor protection study was performed in mice. Specifically, carboxylated iron dextran MPs (~3 μm diameter) were chemically conjugated with OVA peptide-loaded I-A(b) MHC II tetramers (5 μg/mg) and/or F5111 IC LN25 (5 μg/mg) to generate TolAPCs. TolAPCs or blank control MPs were injected into the inguinal lymph nodes of 9-week-old female C57BL/6 mice (2 mg/lymph node) one day before tumor implantation. The following day, 5×10$^5$ MC38-OVA cells were inoculated subcutaneously into the right flank. Tumors were measured starting on day 7 post-inoculation, and mice were euthanized when tumors reached an area of 200 mm$^2$ or when tumors ulcerated. Treatment with MPs coated with both OVA peptide/MHC tetramer+F5111 IC LN25 TolAPC treatment conferred tumor protection, translating to more rapid tumor growth (FIG. 29A) and shorter survival (FIG. 29B) compared to mice treated with blank control MPs. Taken together, these studies demonstrate that TolAPCs induce antigen-specific expansion of $T_{Reg}$ cells in vivo and prevent autoimmune disease pathogenesis in mice, illustrating their therapeutic potential for autoimmune disorder treatment and transplantation medicine.

REFERENCES

All references, including publications, patent applications, and patents, cited herein are hereby incorporated by reference to the same extent as if each reference were individually and specifically indicated to be incorporated by reference and were set forth in its entirety herein.

1. ElEssawy B, Li X C. Type 1 diabetes and T regulatory cells. Pharmacol Res. 2015 Aug. 1; 98(SupplementC): 22-30.
2. Battaglia M, Roncarolo M-G. Immune intervention with T regulatory cells: Past lessons and future perspectives for type 1 diabetes. Semin Immunol. 2011 Jun. 1; 23(3):182-194.
3. Marek-Trzonkowska N, Mysliwiec M, Dobyszuk A, Grabowska M, Techmanska I, Juscinska J, Wujtewicz M A, Witkowski P, Mlynarski W, Balcerska A, Mysliwska J, Trzonkowski P. Administration of CD4+ CD25highCD127-regulatory T cells preserves β-cell function in type 1 diabetes in children. Diabetes Care. 2012 September; 35(9):1817-1820. PMCID: PMC3425004
4. Lee K, Nguyen V, Lee K-M, Kang S-M, Tang Q. Attenuation of donor-reactive T cells allows effective control of allograft rejection using regulatory T cell therapy. Am J Transplant Off J Am Soc Transplant Am Soc Transpl Surg. 2014 January; 14(1):27-38. PMCID: PMC5262439
5. Tang Q, Vincenti F. Transplant trials with Tregs: perils and promises. J Clin Invest. 2017 Jun. 30; 127(7):2505-2512. PMID: 0
6. You W-P, Henneberg M. Type 1 diabetes prevalence increasing globally and regionally: the role of natural selection and life expectancy at birth. BMJ Open Diabetes Res Care. 2016; 4(1): e000161. PMCID: PMC4780042
7. Patterson C, Guariguata L, Dahlquist G, Soltész G, Ogle G, Silink M. Diabetes in the young—a global view and worldwide estimates of numbers of children with type 1 diabetes. Diabetes Res Clin Pract. 2014 Feb. 1:103(2): 161-175.
8. Writing Team for the Diabetes Control and Complications Trial/Epidemiology of Diabetes Interventions and Complications Research Group. Sustained effect of intensive treatment of type 1 diabetes mellitus on development and progression of diabetic nephropathy: the Epidemiology of Diabetes Interventions and Complications (EDIC) study. JAMA. 2003 Oct. 22; 290(16):2159-2167. PMCID: PMC2622725
9. Maahs D M, Rewers M. Editorial: Mortality and renal disease in type 1 diabetes mellitus—progress made, more to be done. J Clin Endocrinol Metab. 2006 October; 91(10):3757-3759. PMID: 17028289
10. Boyman O, Sprent J. The role of interleukin-2 during homeostasis and activation of the immune system. Nat Rev Immunol. 2012 Feb. 17; 12(3):180-190. PMID: 22343569
11. Liao W, Lin J-X, Leonard W J. Interleukin-2 at the crossroads of effector responses, tolerance, and immunotherapy. Immunity. 2013 Jan. 24; 38(1):13-25. PMCID: PMC3610532
12. Klatzmann D, Abbas A K. The promise of low-dose interleukin-2 therapy for autoimmune and inflammatory diseases. Nat Rev Immunol. 2015 May; 15(5):283-294. PMID: 25882245
13. Wang X, Rickert M, Garcia K C. Structure of the quaternary complex of interleukin-2 with its alpha, beta, and gammac receptors. Science. 2005 Nov. 18; 310 (5751):1159-1163. PMID: 16293754
14. Malek T R. The Biology of Interleukin-2. Annu Rev Immunol. 2008; 26(1):453-479. PMID: 18062768
15. Boyman O, Kovar M, Rubinstein M P, Surh C D, Sprent J. Selective stimulation of T cell subsets with antibody-cytokine immune complexes. Science. 2006 Mar. 31; 311(5769):1924-1927. PMID: 16484453
16. Tang Q, Adams J Y, Penaranda C, Melli K, Piaggio E, Sgouroudis E, Piccirillo C A, Salomon B L, Bluestone J A. Central role of defective interleukin-2 production in the triggering of islet autoimmune destruction. Immunity. 2008 May; 28(5):687-697. PMCID: PMC2394854
17. Grinberg-Bleyer Y, Baeyens A, You S, Elhage R, Fourcade G, Gregoire S, Cagnard N, Carpentier W, Tang Q, Bluestone J, Chatenoud L, Klatzmann D, Salomon B L, Piaggio E. IL-2 reverses established type 1 diabetes in NOD mice by a local effect on pancreatic regulatory T cells. J Exp Med. 2010 Aug. 30; 207(9):1871-1878. PMID: 20679400
18. Webster K E, Walters S, Kohler R E, Mrkvan T, Boyman O, Surh C D, Grey S T, Sprent J. In vivo expansion of T reg cells with IL-2-mAb complexes: induction of resistance to EAE and long-term acceptance of islet allografts without immunosuppression. J Exp Med. 2009 Apr. 13; 206(4):751-760. PMID: 19332874
19. Liu R, Zhou Q, La Cava A, Campagnolo D I, Van Kaer L, Shi F-D. Expansion of regulatory T cells via IL-2/anti-IL-2 mAb complexes suppresses experimental myasthenia. Eur J Immunol. 2010 Jun. 1; 40(6):1577-1589.
20. Spangler J B, Tomala J, Luca V C, Jude K M, Dong S, Ring A M, Votavova P, Pepper M, Kovar M, Garcia K C. Antibodies to Interleukin-2 Elicit Selective T Cell Subset Potentiation through Distinct Conformational Mechanisms. Immunity. 2015 May 19; 42(5):815-825.
21. Oelke M, Maus M V, Didiano D, June C H, Mackensen A, Schneck J P. Ex vivo induction and expansion of antigen-specific cytotoxic T cells by HLA-Ig-coated artificial antigen-presenting cells. Nat Med. 2003 May; 9(5): 619.
22. Rossjohn J, Gras S, Miles J J, Turner S J, Godfrey D I, McCluskey J. T Cell Antigen Receptor Recognition of Antigen-Presenting Molecules. Annu Rev Immunol. 2015; 33(1):169-200. PMID: 25493333
23. Ugel S, Zoso A, Santo C D, Li Y, Marigo I, Zanovello P, Scarselli E, Cipriani B, Oelke M, Schneck J P, Bronte V. In vivo Administration of Artificial Antigen-Presenting Cells Activates Low-Avidity T Cells for Treatment of Cancer. Cancer Res. 2009 Dec. 15; 69(24):9376-9384. PMID: 19934317
24. Sunshine J C, Perica K, Schneck J P, Green J J. Particle shape dependence of CD8+ T cell activation by artificial Antigen Presenting Cells. Biomaterials. 2014 January; 35(1):269-277. PMCID: PMC3902087
25. Meyer R A, Sunshine J C, Perica K, Kosmides A K, Aje K, Schneck J P, Green J J. Biodegradable Nanoellipsoidal Artificial Antigen Presenting Cells for Antigen Specific T-Cell Activation. Small. 2015 Apr. 1; 11(13):1519-1525.
26. Li L, Yi Z, Wang B, Tisch R. Suppression of ongoing T cell-mediated autoimmunity by peptide-MHC class II dimer vaccination. J Immunol Baltim Md 1950. 2009 Oct. 1;183(7):4809-4816. PMCID: PMC5444462
27. Lin M, Stoica-Nazarov C, Surls J, Kehl M, Bona C, Olsen C, Brumeanu T D, Casares S. Reversal of type 1 diabetes by a new MHC II-peptide chimera: "Single-epitope-mediated suppression" to stabilize a polyclonal autoimmune T-cell process. Eur J Immunol. 2010 August; 40(8):2277-2288. PMID: 20540111
28. Clemente-Casares X, Blanco J, Ambalavanan P. Yamanouchi J, Singha S, Fandos C, Tsai S, Wang J, Garabatos N, Izquierdo C, Agrawal S, Keough M B, Yong V W, James E, Moore A, Yang Y, Stratmann T, Serra P. Santamaria P. Expanding antigen-specific regulatory networks to treat autoimmunity. Nature. 2016 Feb. 25; 530(7591):434-440. PMID: 26886799
29. Spangler J B, Trotta E, Tomala J, Peck A, Young T A, Savvides C S, Silveria S, Votavova P, Salafsky J, Pande V S, Kovar M, Bluestone J A, Garcia K C. Engineering a Single-Agent Cytokine/Antibody Fusion That Selectively Expands Regulatory T Cells for Autoimmune Disease Therapy. J Immunol Baltim Md 1950. 2018 Oct. 1; 201(7):2094-2106. PMCID: PMC6173196
30. Pasche N, Neri D. Immunocytokines: a novel class of potent armed antibodies. Drug Discov Today. 2012 Jun. 1; 17(11):583-590.
31. Trotta E, Bessette P H, Silveria S L, Ely L K, Jude K M, Le D T, Holst C R, Coyle A, Potempa M, Lanier L L, Garcia K C, Crellin N K, Rondon I J, Bluestone J A. A human anti-IL-2 antibody that potentiates regulatory T cells by a structure-based mechanism. Nat Med. 2018 July; 24(7):1005-1014. PMID: 29942088
32. Wesley J D, Sather B D, Perdue N R, Ziegler S F, Campbell D J. Cellular Requirements for Diabetes Induction in DO11.10xRIPmOVA Mice. J Immunol. 2010 Oct. 15; 185(8):4760-4768. PMID: 20855871
33. Buckner J H. Mechanisms of impaired regulation by CD4(+)CD25(+)FOXP3(+) regulatory T cells in human autoimmune diseases. Nat Rev Immunol. 2010 December; 10(12):849-859. PMCID: PMC3046807
34. Walker L S K. Regulatory T cells overturned: the effectors fight back. Immunology. 2009 April; 126(4):466-474. PMCID: PMC2673359
35. Roncarolo M-G, Battaglia M. Regulatory T-cell immunotherapy for tolerance to self antigens and alloantigens in humans. Nat Rev Immunol. 2007 August; 7(8):585-598. PMID: 17653126
36. Yodoi J, Teshigawara K, Nikaido T, Fukui K, Noma T, Honjo T, Takigawa M, Sasaki M, Minato N, Tsudo M. TCGF (IL 2)-receptor inducing factor(s). I. Regulation of IL 2 receptor on a natural killer-like cell line (YT cells). J Immunol Baltim Md 1950. 1985 March; 134(3):1623-1630. PMID: 2578514
37. Kuziel W A, Ju G, Grdina T A, Greene W C. Unexpected effects of the IL-2 receptor alpha subunit on high affinity IL-2 receptor assembly and function detected with a mutant IL-2 analog. J Immunol. 1993 Apr. 15:150(8):3357-3365. PMID: 8468475
38. Ring A M, Lin J-X, Feng D, Mitra S. Rickert M, Bowman G R, Pande V S, Li P, Moraga I, Spolski R, Ozkan E, Leonard W J, Garcia K C. Mechanistic and structural insight into the functional dichotomy between IL-2 and IL-15. Nat Immunol. 2012 December; 13(12):1187-1195. PMCID: PMC3501574
39. Boder E T, Wittrup K D. Yeast surface display for screening combinatorial polypeptide libraries. Nat Biotechnol. 1997 June; 15(6):553-557. PMID: 9181578
40. Crawford F, Stadinski B, Jin N, Michels A, Nakayama M, Pratt P, Marrack P, Eisenbarth G, Kappler J W. Specificity and detection of insulin-reactive CD4+ T cells in type 1 diabetes in the nonobese diabetic (NOD) mouse. Proc Natl Acad Sci USA. 2011 Oct. 4; 108(40):16729-16734. PMCID: PMC3189014
41. Murray P J. The JAK-STAT signaling pathway: input and output integration. J Immunol Baltim Md 1950. 2007 Mar. 1; 178(5):2623-2629.
42. Bromberg J, Wang T C. Inflammation and cancer: IL-6 and STAT3 complete the link. Cancer Cell. 2009 Feb. 3; 15(2):79-80. PMCID: PMC3684978
43. Raimondi G, Sumpter T L, Matta B M, Pillai M, Corbitt N, Vodovotz Y, Wang Z, Thomson A W. Mammalian target of rapamycin inhibition and alloantigen-specific regulatory T cells synergize to promote long-term graft survival in immunocompetent recipients. J Immunol Baltim Md 1950. 2010 Jan. 15; 184(2):624-636. PMCID: PMC2923839
44. Turnquist H R, Raimondi G, Zahorchak A F, Fischer R T, Wang Z, Thomson A W. Rapamycin-Conditioned Dendritic Cells Are Poor Stimulators of Allogeneic CD4+ T Cells, but Enrich for Antigen-Specific Foxp3$^+$ T Regulatory Cells and Promote Organ Transplant Tolerance. J Immunol. 2007 Jun. 1; 178(11):7018-7031. PMID: 17513751
45. Jhunjhunwala S, Raimondi G, Thomson A W, Little S R. Delivery of rapamycin to dendritic cells using degradable microparticles. J Control Release Off J Control Release Soc. 2009 Feb. 10; 133(3):191-197. PMCID: PMC2925512
46. Dawson N A J, Vent-Schmidt J, Levings M K. Engineered Tolerance: Tailoring Development, Function, and Antigen-Specificity of Regulatory T Cells. Front Immunol [Internet]. 2017 [cited 2018 Mar. 15]; 8. Available from: frontiersin.org/articles/10.3389/fimmu.2017.01460/full
47. Bluestone J A, Tang Q. T reg cells—the next frontier of cell therapy. Science. 2018 Oct. 12:362(6411):154-155.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Sequences:

SEQ ID NO: 1
F5111 $V_H$
QLQLQESGPGLVKPSQTLSLTCTVSGGSISSGGYYWSWIRQHPGKGLEWIGYIYYSGSTYYNPS
LKSRVTISVDTSKNQFSLKLSSVTAADTAVYYCARTPTVTGDWFDPWGRGTLVTVSS

SEQ ID NO: 2
Human IgG1 $C_H1$, $C_H2$, and $C_H3$
*ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCIPCPAPELLGG
PSVFLFPPKPKDTLMISRTPEVTCVVVDVSHEDPEVKFNWYVDGVEVHNAKTKPREEQ
YNSTYRVVSVLTVLHQDWLNGKEYK*CKVSNKALPAPIEKTISKAKGQPREPQVYTLPPSR
*EEMTKNQVSLTCLVKGFYPSDIAVEWESNGQPENN*YKTTPPVLDSDGSFFLYSKLTVDKS
*RWQQGNVFSCSVMHEALHNHY*TQKSLSLSPGK SEQ ID NO: 3
Signal sequence
METDTLLLWVLLLWVPGSTGD

SEQ ID NO: 4
Signal sequence
MRVPAQLLGLLLLWLPGARC

SEQ ID NO: 5
Signal sequence-F5111 $V_H$-human IgG1 $C_H1$, $C_H2$, and $C_H3$
METDTLLLWVLLLWVPGSTGDQLQLQESGPGLVKPSQTLSLTCTVSGGSISSGGYYWSWI
RQHPGKGLEWIGYIYYSGSTYYNPSLKSRVTISVDTSKNQFSLKLSSVTAADTAVYYCARTPTVTG
DWFDPWGRGTLVTVSS*ASTKGPSVFPLAPSSKSTSGGTAALGCLVKDYFPEPVTVSWNSG
ALTSGVHTFPAVIQSSGLYSLSSVVTVPSSSLGTQTYICNVNHKPSNTKVIKKVEPKSCDK
**THTCPPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPENNYKTTPPVLD
SDGSFFLYSKLTVSKSRWQQGNVFSCSVMHEALHNHYTQKSLSLSPGK**

SEQ ID NO: 6
Human IL-2
APTSSSTKKTQLQLEHLLLDLQMILNGINNYKNPKLTRMLTFKFYMPKKATELKHLQCLE
EELKPLEEVLNLAQSKNFHLRPRDLISNINVIVLELKGSETTFMCEYADETATIVEFLNRWI
TFCQSIISTLT SEQ ID NO: 7
F5111 $V_L$
NFMLTQPHSVSESPGKTVTISCTRSSGSIASNYVQWYQQRPGSSPTTVIYEDNQRPSGVPDRFS
GSIDSSSNSASLTISGLKTEDEADYYCQSYDSSNVVFGGGTKLTVL SEEQ ID NO: 8
Human Lambda $C_L$
**GQPKAAPSVTLFPPSSEELQANKATLVCLISDFYPGAVTVAWKADSSPVKAGVETTTPSK
QSNNKYAASSYLSLTPEQWKSHRSYSCQVTHEGSTVEKTVAPTECS**

SEQ ID NO: 9
Signal sequence
MYRMQLLSCIALSLALVTNS

SEQ ID NO: 10
Signal sequence-F5111 $V_L$-human Lambda $C_L$
MRVPAQLLGLLLLWLPGARCGSNFMLTQPHSVSESPGKTVTISCTRSSGSIASNYVQWYQ
QRPGSSPTTVIYEDNQRPSGVPDRFSGSIDSSSNSASLTISGLKTEDEADYYCQSYSSNVVFGG
GTKLTVLGQPKAAPSVTLFPPSSEELQANKATLVCLISDFYPGAVTVAWKADSSPVKAGVE
TTTPSKQSNNKYAASSYLSLTPEQWKSHRSYSCQVTHEGSTVEKTVAPTECS SEQ ID NO: 11
Signal sequence-human IL-2-Linker-F5111 $V_L$-human Lambda $C_L$
MYRMQLLSCIALSLALVTNSAPTSSSTKKTQLQLEHLLLDLQMILNGINNYKNPKLTRM
LTFKFYMPKKATELKHLQCLEEELKPLEEVLNLAQSKNFHLRPRDLISNINVIVLELKGSE
TTFMCEYADETATIVEFLNRWITFCQSIISTLTGGGGSGGGGSGGGGSNFMLTQPHSVSESP
GKTVTISCTRSSGSIASNYVQWYQQRPGSSPTTVIYEDNQRPSGVPDRFSGSIDSSSNSASLTISG LKTEDEADYYCQSYDSSNVVFGGGTKLTVIGQPKAAPSVTLFPPSSEELQANKAYLVCLISD FYPGAVTVAWKADSSPVKAGVETTTPSKQSNNKYAASSYLSLTPEQWKSHRSYSCQVTHE GSTVEKTVAPTECS

The invention claimed is:

1. A biodegradable particle comprising:
   a polyester or polyester blend;
   a first protein that binds to an immune cell;
   a second protein that promotes proliferation and/or activation of immune cells; and
   a third soluble protein or small molecule encapsulated within the particle,
   wherein:
   (i) the first protein is a MHC II tetramer peptide complex attached to a surface of the particle or to a coating on the surface thereof; and
   (ii) the second protein is an immunocytokine that binds to a polypeptide complex comprising an IL-2 receptor, wherein said immunocytokine comprises at least a portion of an antibody and at least a portion of a cytokine and is either attached to a surface of the particle or to a coating on the surface thereof or encapsulated within the particle.

2. The biodegradable particle of claim 1, wherein the polyester or polyester blend is selected from the group consisting of poly (lactic-co-glycolic acid) (PLGA), polycaprolactone (PCL), polyglycolide (PGA), poly(lactic acid) (PLA), polyhydroxyalkanoate (PHA), poly-3-hydroxybutyrate (P3HB), poly(acrylic acid) (PAA), poly(3-hydroxybutyrate-co-3-hydroxyvalerate) (PHBV), poly(beta-amino ester) (PBAE), and combinations or blends thereof.

3. The biodegradable particle of claim 1, wherein the immune cell to which the first protein binds comprises a T cell.

4. The biodegradable particle of claim 1, wherein the immunocytokine comprises the amino acid sequences of SEQ ID NO: 5 and SEQ ID NO: 11.

5. The biodegradable particle of claim 1, wherein the third soluble protein is an interleukin and/or a cytokine.

6. The biodegradable particle of claim 1, wherein the small molecule is an immunosuppressive drug.

7. The biodegradable particle of claim 1, wherein the small molecule is rapamycin, cyclosporine A, or analogs thereof.

8. The biodegradable particle of claim 1, wherein said particle is a microparticle having an average diameter of from about 1 micron to about 5 microns.

9. The biodegradable particle of claim 1, wherein said particle is a nanoparticle having an average diameter of from about 50 nm to about 1000 nm.

10. The biodegradable particle of claim 1, wherein said particle is anisotropic and has a non-spherical shape.

11. The biodegradable particle of claim 1, wherein said particle has a prolate ellipsoidal shape.

12. The biodegradable particle of claim 1, wherein said coating comprises one or more synthetic and/or natural lipids and/or lipid membranes.

13. The biodegradable particle of claim 1, wherein the first and second proteins are attached to the coating, and said coating comprises one or more synthetic and/or natural lipids and/or lipid membranes.

14. The biodegradable particle of claim 1, wherein the first protein and the second protein are present on the particle in a 1:1 molar ratio.

15. The biodegradable particle of claim 1, wherein said particle comprises a combination of poly(lactic-co-glycolic acid) (PLGA) and poly(beta-amino ester) (PBAE).

16. A method for treating a disease or condition in a subject in need thereof, said method comprising administering to the subject a therapeutically effective amount of a biodegradable particle of claim 1.

* * * * *

UNITED STATES PATENT AND TRADEMARK OFFICE
CERTIFICATE OF CORRECTION

PATENT NO. : 12,151,000 B2
APPLICATION NO. : 17/602856
DATED : November 26, 2024
INVENTOR(S) : Green et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 126 days.

Signed and Sealed this
Fifth Day of August, 2025

Coke Morgan Stewart
*Acting Director of the United States Patent and Trademark Office*